United States Patent
Do et al.

(10) Patent No.: US 10,755,805 B1
(45) Date of Patent: *Aug. 25, 2020

(54) ANCESTRY PAINTING WITH LOCAL ANCESTRY INFERENCE

(71) Applicant: 23andMe, Inc., Mountain View, CA (US)

(72) Inventors: Chuong Do, Mountain View, CA (US); Eric Durand, Sceaux (FR); John Michael Macpherson, Mountain View, CA (US)

(73) Assignee: 23andMe, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/446,465

(22) Filed: Jun. 19, 2019

Related U.S. Application Data

(63) Continuation of application No. 15/181,088, filed on Jun. 13, 2016, which is a continuation of application No. 13/800,683, filed on Mar. 13, 2013, now Pat. No. 9,367,800.

(60) Provisional application No. 61/724,228, filed on Nov. 8, 2012.

(51) Int. Cl.
*G16H 10/60* (2018.01)
*G06F 16/29* (2019.01)
*G06N 5/02* (2006.01)
*G06N 5/04* (2006.01)

(52) U.S. Cl.
CPC ............ *G16H 10/60* (2018.01); *G06F 16/29* (2019.01); *G06N 5/022* (2013.01); *G06N 5/04* (2013.01)

(58) Field of Classification Search
CPC .............................. G06F 15/00–15/76; G06F 2015/761–2015/768; G06F 16/29; G06N 20/00; G06N 99/005; G06N 5/022; G06N 5/04; G16H 10/60
USPC .......................................................... 706/12
See application file for complete search history.

(56) References Cited

U.S. PATENT DOCUMENTS

| | | |
|---|---|---|
| 6,570,567 B1 | 5/2003 | Eaton |
| 6,703,228 B1 | 3/2004 | Landers et al. |
| 7,142,205 B2 | 11/2006 | Chithambaram et al. |
| 7,567,894 B2 | 7/2009 | Durand et al. |
| 7,729,863 B2 | 6/2010 | Ostrander et al. |
| 7,818,281 B2 | 10/2010 | Kennedy et al. |
| 7,848,914 B2 | 12/2010 | Durand et al. |

(Continued)

FOREIGN PATENT DOCUMENTS

| | | |
|---|---|---|
| WO | WO 2009/002942 | 12/2008 |
| WO | WO 2016/073953 | 5/2016 |

OTHER PUBLICATIONS

U.S. Office Action dated Sep. 26, 2018 issued in U.S. Appl. No. 15/267,053.

(Continued)

*Primary Examiner* — Michael B Holmes
(74) *Attorney, Agent, or Firm* — Weaver Austin Villeneuve & Sampson LLP; David K. Buckingham

(57) ABSTRACT

Presenting ancestral origin information, comprising: receiving a request to display ancestry data of an individual; obtaining ancestry composition information of the individual, the ancestry composition information including information pertaining to a proportion of the individual's genotype data that is deemed to correspond to a specific (Continued)

ancestry; and presenting the ancestry composition information to be displayed.

28 Claims, 32 Drawing Sheets

Specification includes a Sequence Listing.

(56) References Cited

U.S. PATENT DOCUMENTS

| | | | |
|---|---|---|---|
| 7,957,907 B2 | 6/2011 | Sorenson et al. | |
| 7,983,893 B2 | 7/2011 | Durand et al. | |
| 8,187,811 B2 * | 5/2012 | Eriksson | A61K 31/7088 435/6.1 |
| 8,195,446 B2 | 6/2012 | Durand et al. | |
| 8,207,316 B1 | 6/2012 | Bentwich | |
| 8,214,192 B2 | 7/2012 | Durand et al. | |
| 8,214,195 B2 | 7/2012 | Durand et al. | |
| 8,285,486 B2 | 10/2012 | Martin et al. | |
| 8,428,886 B2 | 4/2013 | Wong et al. | |
| 8,443,339 B2 | 5/2013 | Letourneau | |
| 8,463,554 B2 | 6/2013 | Hon et al. | |
| 8,467,976 B2 | 6/2013 | Lo et al. | |
| 8,473,273 B2 | 6/2013 | Durand et al. | |
| 8,510,057 B1 * | 8/2013 | Avey | G16B 20/00 702/19 |
| 8,543,339 B2 * | 9/2013 | Wojcicki | G16B 50/00 702/19 |
| 8,589,437 B1 | 11/2013 | Khomenko et al. | |
| 8,645,118 B2 | 2/2014 | Durand et al. | |
| 8,645,343 B2 | 2/2014 | Wong et al. | |
| 8,666,271 B2 | 3/2014 | Saiki | |
| 8,666,721 B2 | 3/2014 | Durand et al. | |
| 8,685,737 B2 | 4/2014 | Serber et al. | |
| 8,731,819 B2 | 5/2014 | Dzubay et al. | |
| 8,738,297 B2 | 5/2014 | Sorenson et al. | |
| 8,786,603 B2 | 7/2014 | Rasmussen et al. | |
| 8,798,915 B2 | 8/2014 | Dzubay et al. | |
| 8,855,935 B2 | 10/2014 | Myres et al. | |
| 8,990,250 B1 | 3/2015 | Chowdry et al. | |
| 9,026,423 B2 | 5/2015 | Durand et al. | |
| 9,116,882 B1 * | 8/2015 | Macpherson | G16B 45/00 |
| 9,213,944 B1 * | 12/2015 | Do | G06N 20/00 |
| 9,213,947 B1 * | 12/2015 | Do | G06N 5/04 |
| 9,218,451 B2 | 12/2015 | Wong et al. | |
| 9,262,567 B2 | 2/2016 | Durand et al. | |
| 9,323,632 B2 | 4/2016 | Durand et al. | |
| 9,336,177 B2 | 5/2016 | Hawthorne et al. | |
| 9,367,800 B1 * | 6/2016 | Do | G16B 20/00 |
| 9,390,225 B2 | 7/2016 | Barber et al. | |
| 9,405,818 B2 | 8/2016 | Chowdry et al. | |
| 9,836,576 B1 * | 12/2017 | Do | G06N 20/00 |
| 9,864,835 B2 | 1/2018 | Avey et al. | |
| 9,886,576 B2 | 2/2018 | Urakabe | |
| 9,977,708 B1 * | 5/2018 | Do | G16B 45/00 |
| 10,025,877 B2 * | 7/2018 | Macpherson | G16B 99/00 |
| 10,296,847 B1 * | 5/2019 | Do | G06N 5/04 |
| 10,437,858 B2 * | 10/2019 | Naughton | G16H 10/60 |
| 10,572,831 B1 * | 2/2020 | Do | G16B 20/00 |
| 10,658,071 B2 | 5/2020 | Do et al. | |
| 10,699,803 B1 | 6/2020 | Do et al. | |
| 2002/0095585 A1 | 7/2002 | Scott | |
| 2002/0133495 A1 | 9/2002 | Rienhoff, Jr. et al. | |
| 2003/0113729 A1 | 6/2003 | DaQuino et al. | |
| 2003/0135096 A1 | 7/2003 | Dodds | |
| 2003/0172065 A1 | 9/2003 | Sorenson et al. | |
| 2003/0179223 A1 | 9/2003 | Ying et al. | |
| 2003/0186244 A1 | 10/2003 | Margus et al. | |
| 2004/0002818 A1 | 1/2004 | Kulp et al. | |
| 2004/0088191 A1 | 5/2004 | Holden | |
| 2004/0175700 A1 | 9/2004 | Geesaman | |
| 2004/0229213 A1 * | 11/2004 | Legrain | C12N 15/1055 435/5 |
| 2004/0229231 A1 | 11/2004 | Frudakis et al. | |
| 2004/0241730 A1 | 12/2004 | Yakhini et al. | |
| 2005/0039110 A1 | 2/2005 | De La Vega et al. | |
| 2005/0191731 A1 | 9/2005 | Judson et al. | |
| 2006/0003354 A1 | 1/2006 | Krantz et al. | |
| 2006/0046256 A1 | 3/2006 | Halldorsson et al. | |
| 2006/0100872 A1 | 5/2006 | Yokoi | |
| 2006/0161460 A1 | 7/2006 | Smitherman et al. | |
| 2006/0166224 A1 | 7/2006 | Norviel | |
| 2006/0257888 A1 | 11/2006 | Zabeau et al. | |
| 2007/0037182 A1 | 2/2007 | Gaskin et al. | |
| 2007/0178500 A1 | 8/2007 | Martin et al. | |
| 2007/0250809 A1 | 10/2007 | Kennedy et al. | |
| 2008/0004848 A1 | 1/2008 | Avey | |
| 2008/0081331 A1 | 4/2008 | Myres et al. | |
| 2008/0131887 A1 | 6/2008 | Stephen et al. | |
| 2008/0270366 A1 * | 10/2008 | Frank | G06F 16/9537 |
| 2009/0099789 A1 | 4/2009 | Stephen et al. | |
| 2009/0119083 A1 | 5/2009 | Avey et al. | |
| 2009/0182579 A1 | 7/2009 | Liu | |
| 2009/0198519 A1 | 8/2009 | McNamar | |
| 2009/0299645 A1 | 12/2009 | Colby et al. | |
| 2010/0042438 A1 | 2/2010 | Moore et al. | |
| 2010/0070455 A1 | 3/2010 | Halperin et al. | |
| 2010/0145981 A1 | 6/2010 | Wojcicki et al. | |
| 2010/0191513 A1 | 7/2010 | Listgarten et al. | |
| 2011/0130337 A1 | 6/2011 | Eriksson et al. | |
| 2012/0270794 A1 | 10/2012 | Eriksson et al. | |
| 2012/0301864 A1 * | 11/2012 | Bagchi | G09B 7/02 434/362 |
| 2013/0085728 A1 | 4/2013 | Tang et al. | |
| 2013/0345988 A1 | 12/2013 | Avey et al. | |
| 2014/0006433 A1 | 1/2014 | Hon et al. | |
| 2014/0045705 A1 | 2/2014 | Bustamante et al. | |
| 2014/0067280 A1 | 3/2014 | Vockley et al. | |
| 2014/0067355 A1 | 3/2014 | Noto et al. | |
| 2016/0026755 A1 | 1/2016 | Byrnes et al. | |
| 2016/0103950 A1 | 4/2016 | Myres et al. | |
| 2016/0171155 A1 | 6/2016 | Do et al. | |
| 2016/0277408 A1 | 9/2016 | Hawthorne et al. | |
| 2016/0350479 A1 | 12/2016 | Han et al. | |
| 2017/0011042 A1 | 1/2017 | Kermany et al. | |
| 2017/0017752 A1 | 1/2017 | Noto et al. | |
| 2017/0220738 A1 | 8/2017 | Barber et al. | |
| 2017/0228498 A1 | 8/2017 | Hon et al. | |
| 2017/0277827 A1 | 9/2017 | Granka et al. | |
| 2017/0277828 A1 | 9/2017 | Avey et al. | |
| 2017/0329866 A1 | 11/2017 | Macpherson | |
| 2017/0329891 A1 | 11/2017 | Macpherson et al. | |
| 2017/0329899 A1 | 11/2017 | Bryc et al. | |
| 2017/0329901 A1 | 11/2017 | Chowdry et al. | |
| 2017/0329902 A1 | 11/2017 | Bryc et al. | |
| 2017/0329904 A1 | 11/2017 | Naughton et al. | |
| 2017/0329915 A1 | 11/2017 | Kittredge et al. | |
| 2017/0329924 A1 | 11/2017 | Macpherson et al. | |
| 2017/0330358 A1 | 11/2017 | Macpherson et al. | |
| 2019/0114219 A1 | 4/2019 | Do et al. | |
| 2019/0139623 A1 | 5/2019 | Bryc et al. | |

OTHER PUBLICATIONS

U.S. Office Action dated Aug. 12, 2015 issued in U.S. Appl. No. 13/800,683.
U.S. Notice of Allowance dated Jan. 20, 2016 issued in U.S. Appl. No. 13/800,683.
U.S. Notice of Allowance dated May 3, 2016 issued in U.S. Appl. No. 13/800,683.
U.S. Office Action dated Jan. 23, 2018 issued in U.S. Appl. No. 15/181,083.
U.S. Notice of Allowance dated Aug. 14, 2018 issued in U.S. Appl. No. 15/181,083.
U.S. Notice of Allowance dated Nov. 15, 2018 issued in U.S. Appl. No. 15/181,083.
U.S. Office Action dated Jan. 29, 2015 issued in U.S. Appl. No. 13/801,056.
U.S. Notice of Allowance dated May 18, 2015 issued in U.S. Appl. No. 13/801,056.
U.S. Notice of Allowance dated Aug. 12, 2015 issued in U.S. Appl. No. 13/801,056.

(56) References Cited

OTHER PUBLICATIONS

U.S. Office Action dated Sep. 25, 2018 issued in U.S. Appl. No. 14/938,111.
U.S. Notice of Allowance dated Apr. 29, 2019 issued in U.S. Appl. No. 14/938,111.
U.S. Office Action dated Jun. 24, 2019 issued in U.S. Appl. No. 14/938,111.
U.S. Notice of Allowance dated Feb. 4, 2015 issued in U.S. Appl. No. 13/801,552.
U.S. Office Action dated Mar. 16, 2015 issued in U.S. Appl. No. 13/801,552.
U.S. Notice of Allowance dated Jun. 26, 2015 issued in U.S. Appl. No. 13/801,552.
U.S. Notice of Allowance dated Aug. 12, 2015 issued in U.S. Appl. No. 13/801,552.
U.S. Office Action dated Jul. 8, 2015 issued in U.S. Appl. No. 13/801,386.
U.S. Final Office Action dated Jan. 11, 2016 issued in U.S. Appl. No. 13/801,386.
U.S. Office Action dated Oct. 27, 2016 issued in U.S. Appl. No. 13/801,386.
U.S. Notice of Allowance dated Jul. 24, 2017 issued in U.S. Appl. No. 13/801,386.
U.S. Office Action dated Sep. 30, 2015 issued in U.S. Appl. No. 13/801,653.
U.S. Final Office Action dated May 31, 2016 issued in U.S. Appl. No. 13/801,653.
U.S. Office Action dated Apr. 19, 2017 issued in U.S. Appl. No. 13/801,653.
U.S. Notice of Allowance dated Dec. 28, 2017 issued in U.S. Appl. No. 13/801,653.
U.S. Office Action dated Feb. 9, 2018 issued in U.S. Appl. No. 14/924,552.
U.S. Final Office Action dated Sep. 4, 2018 issued in U.S. Appl. No. 14/924,552.
U.S. Office Action dated Jan. 30, 2018 issued in U.S. Appl. No. 14/924,562.
U.S. Final Office Action dated Sep. 13, 2018 issued in U.S. Appl. No. 14/924,562.
U.S. Office Action dated Jun. 5, 2019 issued in U.S. Appl. No. 14/924,562.
23andMeBlog [webpage] "New Feature: Ancestry Painting," by 23andMe, Ancestry, published online Mar. 25, 2008, pp. 1. [retrieved May 23, 2018] <URL:https://blog.23andme.com/23andme-and-you/new-feature-ancestry-painting/>.
Alexander, et al., "Fast model-based estimation of ancestry in unrelated Individuals," Genome Research, 2009, 19(9), Cold Spring Harbor Laboratory Press, ISSN 1088-9051/09, pp. 1655-1664.
Assareh, A., et al., "Interaction Trees: Optimizing Ensembles of Decision Trees for Gene-Gene Interaction Detections," 2012 11th International Conference on Machine Learning and Applications, vol. 1, Dec. 2012, pp. 616-621. <doi:10.1109/ICMLA.2012.114>.
Bettinger, B., [webpage] "AncestryDNA Launches New Ethnicity Estimate," The Genetic Genealogist (Internet Blog), published online Sep. 12, 2013, pp. 1-4. [retrieved May 23, 2018] <URL:https://thegeneticgenealogist.com/2013/09/12/ancestrydna-launches-new-ethnicity-estimate/>.
Bettinger, B., [webpage] "AncestryDNA Officially Launches," The Genetic Genealogist (Internet Blog), published online May 3, 2012, pp. 1-2. [retrieved May 23, 2018] <URL:https://thegeneticgenealogist.com/2012/05/03/ancestrydna-officially-launches/>.
Bettinger, B., [webpage] "The Monday Morning DNA Testing Company Review â€AncestryByDNA," The Genetic Genealogist (Internet Blog), published Feb. 26, 2007, p. 1. [retrieved May 23, 2018] <URL:https://thegeneticgenealogist.com/2007/02/26/the-monday-morning-dna-testing-company-review-%E2%80%93-ancestrybydna/>.
Bohringer, S., et al., "A Software Package for Drawing Ideograms Automatically," Online J Bioinformatics, vol. 1, 2002, pp. 51-61.

Brion, M., et al., "Introduction of a Single Nucleodite Polymorphism-Based Major Y-Chromosome Haplogroup Typing Kit Suitable for Predicting the Geographical Origin of Male Lineages," Electrophoresis, vol. 26, 2005, pp. 4411-4420.
Browning, S.R., et al., "Haplotype phasing: existing methods and new developments," Nature Reviews | Genetics, vol. 12, Oct. 2011, pp. 703-714. <doi:10.1038/nrg3054> [URL: http://www.nature.com/reviews/genetics].
Browning, et al., "Rapid and Accurate Haplotype Phasing and Missing-Data Inference for Whole-Genome Association Studies by Use of Localized Haplotype Clustering," The American Journal of Human Genetics, vol. 81, Nov. 2007, pp. 1084-1097.
Bryc, et al., "The Genetic Ancestry of African Americans, Latinos, and European Americans across the United States," The American Journal of Human Genetics, vol. 96, Jan. 8, 2015, pp. 37-53.
Burroughs et al., "Analysis of Distributed Intrusion Detection Systems Using Bayesian Methods," Performance, Computing and Communications Conference, 2002, 21st IEEE International. IEEE, 2002, pp. 329-334.
Byrne, J. et al., "The simulation life-cycle: supporting the data collection and representaion phase," Simulation Conference (WSC), 2014 Wincer, pp. 2738-2749.
Cao, et al., "Design of Reliable System Based on Dynamic Bayesian Networks and Genetic Algorithm," Reliability and Maintainability Symposium (RAMS), 2012 Proceedings—Annual. IEEE, 2012.
Cardena, et al., "Assessment of the Relationship between Self-Declared Ethnicity, Mitochondrial Haplogroups and Genomic Ancestry in Brazilian Individuals," PLoS ONE, vol. 8, No. 4, Apr. 24, 2013, pp. 1-6.
Cavalli-Sforza, L., "The Human Genome Diversity Project: past, present and future," Nature Reviews, Genetics, vol. 6, Apr. 2005, pp. 333-340.
Churchhouse, et al., "Multiway Admixture Deconvolution Using Phased or Unphased Ancestral Panels," Wiley Periodical, Inc., Genetic Epidemiology, 2012, pp. 1-12.
Crawford, et al., "Evidence for substantial fine-scale variation in recombination rates across the human genome," Nature Genetics, vol. 36, No. 7, Jul. 2004, pp. 700-706.
De Francesco, L., et al., "Efficient Genotype Elimination Via Adaptive Allele Consolidation," IEEE/ACM Transactions on Computational Biology and Bioinformatics (TCBB), vol. 9, No. 4, Jul. 2012, pp. 1180-1189. <doi:10.1109/TCBB.2012.46>.
Dean, M., et al., "Polymorphic Admixture Typing in Human Ethnic Populations," American Journal of Human Genetics, vol. 55:4, 1994, pp. 788-808.
Delaneau, et al., "A Linear complexity phasing method for thousands of genomes," Nature Methods, vol. 9, No. 2, Feb. 2012, pp. 179-184.
Do et al., "A scalable pipeline for local ancestry inference using thousands of reference individuals (Abstract)," From Abstract/Session Information for Program No. 3386W; Session Title: Evolutionary and Population Genetics), ASHG, Aug. 2012.
Dodecad Project, [webpage] "Clusters Galore results, K=73 for Dodecad Project members (up to DOD581)" Dodecad Ancestry Project (Internet Blog), published Mar. 31, 2011, pp. 1-11. [retrieved May 23, 2018] <URL:http://dodecad.blogspot.com/2011/03/>.
Dr. D., [webpage] "Population Finder Traces Deep Ancestry," Dr. D Digs Up Ancestors (Internet Blog), DNA Testing, published online Apr. 9, 2011, p. 1. [retrieved May 23, 2018] <URL:http://blog.ddowell.com/2011/04/population-finder-traces-deep-ancestry.html>.
Durand, et al., "Ancestry Composition: A Novel, Efficient Pipeline for Ancestry Deconvolution," bioRxiv preprint first posted online Oct. 18, 2014, http://dx.doi.org/10.1101/010512, pp. 1-16.
Falush, et al., "Inference of Population Structure Using Multilocus Genotype Data: Linked Loci and Correlated Allele Frequencies," Genetics, 164(4), Aug. 2003, pp. 1567-1587.
Feng et al., "Mining Multiple Temporal Patterns of Complex Dynamic Data Systems," Computational Intelligence and Data Mining, IEEE, 2009, 7 pages.
Fuchsberger, et al., "Minimac2: faster genotype imputation," Bioinformatics, vol. 31, No. 5, Oct. 22, 2014, pp. 782-784. <doi:10.1093/bioinformatics/btu704>.

(56) References Cited

OTHER PUBLICATIONS

Goldberg, et al., "Autosomal Admixture Levels are Informative About Sex Bias in Admixed Populations," Genetics, Nov. 2014, vol. 198, pp. 1209-1229.
Gusev, et al., "Whole population, genome-wide mapping of hidden relatedness," Genome Research, vol. 19, 2009, pp. 318-326.
Gravel, S., "Population Genetics Models of Local Ancestry," Genetics, Jun. 2012, 191(2), pp. 607-619.
Green, et al., "A Draft Sequence of the Neandertal Genome," Science, Author Manuscript, available online in PMC Nov. 8, 2016 pp. 1-36.
Green, et al., "A Draft Sequence of the Neandertal Genome," Science, vol. 328, May 7, 2010, pp. 710-722.
Gu et al., "Phenotypic Selection for Dormancy Introduced a Set of Adaptive Haplotypes from Weedy Into Cultivated Rice," Genetics Society of America, vol. 171, Oct. 2005, pp. 695-704.
Halder, I., et al., "A panel of Ancestry Informative Markers for Estimating Individual Biogeographical Ancestry and Admixture from four Continents: Utility and Applications" Human Mutation, vol. 29:5, 2008, pp. 648-658.
He, et al., "Multiple Linear Regression for Index SNP Selection on Unphased Genotypes," Engineering in Medicine and Biology Society, EMBS Annual International Conference of the IEEE, Aug. 30-Sep. 3, 2006, pp. 5759-5762.
He, D. et al., "IPEDX: An Exact Algorithm for Pedigree Reconstruction Using Genotype Data," 2013 IEEE International Conference on Bioinformatics and Biomedicine, 2013, pp. 517-520. <doi:10.1109/BIBM.2013.6732549>.
Hellenthal, et al. "A Genetic Atlas of Human Admixture History," Science, vol. 343, Feb. 14, 2014, pp. 747-751.
Hill, et al. "Identification of Pedigree Relationship from Genome Sharing," G3: Gene | Genomes | Genetics, vol. 3, Sep. 2013, pp. 1553-1571.
Howie, et al., "A Flexible and Accurate Genotype Imputation Method for the Next Generation of Genome-Wide Association Studies," PLoS Genetics, vol. 5, No. 6, Jun. 2009, pp. 1-15. -.
Howie, et al., "Fast and accurate genotype imputation in genome-wide association studies through pre-phasing," Nature Genetics, vol. 44, No. 8, Aug. 2012, pp. 955-960.
Huff, et al., "Maximum-Likelihood Estimation of Recent Shared Ancestry (ERSA)," Genome Research,2011, ISSN 1088-9051/11, 21(5), pp. 768-774.
Jia, Jing et al. "Developing a novel panel of genome-wide ancestry informative markers for bio-geographical ancestry estimates," Forensic Science International: Genetics, vol. 8 (2014) pp. 187-194.
Karakuzu, A., et al., "Assessment of In-Vivo Skeletal Muscle Mechanics During Joint Motion Using Multimodal Magnetic Resonance Imaging Based Approaches," Biomedical Engineering Meeting (BIYOMUT), 2014 18th National, pp. 1-4.
Kennedy, et al., "Visual Cleaning of Genotype Data," 2013 IEEE Symposium on Biological Data Visualization (BioVis), Atlanta, Ga., Oct. 2013, pp. 105-112. <doi:10.1109/BioVis.2013.6664353>.
Kerchner, [webpage] "DNAPrint Test Results—East Asian vs Native American Minority Admixture Detection," PA Deutsch Ethnic Group DNA Project, created Jun. 26, 2004, updated May 27, 2005, pp. 1-9. [retrieved May 23, 2018] <URL:http://www.kerchner.com/dnaprinteaysna.htm>.
Kidd, et al. "Population Genetic Inference from Personal Genome Data: Impact of Ancestry and Admixture on Human Genomic Variation," The American Journal of Human Genetics, vol. 91, Oct. 5, 2012, pp. 660-671.
Kirkpatrick, B., et al. "Perfect Phylogeny Problems with Missing Values," IEEE/ACM Transactions on Computational Biology and Bioinformatics (TCBB), vol. 11, No. 5, Sep./Oct. 2014, pp. 928-941. <doi:10.1109/TCBB.2014.2316005>.
Kraak, M-J, "Visualising Spatial Distributions," Geographical Information Systems: Principles, Techniques, Applications and Management, New York, John Wiley and Sons, 1999, pp. 157-173.
Lawson, et al., "Inference of Population Structure using Dense Haplotype Data," PLoS Genetics, vol. 8, No. 1, Jan. 2012, pp. 1-16.
Lazaridis et al., "Ancient Human Genomes Suggest Three Ancestral Populations for Present-Day Europeans," Nature, Author Manuscript available online in PMC Mar. 18, 2015 pp. 1-33.
Lazaridis et al., "Ancient Human Genomes Suggest Three Ancestral Populations for Present-Day Europeans," Nature, vol. 513, Sep. 18, 2014, doi:10.1038/nature 13673, pp. 409-413.
Lei, X. et al., "Cloud-Assisted Privacy-Preserving Genetic Paternity Test," 2015 IEEE/CIC International Conference on Communications in China (ICCC), Apr. 7, 2016, pp. 1-6. <doi:10.1109/ICCChina.2015.7448655>.
Lee, et al., "Comparing genetic ancestry and self-reported race/ethnicity in a multiethnic population in New York City," Journal of Genetics, vol. 89, No. 4, Dec. 2010, pp. 417-423.
Li, et al., "Modeling Linkage Disequilibrium and Identifying Recombination Hotspots Using Single-Nucleotide Polymorphism Data," Genetics Society of America, vol. 165, Dec. 2003, pp. 2213-2233.
Li, et al. "Worldwide Human Relationships Inferred from Genome-Wide Patterns of Variation," Science, vol. 319, Feb. 22, 2008, pp. 1100-1104.
Li, X., et al., "Integrating Phenotype-Genotype Data for Prioritization of Candidate Symptom Genes," 2013 IEEE International Conference on Bioinformatics and Biomedicine, Dec. 2013, pp. 279-280. <doi:10.1109/BIBM.2013.6732693>.
Liang et al., "The Lengths of Admixture Tracts," Genetics, vol. 197, Jul. 2014, pp. 953-967. <doi:10.1534/genetics.114.162362>.
Liang et al., "A Deterministic Sequential Monte Carlo Method for Haplotype Inference," IEEE Journal of Selected Topics in Signal Processing, vol. 2, No. 3, Jun. 2008, pp. 322-331.
Lin et al. "Polyphase Speech Recognition," Acoustics, Speech and Signal Processing, IEEE International Conference on 2008, IEEE, 2008, 4 pages.
Lipson, et al., "Reconstructing Austronesian population history in Island Southeast Asia," Nature Communications, 5:4689, DOI: 10.1038/ncomms5689, 2014, pp. 1-7.
Loh, et al., "Inferring Admixture Histories of Human Populations Using Linkage Disequilibrium," Genetics, 193(4), Apr. 2013, pp. 1233-1254.
Mahieu, L., [webpage] "My (free) Ancestry.com DNA results—a comparison to FamilyTreeDNA," Genejourneys (Internet Blog), published online Mar. 6, 2012, pp. 1-3. [retrieved May 23, 2018] <URL:https://genejourneys.com/2012/03/06/my-free-ancestry-com-dna-results-a-comparison-to-familytreedna/>.
Maples, et al. "RFMix: A Discriminitve Modeling Approach for Rapid and Robust Local-Ancestry Inference," American Journal of Human Genetics (AJHG) vol. 93, No. 2, Aug. 8, 2013, pp. 278-288. [retreived Nov. 12, 2015] <URL: https://doi.org/10.1016/j.ajhg.2013.06.020>.
Mersha, Tesfaye et al. "Self-reported race/ethnicity in the age of genomic research: its potential impact on understanding health disparities," Human Genomics, vol. 9, No. 1 (2015) pp. 1-15.
Montinaro, Francesco et al. "Unraveling the hidden ancestry of American admixed populations," Nature Communications, Mar. 24, 2015, pp. 1-7. <doi:10.1038/ncomms7596>.
Moore, C., [webpage] "LivingSocial's AncestrybyDNA Offer is Not the AncestryDNA Test!" Your Genetic Genealogist (Internet Blog), published online Sep. 18, 2012, pp. 1-2. [retrieved May 23, 2018] <URL:http://www.yourgeneticgenealogist.com/2012/09/livingsocials-ancestrybydna-offer-is.html>.
Moore, C., [webpage] "New Information on Ancestry.com's AncestryDNA Product," Your Genetic Geneologist (Internet Blog), published online Mar. 30, 2012, pp. 1-3. [retrieved May 23, 2018] <URL:http://www.yourgeneticgenealogist.com/2012/03/new-information-on-ancestrycoms.html>.
Moreno-Estrada, et al., "Reconstructing the Population Genetic History of the Caribbean," PLoS Genetics, 9(11), e1003925, Nov. 14, 2013, pp. 1-19.
Nievergeit, Caroline, et al., "Inference of human continental origin and admixture proportions using a highly discriminative ancestry informative 41-SNP panel," Investigative Genetics, vol. 4, No. 13 (2013), pp. 1-16.

(56) References Cited

OTHER PUBLICATIONS

Novembre, et al. "Recent advances in the study of fine-scale population structure in humans," Current Opinion in Genetics & Development, vol. 41 (2016), pp. 98-105. <URL:http://dx.doi.org/10.1016/>.

Omberg, L., et al., "Inferring Genome-Wide Patterns of Admixture in Qataris Using Fifty-Five Ancestral Populations," BMC Genetics, 2012, ISSN 1471-2156, BioMed Central, Ltd., 18 pages.

Pasaniuc et al., "Highly Scalable Genotype Phasing by Entropy Minimization," Engineering in Medicine and Biology Society, 2006, EMBS'06, 28th Annual International Conference of the IEEE, 2006, 5 pages.

Pasaniuc, et al., "Inference of locus-specific ancestry in closely related populations," Bioinformatics, vol. 25, 2009, pp. i213-i221.

Patterson, et al., "Methods for High-Density Admixture Mapping of Disease Genes," AJHG, vol. 74, No. 5, May 2004, pp. 1-33.

Patterson, et al., "Population Structure and Eigenanalysis," PLoS Genetics, vol. 2, No. 12, e190, Dec. 2006, pp. 2074-2093.

Phelps, C.I., et al. "Signal Classification by probablistic reasoning," Radio and Wireless Symposium (RWS), 2013 IEEE Year: 2013, pp. 154-156.

Phillips, et al., "Inferring Ancestral Origin Using a Single Multiplex Assay of Ancestry-Informative Marker SNPs," Forensic Science International, Genetics, vol. 1, 2007, pp. 273-280.

Pirola, et al., "A Fast and Practical Approach to Genotype Phasing and Imputation on a Pedigree with Erroneous and Incomplete Information," IEEE/ACM Transactions on Computational Biology and Bioinformatics, vol. 9, No. 6. Nov./Dec. 2012, pp. 1582-1594.

Pool, et al., "Inference of Historical Changes in Migration Rate From the Lengths of Migrant Tracts," Genetics, 181(2), Feb. 2009, pp. 711-719.

Porras-Hurtado, et al., "An overview of STRUCTURE: applications, parameter settings, and supporting software," Frontiers in Genetics, vol. 4, No. 96, May 29, 2013, pp. 1-13.

Price, et al. "Sensitive Detection of Chromosomal Segments of Distinct Ancestry in Admixed Populations," PLoS Genetics, vol. 5, No. 6, Jun. 19, 2009 (e1000519) pp. 1-18.

Pritchard, et al., "Association Mapping in Structured Populations," Am. J. Hum. Genet., vol. 67, 2000, pp. 170-181.

Pritchard, et al., "Inference of Population Structure Using Multilocus Genotype Data," Genetics Society of America, vol. 155, Jun. 2000, pp. 945-959.

Purcell, et al., "PLINK: A Tool Set for Whole-Genome Association and Population-Based Linkage Analysis," The American Journal of Human Genetics, vol. 81, Sep. 2007, pp. 559-575.

Rabiner, L., "A Tutorial on Hidden Markov Models and Selected Applications in Speech Recognition," Proceedings of the IEEE, vol. 77, No. 2, Feb. 1989, pp. 257-286.

Royal, et al. "Inferring Genetic Ancestry: Opportunities, Challenges, and Implications," The American Journal of Human Genetics, vol. 86, May 14, 2010, pp. 661-673.

Sankararaman, et al., "Estimating Local Ancestry in Admixed Populations," The American Journal of Human Genetics, vol. 82, Feb. 2008, pp. 290-303.

Sankararaman, et al., "On the inference of ancestries in admixed populations," Genome Research, Mar. 2008, vol. 18, pp. 668-675.

Sengupta, et al., "Polarity and Temporality of High-Resolution Y-Chromosome Distributions in India Identify Both Indigenous and Exogenous Expansions and Reveal Minor Genetic Influence of Central Asian Pastoralists," The American Journal of Human Genetics, vol. 78, Feb. 2006, pp. 202-221.

Scheet, et al., "A Fast and Flexible Statistical Model for Large-Scale Population Genotype Data: Applications to Inferring Missing Genotypes and Haplotypic Phase," The American Journal of Human Genetics, vol. 78, Apr. 2006, pp. 629-644.

Shriver, et al. "Ethnic-Affiliation Estimation by Use of Population-Specific DNA Markers," American Journal of Human Genetics, vol. 60, 1997, pp. 957-964.

Shriver, et al., "Genetic ancestry and the Search for Personalized Genetic Histories," Nature Reviews Genetics, vol. 5, Aug. 2004, pp. 611-618.

Sohn, et al. "Robust Estimation of Local Genetic Ancestry in Admixed Populations Using a Nonparametric Bayesian Approach," Genetics, vol. 191, Aug. 2012, pp. 1295-1308.

Stephens, et al., "Accounting for Decay of Linkage Disequilibrium in Haplotype Inference and Missing-Data Imputation," Am. J. Hum. Genet., vol. 76, 2005, pp. 449-462.

Stephens, et al., "A Comparison of Bayesian Methods for Haplotype Reconstruction from Population Genotype Data," Am. J. Hum. Genet., vol. 73, 2003, pp. 1162-1169.

Stephens, et al., "A New Statistical Method for Haplotype Reconstruction from Population Data," Am. J. Hum. Genet., vol. 68, 2001, pp. 978-989.

Sundquist, et al., "Effect of genetic divergence in identifying ancestral origin using HAPAA," Genome Research, vol. 18, Mar. 2008, pp. 676-682.

Tang, et al., "Reconstructing Genetic Ancestry Blocks in Admixed Individuals," The American Journal of Human Genetics, vol. 79, Jul. 2006, pp. 1-12.

Tang, et al., "Estimation of Individual Admixture: Analytical and Study Design Consideration," Genetic Epidemiology, vol. 28, 2005, pp. 289-301.

The International HapMap Consortium, "A haplotype map of the human genome," Nature, vol. 437, Oct. 27, 2005, pp. 1299-1320. <doi:10.1038/nature04226>.

The International HapMap Consortium, "A second generation human haplotype map of over 3.1 million SNPs," Nature, vol. 449, Oct. 18, 2007, pp. 851-860. <doi:10.1038/nature06258>.

Thiele, et al., "HaploPainter: a Tool for Drawing Pedigrees with Complex Haplotypes," Bioinformatics, vol. 21:8, 2005, pp. 1730-1732.

Uddin, et al., "Variability of Haplotype Phase and Its Effect on Genetic Analysis," Electrical and Computer Engineering, 2008, CCECE 2008, Canadian Conference on, IEEE, 2008, pp. 000596-000600.

Underhill, et al., "Use of Y Chromosome and Mitochondrial DNA Population Structure in Tracing Human Migrations," Annu. Rev. Genet., vol. 41, 2007, pp. 539-564.

Vanitha, et al., "Implementation of an Integrated FPGA Based Automatic Test Equipment and Test Generation for Digital Circuits," Information Communication and Embedded Systems (ICICES), 2013 International Conference on. IEEE, 2013.

Yang, et al., "Examination of Ancestry and Ethnic Affiliation Using Highly Informative Diallelic DNA Markers: Application to Diverse and Admixed Populations and Implications for Clinical Epidemiology and Forensic Medicine," Human Genetics, vol. 118, 2005, pp. 382-392.

Yoon, Byung-Jun, "Hidden Markov Models and their Applications in Biological Sequence Analysis," Current Genomics, vol. 10, 2009, pp. 402-415.

U.S. Appl. No. 15/181,088, filed Jun. 13, 2016, Do, et al.
U.S. Appl. No. 16/044,364, filed Jul. 24, 2018, Do, et al.
U.S. Appl. No. 16/282,221, filed Feb. 21, 2019, Do, et al.
U.S. Appl. No. 12/381,992, filed Mar. 18, 2009, Macpherson et al.
U.S. Appl. No. 16/226,116, filed Dec. 19, 2018, Macpherson et al.
U.S. Appl. No. 16/219,597, filed Dec. 13, 2018, Bryc et al.
U.S. Office Action dated Aug. 2, 2011, issued in U.S. Appl. No. 12/381,992.
U.S. Final Office Action dated Dec. 20, 2011, issued in U.S. Appl. No. 12/381,992.
U.S. Office Action dated Aug. 6, 2013, issued in U.S. Appl. No. 12/381,992.
U.S. Final Office Action dated Dec. 27, 2013, issued in U.S. Appl. No. 12/381,992.
U.S. Office Action dated Aug. 7, 2014, issued in U.S. Appl. No. 12/381,992.
U.S. Final Office Action dated Dec. 22, 2014, issued in U.S. Appl. No. 12/381,992.
U.S. Office Action dated May 22, 2015, issued in U.S. Appl. No. 12/381,992.

(56) References Cited

OTHER PUBLICATIONS

U.S. Final Office Action dated Nov. 3, 2015, issued in U.S. Appl. No. 12/381,992.
U.S. Office Action dated Mar. 16, 2016, issued in U.S. Appl. No. 12/381,992.
U.S. Office Action dated Feb. 11, 2019, issued in U.S. Appl. No. 16/044,364.
U.S. Notice of Allowance dated Jan. 9, 2020 issued in U.S. Appl. No. 14/938,111.
U.S. Final Office Action dated Jan. 8, 2020 issued in U.S. Appl. No. 14/924,562.
U.S. Office Action dated Jun. 25, 2019 issued in U.S. Appl. No. 15/181,088.
U.S. Notice of Allowance dated Nov. 12, 2019, issued in U.S. Appl. No. 16/044,364.
U.S. Appl. No. 16/915,868, filed Jun. 29, 2020, Do et al.

* cited by examiner

|      | Afri | NAme | Ashk | EAsi | Balk | EEur | MEas | BIsl | Scan | Finl | Ocea | SAsi | Sard | Ital | Iber | Gree | Arab | wEur |
|------|------|------|------|------|------|------|------|------|------|------|------|------|------|------|------|------|------|------|
| Afri | 0.82 | 0.01 | 0.01 | 0.03 | 0.01 | 0.01 | 0.01 | 0.01 | 0.00 | 0.01 | 0.01 | 0.02 | 0.01 | 0.01 | 0.01 | 0.01 | 0.01 | 0.01 |
| NAme | 0.01 | 0.71 | 0.01 | 0.10 | 0.01 | 0.01 | 0.01 | 0.01 | 0.01 | 0.02 | 0.04 | 0.02 | 0.02 | 0.01 | 0.01 | 0.01 | 0.03 | 0.01 |
| Ashk | 0.01 | 0.03 | 0.40 | 0.03 | 0.04 | 0.03 | 0.04 | 0.02 | 0.03 | 0.05 | 0.03 | 0.03 | 0.10 | 0.02 | 0.03 | 0.05 | 0.05 | 0.02 |
| EAsi | 0.01 | 0.10 | 0.02 | 0.57 | 0.01 | 0.01 | 0.01 | 0.01 | 0.01 | 0.03 | 0.07 | 0.05 | 0.02 | 0.01 | 0.01 | 0.02 | 0.02 | 0.01 |
| Balk | 0.01 | 0.04 | 0.06 | 0.04 | 0.08 | 0.08 | 0.05 | 0.05 | 0.06 | 0.08 | 0.03 | 0.04 | 0.10 | 0.05 | 0.04 | 0.08 | 0.05 | 0.04 |
| EEur | 0.01 | 0.05 | 0.06 | 0.04 | 0.07 | 0.12 | 0.04 | 0.05 | 0.07 | 0.11 | 0.03 | 0.04 | 0.09 | 0.03 | 0.04 | 0.07 | 0.04 | 0.04 |
| MEas | 0.02 | 0.04 | 0.08 | 0.06 | 0.05 | 0.04 | 0.10 | 0.04 | 0.04 | 0.05 | 0.03 | 0.09 | 0.09 | 0.05 | 0.04 | 0.07 | 0.07 | 0.03 |
| BIsl | 0.01 | 0.04 | 0.05 | 0.03 | 0.05 | 0.06 | 0.03 | 0.10 | 0.10 | 0.10 | 0.03 | 0.04 | 0.11 | 0.04 | 0.06 | 0.06 | 0.06 | 0.05 |
| Scan | 0.01 | 0.04 | 0.05 | 0.03 | 0.05 | 0.06 | 0.04 | 0.09 | 0.12 | 0.12 | 0.03 | 0.03 | 0.10 | 0.03 | 0.03 | 0.06 | 0.04 | 0.05 |
| Finl | 0.00 | 0.05 | 0.04 | 0.04 | 0.04 | 0.06 | 0.03 | 0.08 | 0.12 | 0.31 | 0.03 | 0.03 | 0.09 | 0.02 | 0.03 | 0.05 | 0.03 | 0.03 |
| Ocea | 0.04 | 0.04 | 0.02 | 0.19 | 0.01 | 0.01 | 0.02 | 0.02 | 0.01 | 0.02 | 0.47 | 0.07 | 0.02 | 0.02 | 0.01 | 0.01 | 0.02 | 0.01 |
| SAsi | 0.02 | 0.05 | 0.05 | 0.11 | 0.04 | 0.04 | 0.06 | 0.04 | 0.03 | 0.05 | 0.05 | 0.23 | 0.06 | 0.03 | 0.03 | 0.05 | 0.04 | 0.02 |
| Sard | 0.01 | 0.03 | 0.06 | 0.04 | 0.05 | 0.05 | 0.05 | 0.06 | 0.05 | 0.06 | 0.03 | 0.04 | 0.21 | 0.05 | 0.06 | 0.07 | 0.06 | 0.04 |
| Ital | 0.02 | 0.04 | 0.07 | 0.04 | 0.05 | 0.05 | 0.06 | 0.06 | 0.05 | 0.07 | 0.03 | 0.05 | 0.11 | 0.06 | 0.06 | 0.07 | 0.07 | 0.04 |
| Iber | 0.02 | 0.04 | 0.06 | 0.06 | 0.05 | 0.05 | 0.06 | 0.07 | 0.06 | 0.08 | 0.03 | 0.04 | 0.12 | 0.05 | 0.09 | 0.06 | 0.06 | 0.05 |
| Gree | 0.02 | 0.03 | 0.07 | 0.07 | 0.06 | 0.06 | 0.06 | 0.05 | 0.05 | 0.06 | 0.03 | 0.05 | 0.11 | 0.06 | 0.05 | 0.09 | 0.06 | 0.04 |
| Arab | 0.07 | 0.03 | 0.07 | 0.07 | 0.04 | 0.03 | 0.06 | 0.04 | 0.03 | 0.04 | 0.03 | 0.06 | 0.08 | 0.05 | 0.04 | 0.06 | 0.19 | 0.03 |
| wEur | 0.01 | 0.04 | 0.06 | 0.03 | 0.05 | 0.06 | 0.04 | 0.08 | 0.09 | 0.10 | 0.03 | 0.04 | 0.11 | 0.04 | 0.06 | 0.06 | 0.04 | 0.06 |

FIG. 19

|  | BEFORE | | | | AFTER | | | |
| --- | --- | --- | --- | --- | --- | --- | --- | --- |
|  | unadmixed | | admixed | | unadmixed | | admixed | |
|  | recall | prec | recall | prec | recall | prec | recall | prec |
| African | 0.82 | 0.83 | 0.77 | 0.70 | 1.00 | 0.99 | 0.94 | 0.93 |
| Native American | 0.71 | 0.19 | 0.64 | 0.45 | 0.99 | 1.00 | 0.90 | 0.92 |
| Ashkenazi | 0.40 | 0.57 | 0.41 | 0.32 | 0.91 | 0.98 | 0.88 | 0.92 |
| East Asian | 0.57 | 0.68 | 0.53 | 0.36 | 1.00 | 0.99 | 0.88 | 0.86 |
| Balkans | 0.08 | 0.04 | 0.08 | 0.10 | 0.71 | 0.75 | 0.29 | 0.45 |
| Eastern Europe | 0.12 | 0.16 | 0.11 | 0.13 | 0.80 | 0.75 | 0.55 | 0.47 |
| Middle East | 0.10 | 0.08 | 0.10 | 0.10 | 0.89 | 0.78 | 0.55 | 0.47 |
| British Isles | 0.10 | 0.25 | 0.10 | 0.11 | 0.96 | 0.53 | 0.68 | 0.22 |
| Scandinavia | 0.12 | 0.12 | 0.12 | 0.13 | 0.60 | 0.62 | 0.35 | 0.51 |

ANCESTRY PAINTING WITH LOCAL ANCESTRY INFERENCE

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND OF THE INVENTION

Ancestry deconvolution refers to identifying the ancestral origin of chromosomal segments in individuals. Ancestry deconvolution in admixed individuals (i.e., individuals whose ancestors such as grandparents are from different regions) is straightforward when the ancestral populations considered are sufficiently distinct (e.g., one grandparent is from Europe and another from Asia). To date, however, existing approaches are typically ineffective at distinguishing between closely related populations (e.g., within Europe). Moreover, due to their computational complexity, most existing methods for ancestry deconvolution are unsuitable for application in large-scale settings, where the reference panels used contain thousands of individuals.

BRIEF DESCRIPTION OF THE DRAWINGS

Various embodiments of the invention are disclosed in the following detailed description and the accompanying drawings.

FIG. 19 is an example data table displaying the emission parameters.

FIG. 21 is a table comparing the predictive accuracies of ancestry assignments with and without error correction.

FIGS. 29-30 are diagrams illustrating embodiments of a chromosome-specific view.

DETAILED DESCRIPTION

Figure 1:
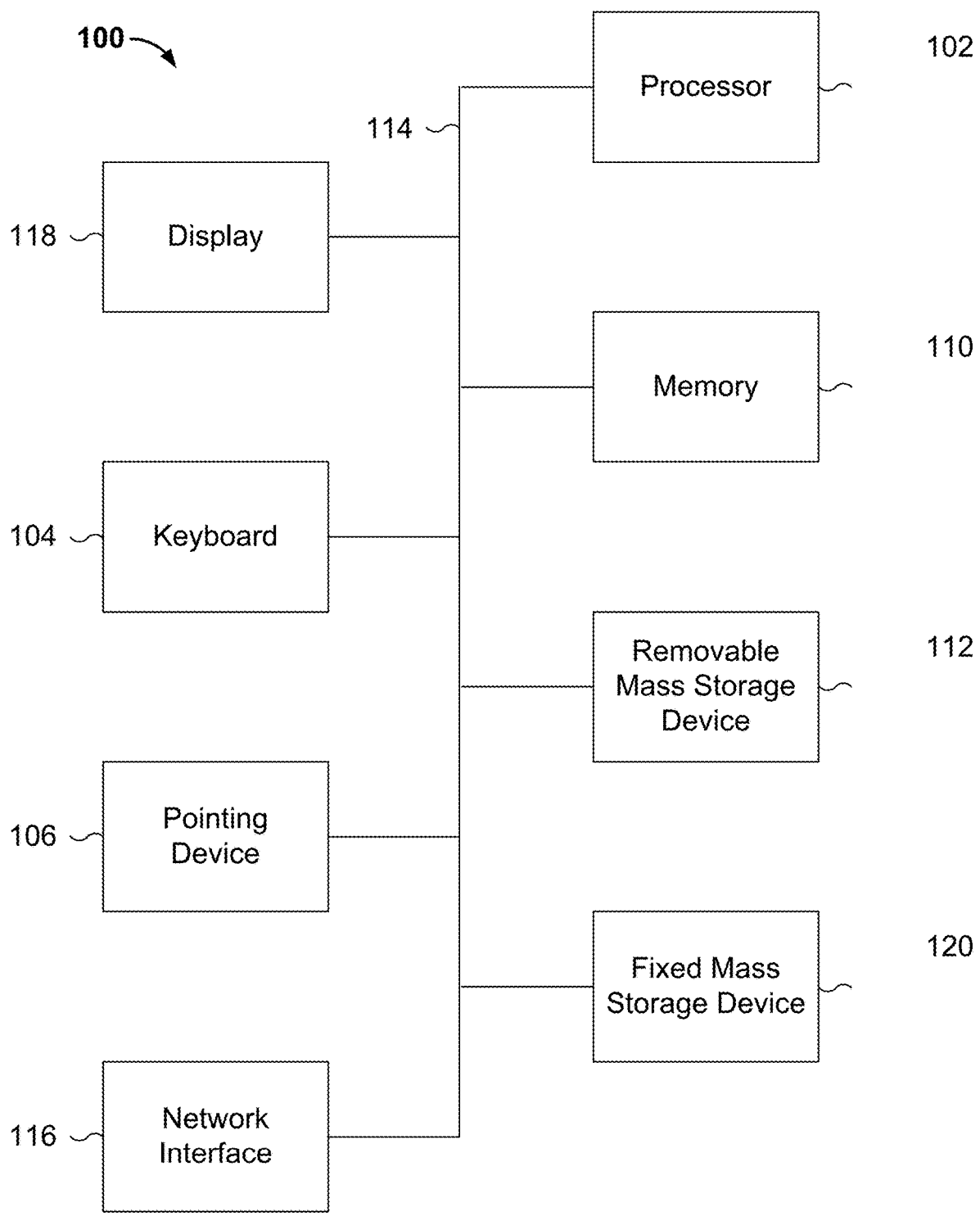
FIG. 1 is a functional diagram illustrating a programmed computer system for performing the pipelined ancestry prediction process in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment.

The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A pipelined ancestry deconvolution process to predict an individual's ancestry based on genetic information is disclosed. Unphased genotype data associated with the individual's chromosomes is received and phased to generate phased haplotype data. In some embodiments, dynamic programming that does not require the unphased genotype data to be included in the reference data is implemented to facilitate phasing. The phased data is divided into segments, which are classified as being associated with specific ancestries. The classification is performed using a learning machine in some embodiments. The classification output undergoes an error correction process to reduce noise and correct for any phasing errors (also referred to as switch errors) and/or correlated classification errors. The error corrected output is optionally recalibrated, and ancestry labels are optionally clustered according to a geographical hierarchy to be displayed to the user.

In some embodiments, genotype data comprising gene sequences and/or genetic markers is used to represent an individual's genome. Examples of such genetic markers include Single Nucleotide Polymorphisms (SNPs), which are points along the genome, each corresponding to two or more common variations; Short Tandem Repeats (STRs), which are repeated patterns of two or more repeated nucleotide sequences adjacent to each other; and Copy-Number Variants (CNVs), which include longer sequences of deoxyribonucleic acid (DNA) that could be present in varying numbers in different individuals. Although SNP-based genotype data is described extensively below for purposes of illustration, the technique is also applicable to other types of genotype data such as STRs and CNVs. As used herein, a haplotype refers to DNA on a single chromosome of a chromosome pair. Haplotype data representing a haplotype can be expressed as a set of markers (e.g., SNPs, STRs, CNVs, etc.) or a full DNA sequence set.

FIG. 1 is a functional diagram illustrating a programmed computer system for performing the pipelined ancestry prediction process in accordance with some embodiments. Computer system 100, which includes various subsystems as described below, includes at least one microprocessor subsystem (also referred to as a processor or a central processing unit (CPU)) 102. For example, processor 102 can be implemented by a single-chip processor or by multiple processors. In some embodiments, processor 102 is a general purpose digital processor that controls the operation of the computer system 100. Using instructions retrieved from memory 110, the processor 102 controls the reception and manipulation of input data, and the output and display of data on output devices (e.g., display 118). In some embodiments, processor 102 includes and/or is used to provide phasing, local classification, error correction, recalibration, and/or label clustering as described below.

Processor 102 is coupled bi-directionally with memory 110, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 102. Also as is well known in the art, primary storage typically includes basic operating instructions, program code, data, and objects used by the processor 102 to perform its functions (e.g., programmed instructions). For example, memory 110 can include any suitable computer-readable storage media, described below, depending on whether, for example, data access needs to be bi-directional or unidirectional. For example, processor 102 can also directly and very rapidly retrieve and store frequently needed data in a cache memory (not shown).

A removable mass storage device 112 provides additional data storage capacity for the computer system 100, and is coupled either bi-directionally (read/write) or uni-directionally (read only) to processor 102. For example, storage 112 can also include computer-readable media such as magnetic tape, flash memory, PC-CARDS, portable mass storage devices, holographic storage devices, and other storage devices. A fixed mass storage 120 can also, for example, provide additional data storage capacity. The most common example of mass storage 120 is a hard disk drive. Mass storage 112, 120 generally store additional programming instructions, data, and the like that typically are not in active use by the processor 102. It will be appreciated that the information retained within mass storage 112 and 120 can be incorporated, if needed, in standard fashion as part of memory 110 (e.g., RAM) as virtual memory.

In addition to providing processor 102 access to storage subsystems, bus 114 can also be used to provide access to other subsystems and devices. As shown, these can include a display monitor 118, a network interface 116, a keyboard 104, and a pointing device 106, as well as an auxiliary input/output device interface, a sound card, speakers, and other subsystems as needed. For example, the pointing device 106 can be a mouse, stylus, track ball, or tablet, and is useful for interacting with a graphical user interface.

The network interface 116 allows processor 102 to be coupled to another computer, computer network, or telecommunications network using a network connection as shown. For example, through the network interface 116, the processor 102 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 102 can be used to connect the computer system 100 to an external network and transfer data according to standard protocols. For example, various process embodiments disclosed herein can be executed on processor 102, or can be performed across a network such as the Internet, intranet networks, or local area networks, in conjunction with a remote processor that shares a portion of the processing. Additional mass storage devices (not shown) can also be connected to processor 102 through network interface 116.

An auxiliary I/O device interface (not shown) can be used in conjunction with computer system 100. The auxiliary I/O device interface can include general and customized interfaces that allow the processor 102 to send and, more typically, receive data from other devices such as microphones, touch-sensitive displays, transducer card readers, tape readers, voice or handwriting recognizers, biometrics readers, cameras, portable mass storage devices, and other computers.

In addition, various embodiments disclosed herein further relate to computer storage products with a computer readable medium that includes program code for performing various computer-implemented operations. The computer-readable medium is any data storage device that can store data which can thereafter be read by a computer system. Examples of computer-readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code, as produced, for example, by a compiler, or files containing higher level code (e.g., script) that can be executed using an interpreter.

The computer system shown in FIG. 1 is but an example of a computer system suitable for use with the various embodiments disclosed herein. Other computer systems suitable for such use can include additional or fewer subsystems. In addition, bus 114 is illustrative of any interconnection scheme serving to link the subsystems. Other computer architectures having different configurations of subsystems can also be utilized.

Figure 2:
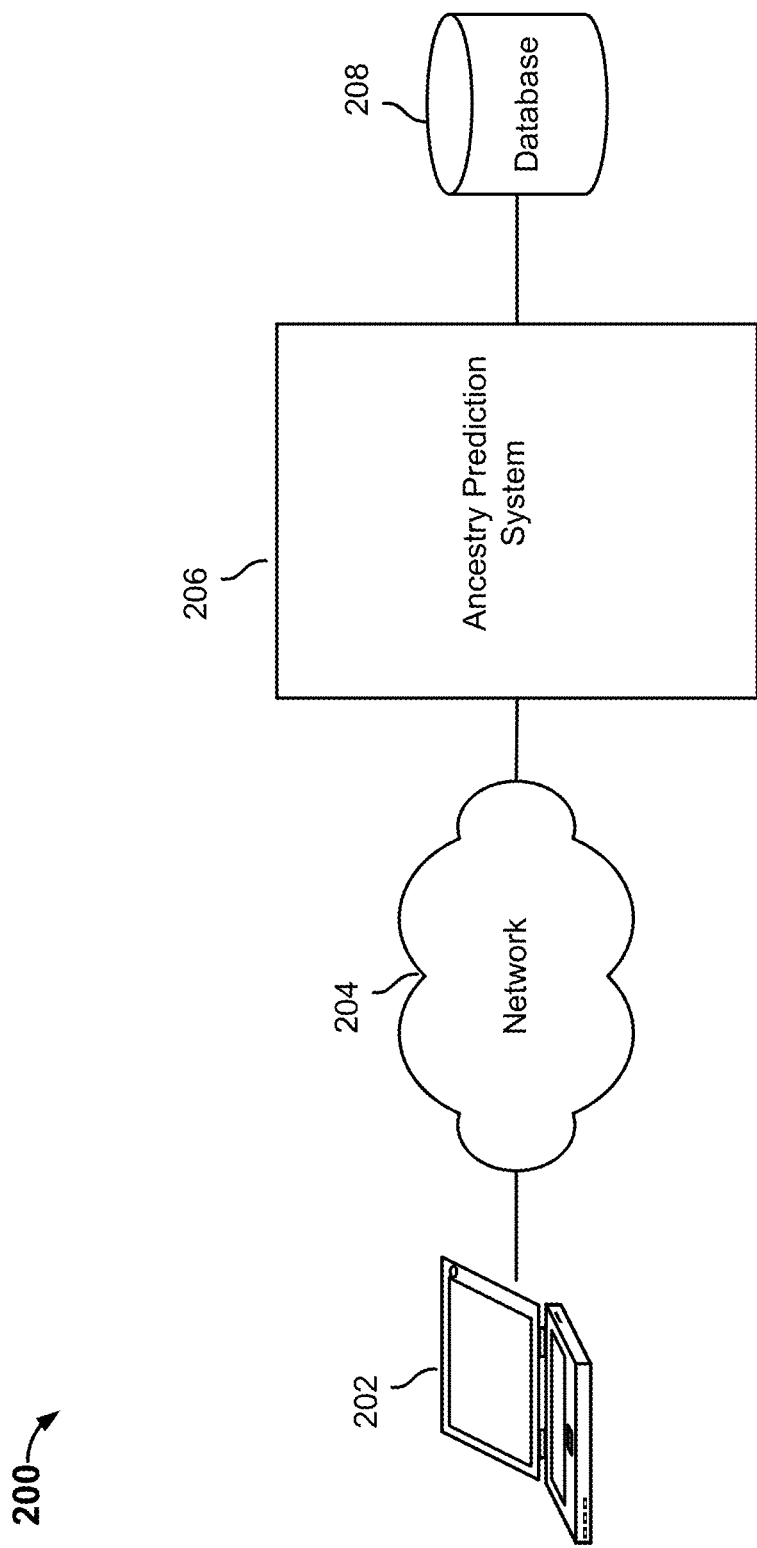
FIG. 2 is a block diagram illustrating an embodiment of an ancestry prediction platform.

FIG. 2 is a block diagram illustrating an embodiment of an ancestry prediction platform. In this example, a user uses a client device 202 to communicate with an ancestry prediction system 206 via a network 204. Examples of device 202 include a laptop computer, a desktop computer, a smart phone, a mobile device, a tablet device or any other computing device. Ancestry prediction system 206 is used to perform a pipelined process to predict ancestry based on a user's genotype information. Ancestry prediction system 206 can be implemented on a networked platform (e.g., a server or cloud-based platform, a peer-to-peer platform, etc.) that supports various applications. For example, embodiments of the platform perform ancestry prediction and provide users with access (e.g., via appropriate user interfaces) to their personal genetic information (e.g., genetic sequence information and/or genotype information obtained by assaying genetic materials such as blood or saliva samples) and predicted ancestry information. In some embodiments, the platform also allows users to connect with each other and share information. Device 100 can be used to implement 202 or 206.

In some embodiments, DNA samples (e.g., saliva, blood, etc.) are collected from genotyped individuals and analyzed using DNA microarray or other appropriate techniques. The genotype information is obtained (e.g., from genotyping chips directly or from genotyping services that provide assayed results) and stored in database 208 and is used by system 206 to make ancestry predictions. Reference data, including genotype data of unadmixed individuals (e.g., individuals whose ancestors came from the same region), simulated data (e.g., results of machine-based processes that simulate biological processes such as recombination of parents' DNA), pre-computed data (e.g., a precomputed reference haplotype graph used in out-of-sample phasing) and the like can also be stored in database 208 or any other appropriate storage unit.

Figure 3:
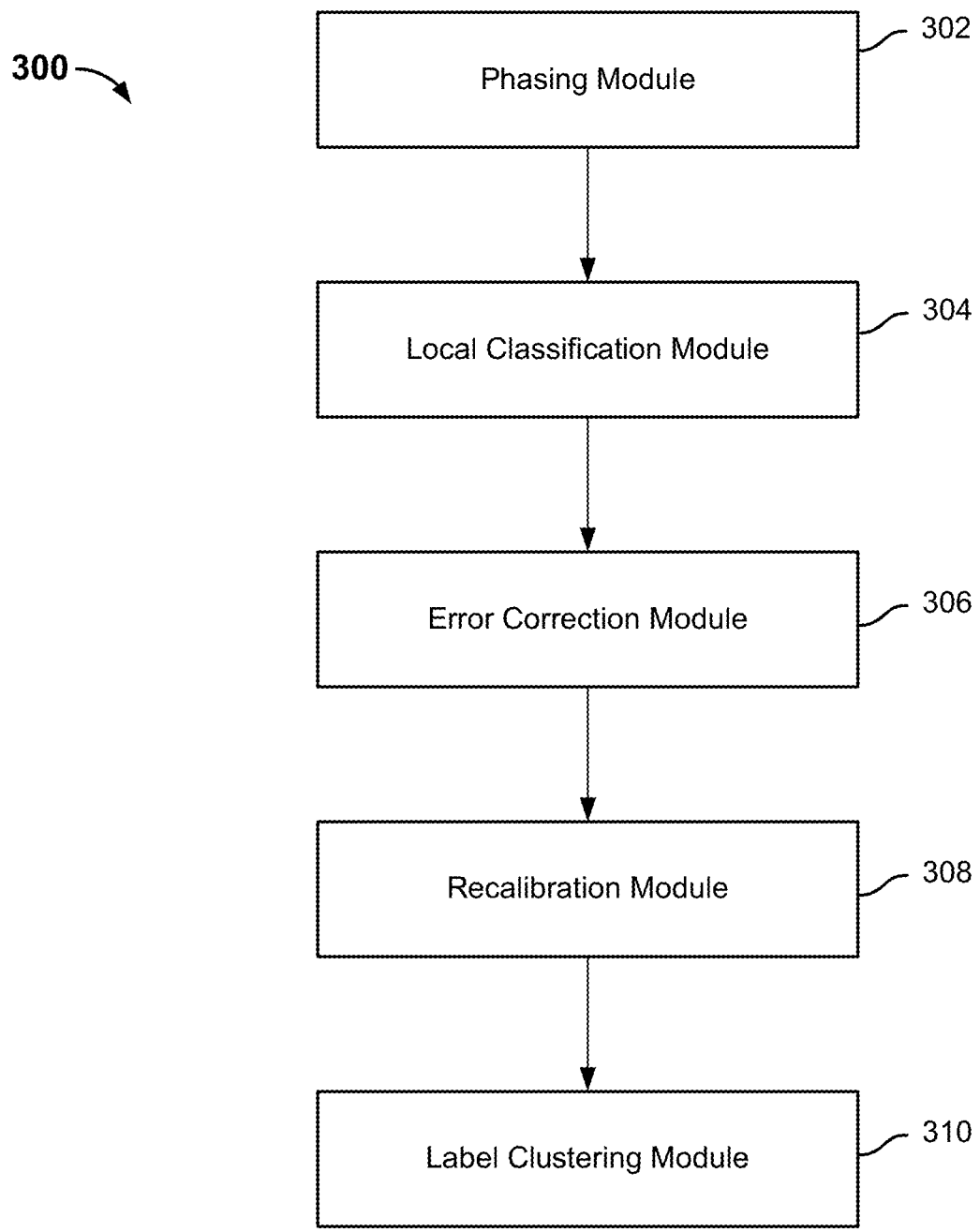
FIG. 3 is an architecture diagram illustrating an embodiment of an ancestry prediction system.

FIG. 3 is an architecture diagram illustrating an embodiment of an ancestry prediction system. System 300 can be used to implement 206 of FIG. 2, and can be implemented using system 100 of FIG. 1. The processing pipeline of system 300 includes a phasing module 302, a local classification module 304, and an error correction module 306. These modules form a predictive engine that makes predictions about the respective ancestries that correspond to the individual's chromosome portions. Optionally, a recalibration module 308 and/or a label clustering module 310 can also be included to refine the output of the predictive engine.

The input to phasing module 302 comprises unphased genotype data, and the output of the phasing module comprises phased genotype data (e.g., two sets of haplotype data). In some embodiments, phasing module 302 performs out-of-sample phasing where the unphased genotype data being phased is not included in the reference data used to perform phasing. The phased genotype data is input into local classification module 304, which outputs predicted ancestry information associated with the phased genotype data. In some embodiments, the phased genotype data is segmented, and the predicted ancestry information includes one or more ancestry predictions associated with the segments. The posterior probabilities associated with the predictions are also optionally output. The predicted ancestry information is sent to error correction module 306, which averages out noise in the predicted ancestry information and corrects for phasing errors introduced by the phasing module and/or correlated prediction errors introduced by the local classification module. The output of the error correction module can be presented to the user (e.g., via an appropriate user interface). Optionally, the error correction module sends its output (e.g., error corrected posterior probabilities) to a recalibration module 308, which recalibrates the output to establish confidence levels based on the error corrected posterior probabilities. Also optionally, the calibrated confidence levels are further sent to label clustering module 310 to identify appropriate ancestry assignments that meet a confidence level requirement.

The modules described above can be implemented as software components executing on one or more processors, as hardware such as programmable logic devices and/or Application Specific Integrated Circuits designed to perform certain functions or a combination thereof. In some embodiments, the modules can be embodied by a form of software products which can be stored in a nonvolatile storage medium (such as optical disk, flash storage device, mobile hard disk, etc.), including a number of instructions for making a computer device (such as personal computers, servers, network equipment, etc.) implement the methods described in the embodiments of the present application. The modules may be implemented on a single device or distributed across multiple devices. The functions of the modules may be merged into one another or further split into multiple sub-modules.

In addition to being a part of the pipelined ancestry prediction process, the modules and their outputs can be used in other applications. For example, the output of the phasing module can be used to identify familial relatives of individuals in the reference database.

Figure 4:
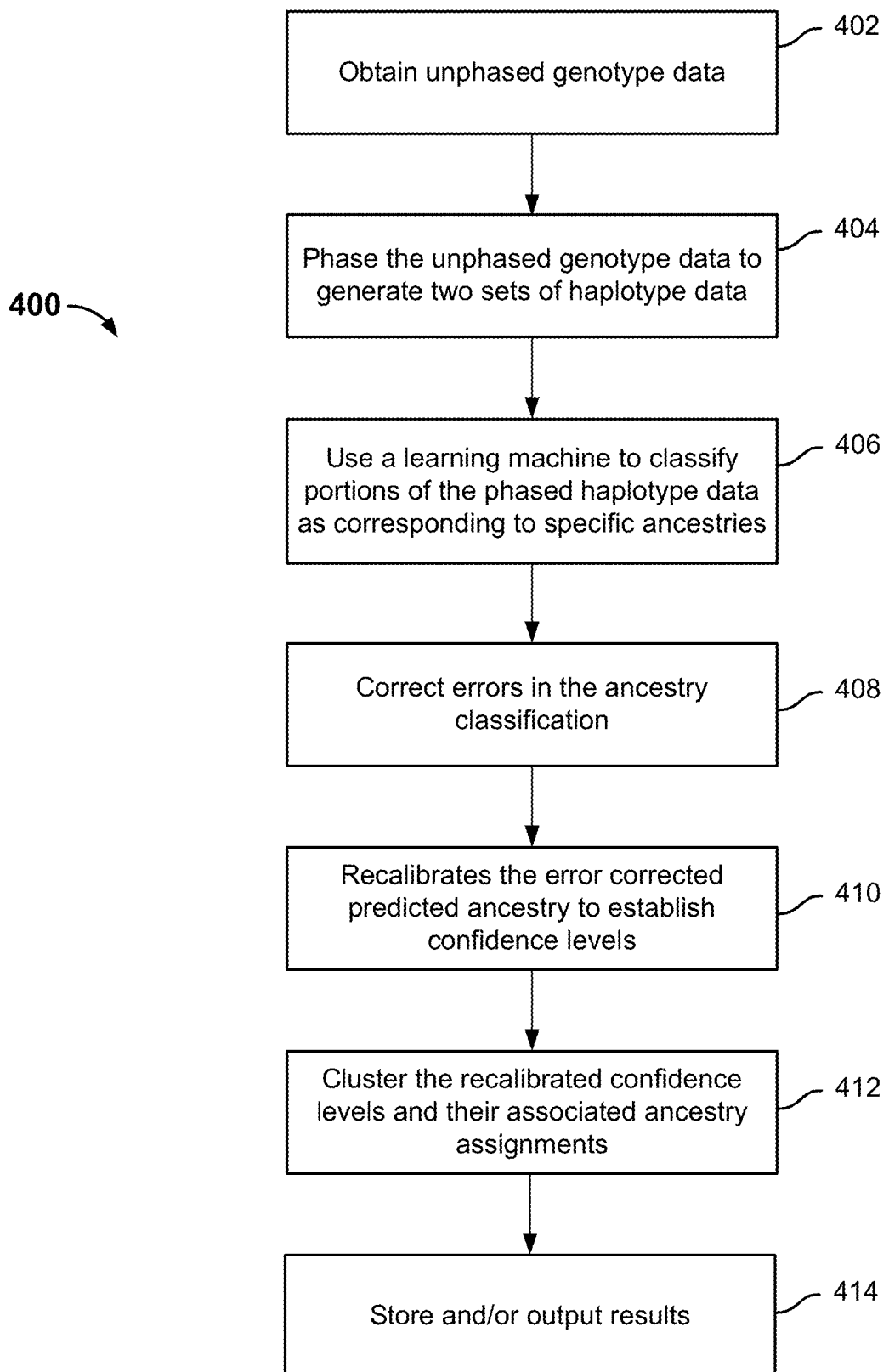
FIG. 4 is a flowchart illustrating an embodiment of a process for ancestry prediction.

FIG. 4 is a flowchart illustrating an embodiment of a process for ancestry prediction. Process 400 initiates at 402, when unphased genotype data associated with one or more chromosomes of an individual is obtained. The unphased genotype data can be received from a data source such as a database or a genotyping service, or obtained by user upload. At 404, the unphased genotype data is phased using an out-of-sample technique to generate two sets of phased haplotype data. Each set of phased haplotype data corresponds to the DNAs the individual inherited from one biological parent. At 406, a learning machine (e.g., a support vector machine (SVM)) is used to classify portions of the two sets of haplotype data as being associated with specific ancestries respectively, and generate ancestry classification results. At 408, errors in the results of the ancestry classification are corrected. In some embodiments, error correction removes noise, corrects phasing errors and/or correlated prediction errors. Optionally, at 410, the error corrected predicted ancestry information is recalibrated to establish confidence levels. Optionally, at 412, the recalibrated confidence levels and their associated ancestry assignments are clustered as appropriate to identify ancestry assignments that meet a confidence level requirement. Optionally, at 414, the resulting confidence levels and their associated ancestry assignments are stored to a database and/or output to another application (e.g., an application that analyzes the results and/or displays predicted ancestry information to users).

Details of the modules and their operations are described below.

Phasing

At a given gene locus on a pair of autosomal chromosomes, a diploid organism (e.g., a human being) inherits one allele of the gene from the mother and another allele of the gene from the father. At a heterozygous gene locus, two parents contribute different alleles (e.g., one A and one C). Without additional processing, it is impossible to tell which parent contributed which allele. Such genotype data that is not attributed to a particular parent is referred to as unphased genotype data. Typically, initial genotype readings obtained from genotyping chips manufactured by companies such as Illumina® are in an unphased form.

Figure 5A:
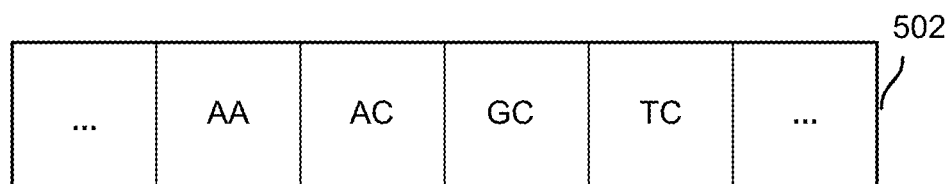
FIG. 5A illustrates an example of a section of unphased genotype data.

FIG. 5A illustrates an example of a section of unphased genotype data. Genotype data section 502 includes genotype calls at known SNP locations of a chromosome pair. The process of phasing is to split a stretch of unphased genotype calls such as 502 into two sets of phased genotype data (also referred to as haplotype data) attributed to a particular parent. Phasing is needed for identifying ancestry from each parent and classifying haplotypes from different ancestral origins. Further, a specific marker alone tends not to offer good ancestral (e.g., geographical or ethic) specificity, but a run of multiple markers can offer better specificity. For example, a particular SNP of "A" is not very informative with respect to the ancestry origin of the section of DNA, but a haplotype of a longer stretch (e.g., "ACGA") starting at a specific location can be highly correlated with Northern European ancestry.

Figure 5B:
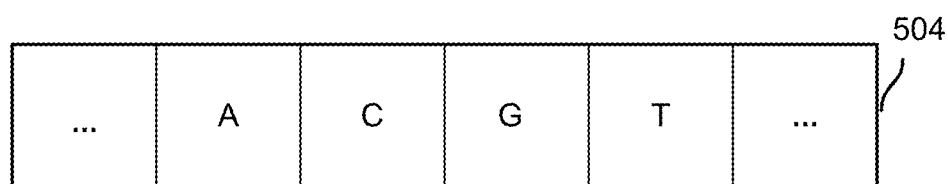
FIG. 5B illustrates an example of two sets of phased genotype data.
Figure 5B:
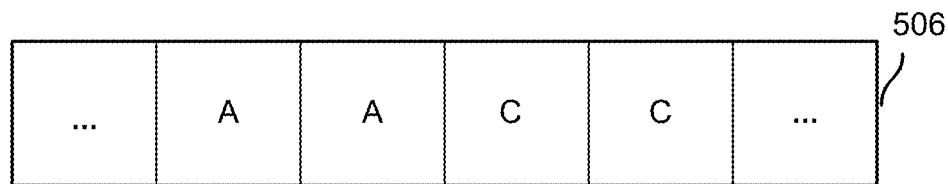

FIG. 5B illustrates an example of two sets of phased genotype data. In this example, phased genotype data (i.e., haplotype data) 504 and 506 is obtained from unphased genotype data 502 based on statistical techniques. Haplotype block 504 ("ACGT") is determined to be attributed to (i.e., inherited from) one parent, and haplotype block 506 ("AACC") is determined to be attributed to another parent.

Population-Based Phasing

Phasing is often done using statistical techniques. Such techniques are also referred to as population-based phasing because genotype data from a reference collection of a population of individuals (e.g., a few hundred to a thousand) is analyzed. BEAGLE is a commonly used population-based phasing technique. It makes statistical determinations based on the assumption that certain blocks of haplotypes are inherited in blocks and therefore shared amongst individuals. For example, if the genotype data of a sample population comprising many individuals shows a common pattern of "?A ?C ?G ?T" (where "?" can be any other allele), then the block "ACGT" is likely to be a common block of haplotypes that is present in these individuals. The population-based phasing technique would therefore identify the block "ACGT" as coming from one parent whenever "?A ?C ?G ?T" is present in the genotype data. Because BEAGLE requires that the genotype data being analyzed be included in the reference collection, the technique is referred to as in-sample phasing.

In-sample phasing is often computationally inefficient. Phasing of a large database of a user's genome (e.g., 100,000 or more) can take many days, and it can take just as long whenever a new user has to be added to the database since the technique would recompute the full set of data (including the new user's data). There can also be mistakes during in-sample phasing. One type of mistake, referred to as phasing errors or switch errors, occurs where a section of the chromosome is in fact attributed to one parent but is misidentified as attributed to another parent. Switch errors can occur when a stretch of genotype data is not common in the reference population. For example, suppose that a parent actually contributed the haplotype of "ACCC" and another parent actually contributed the haplotype of "AAGT" to genotype 502. Because the block "ACGT" is common in the reference collection and "ACCC" has never appeared in the reference collection, the technique attributes "ACGT" and "AACC" to two parents respectively, resulting in a switch error.

Embodiments of the phasing technique described below permit out-of-sample population-based phasing. In out-of-sample phasing, when genotype data of a new individual needs to be phased, the genotype data is not necessarily immediately combined with the reference collection to obtain phasing for this individual. Instead, a precomputed data structure such as a predetermined reference haplotype graph is used to facilitate a dynamic programming based process that quickly phases the genotype data. For example, given the haplotype graph and unphased data, the likely sequence of genotype data can be solved using the Viterbi algorithm. This way, on a platform with a large number of users forming a large reference collection (e.g., at least 100,000 individuals), when a new individual signs up with the service and provides his/her genotype data, the platform is able to quickly phase the genotype data without having to recompute the common haplotypes of the existing users plus the new individual.

Figure 6:
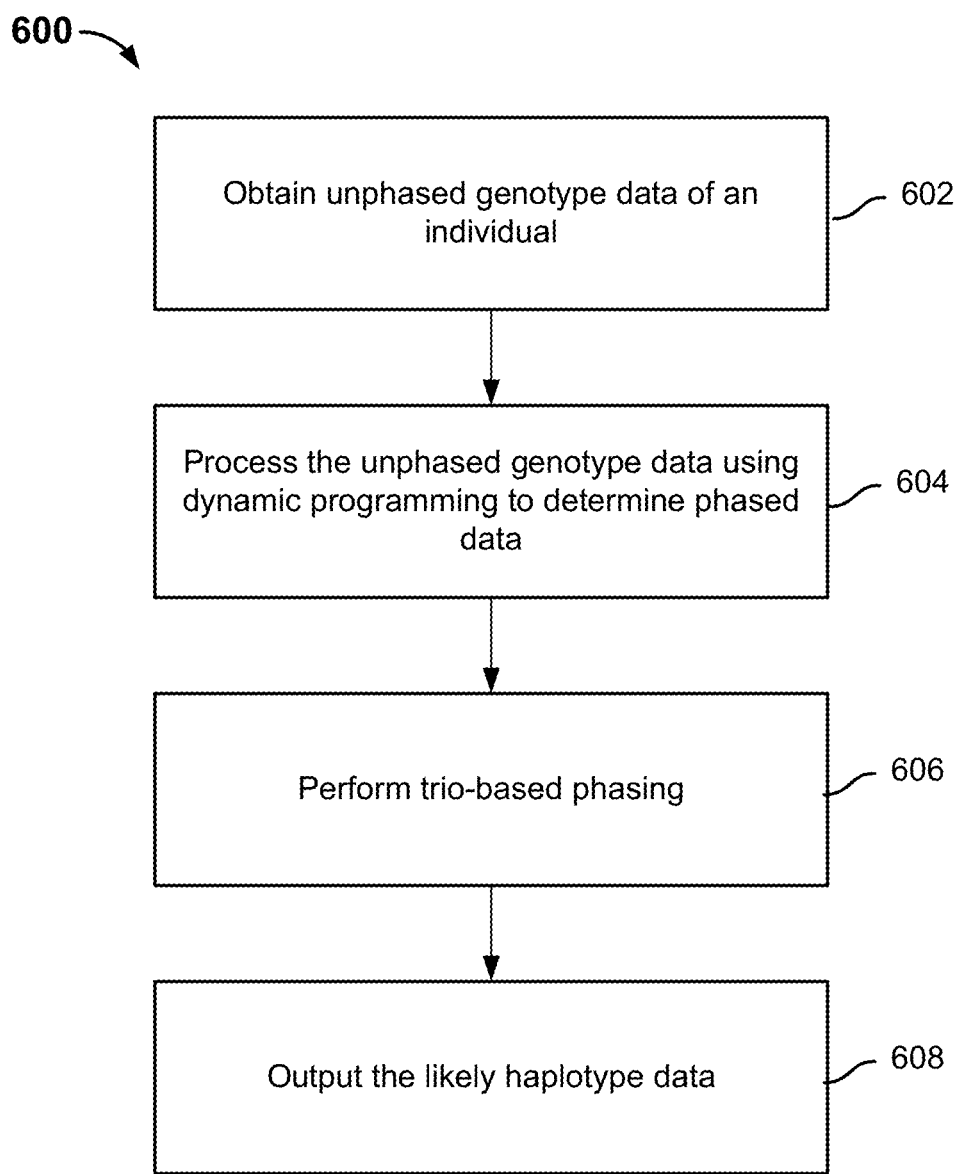
FIG. 6 is a flowchart illustrating an embodiment of a process for performing out-of-sample phasing.

FIG. 6 is a flowchart illustrating an embodiment of a process for performing out-of-sample phasing. Process 600 can be performed on a system such as 100 or 206, and can be used to implement phasing module 302.

At 602, unphased genotype data of the individual is obtained. In some embodiments, the unphased genotype data such as sequence data 502 is received from a database, a genotyping service, or as an upload by a user of a platform such as 100.

At 604, the unphased genotype data is processed using dynamic programming to determine phased data, i.e., sets of likely haplotypes. The processing requires a reference population and is therefore referred to as population-based phasing. In some embodiments, the dynamic programming relies on a predetermined reference haplotype graph. The predetermined haplotype graph is precomputed without referencing the unphased genotype data of the individual. Thus, the unphased genotype data is said to be out-of-sample with respect to a collection of reference genotype data used to compute the predetermined reference haplotype graph. In other words, if the unphased genotype data is from a new user whose genotype data is not already included in the reference genotype data and therefore is not incorporated into the predetermined reference haplotype graph, it is not necessary to include the unphased genotype data from the new user in the reference genotype data and recompute the reference haplotype graph. Details of dynamic programming and the predetermined reference haplotype graph are described below.

At 606, trio-based phasing is optionally performed to improve upon the results from population-based phasing. As used herein, trio-based phasing refers to phasing by accounting for the genotyping data of one or more biological parents of the individual.

At 608, the likely haplotype data is output to be stored to a database and/or processed further. In some embodiments, the likely haplotype data is further processed by a local classifier as shown in FIG. 3 for ancestry prediction purposes.

The likely haplotype data can also be used in other applications, such as being compared with haplotype data of other individuals in a database to identify the amount of DNA shared among individuals, thereby determining people who are related to each other and/or people belonging to the same population groups.

In some embodiments, the dynamic programming process performed in step 604 uses a predetermined reference haplotype graph to examine possible sequences of haplotypes that could be combined to generate the unphased genotype data, and determine the most likely sequences of haplotypes. Given a collection of binary strings of length L, a haplotype graph is a probabilistic deterministic finite automaton (DFA) defined over a directed acyclic graph. The nodes of the multigraph are organized into L+1 levels (numbered from 0 to L), such that level 0 has a single node representing the source (i.e., initial state) of the DFA and level L has a single node representing the sink (i.e., accepting state) of the DFA. Every directed edge in the multigraph connects a node from some level i to a node in level (i+1) and is labeled with either 0 or 1. Every node is reachable from the source and has a directed path to the sink. For each path through the haplotype graph from the source to the sink, the concatenation of the labels on the edges traversed by the path is a binary string of length L. Semantically, paths through the graph represent haplotypes over a genomic region comprising L biallelic markers (assuming an arbitrary binary encoding of the alleles at each site). A probability distribution over the set of haplotypes included in a haplotype graph can be defined by associating a conditional probability with each edge (such that the sum of the probabilities of the outgoing edges for each node is equal to 1), and generated by starting from the initial state at level 0, and choosing successor states by following random outgoing edges according to their assigned conditional probabilities.

Figure 7:
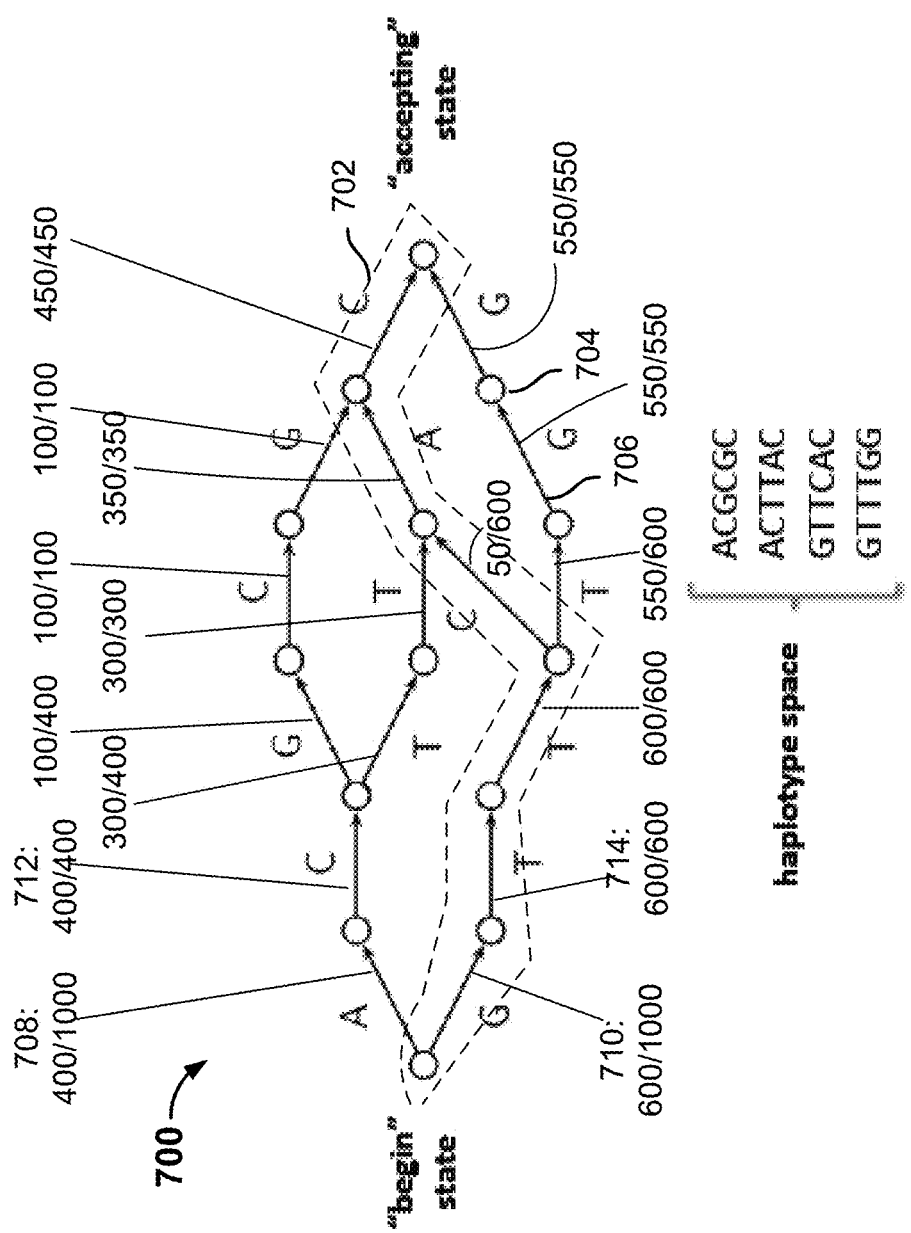
FIG. 7 is a diagram illustrating an example of a predetermined reference haplotype graph that is built based on a reference collection of genotype data.

FIG. 7 is a diagram illustrating an example of a predetermined reference haplotype graph that is built based on a reference collection of genotype data (e.g., population-based data). In this example, the reference collection of genotype data includes a set of L genetic markers (e.g., SNPs). Haplotype graph 700 is a Directed Acyclic Graph (DAG) having nodes (e.g., 704) and edges (e.g., 706). The haplotype graph starts with a single node (the "begin state") and ends on a single node (the "accepting state"), and the intermediate nodes correspond to the states of the markers at respective gene loci. There is a total of L+1 levels of nodes from left to right. An edge, e, represents the set of haplotypes whose path from the initial node to the terminating node of the graph traverses e. The possible paths define the haplotype space of possible genotype sequences. For example, in haplotype graph 700, a possible path 702 corresponds to the genotype sequence "GTTCAC". There are four possible paths/genotype sequences in the haplotype space shown in this diagram ("ACGCGC," "ACTTAC," "GTTCAC," and "GTTTGG").

Each edge is associated with a probability computed based on the reference collection of genotype data. In this example, a collection of genotype data is comprised of genotype data from 1000 individuals, of which 400 have the "A" allele at the first locus, and 600 have the "G" allele at the first locus. Accordingly, the probability associated with edge 708 is 400/1000 and the probability associated with edge 710 is 600/1000. All of the first 400 individuals have the "C" allele at the second locus, giving edge 712 a probability of 400/400. All of the next 600 individuals who had the "G" allele at the first locus have the "T" allele at the second locus, giving edge 714 a probability of 600/600, and so on. The probabilities associated with the respective edges are labeled in the diagram. The probability associated with a specific path is expressed as the product of the probabilities associated with the edges included in the path. For example, the probability associated with path 702 is computed as:

$$P(h) = \left(\frac{600}{1000}\right)\left(\frac{600}{600}\right)\left(\frac{600}{600}\right)\left(\frac{50}{600}\right)\left(\frac{350}{350}\right)\left(\frac{450}{450}\right) = 0.05$$

The dynamic programming process searches the haplotype graph for possible paths, selecting two paths $h_1$ and $h_2$ for which the product of their associated probabilities is maximized, subject to the constraint that when the two paths are combined, the alleles at each locus must match the corresponding alleles in the unphased genotype data (g). The following expression is used in some cases to characterize the process:

maximize $P(h_1)P(h_2)$, subject to $h_1+h_2=g$

For out-of-sample phasing, the reference haplotype graph is built once and reused to identify possible haplotype paths that correspond to the unphased genotype data of a new individual (a process also referred to as "threading" the new individual's haplotype along the graph). The individual's genotype data sometimes does not correspond to any existing path in the graph (e.g., the individual has genotype sequences that are unique and not included in the reference population), and therefore cannot be successfully threaded based on existing paths of the reference haplotype graph. To cope with the possibility of a non-existent path, several modifications are made to the reference haplotype graph to facilitate the out-of-sample phasing process.

Figure 8A:
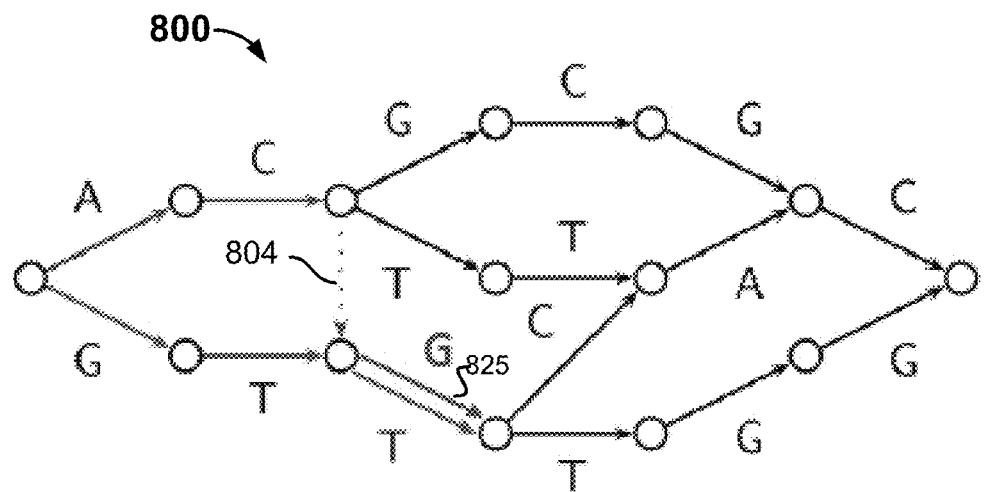
FIGS. 8A-8B are diagrams illustrating embodiments of modified haplotype graphs.
Figure 8B:
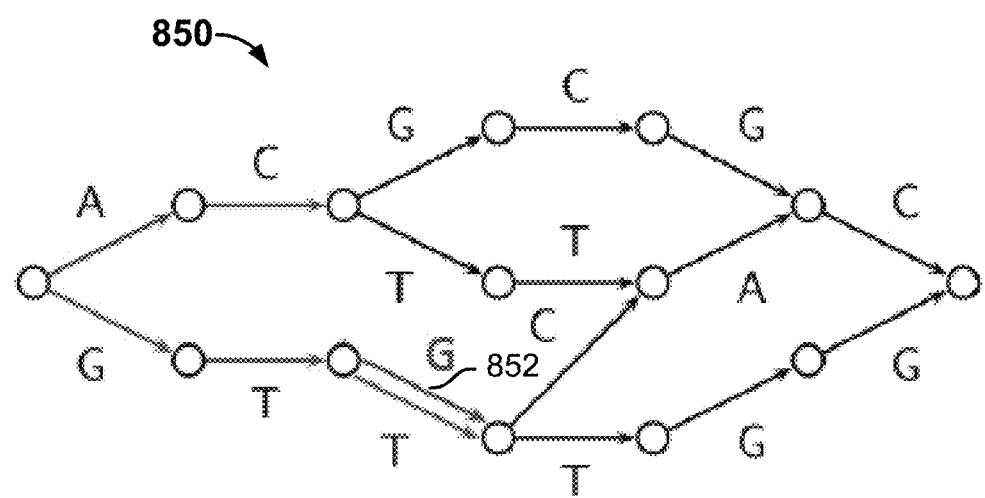

FIGS. 8A-8B are diagrams illustrating embodiments of modified haplotype graph used for out-of-sample, population-based phasing. In these examples, modified reference haplotype graphs 800 and 850 are based on graph 700. Unlike graph 700, which is based on exact readings of genotype sequences of the reference individuals, the modified graphs permit recombination and genotyping errors and include modifications (e.g., extra edges) that account for recombination and genotyping errors.

Recombination is one reason to extend graph 700 for out-of-sample phasing. As used herein, recombination refers to the switching of a haplotype along one path to a different path. Recombination can happen when segments of parental chromosomes cross over during meiosis. In some embodiments, reference haplotype graph 700 is extended to account for the possibility of recombination/path switching. Recombination events are modeled by allowing a new haplotype state to be selected (independent of the previous haplotype state) with probability τ at each level of the haplotype graph. By default, τ≈0.00448, which is an estimate of the probability of recombination between adjacent sites, assuming 500,000 uniformly spaced markers, a genome length of 37.5 Morgans, and 30 generations since admixture. Referring to the example of FIG. 8A, suppose the new individual's unphased genotype data is "AG, CT, TT, TT, GG, GG," (SEQ ID NO: 1) which cannot be split into two haplotypes by threading along existing paths in graph 700. The modified reference haplotype graph 800 permits recombination by including additional edges representing recombination (e.g., edge 804) so that new paths can be formed along these edges. In this example, the unphased genotype data can map onto two paths corresponding to haplotypes "ACTTGG" and "GTTTGG", the former being a new path due to recombination with a recombination occurring between "C" and "T" along edge 804. τ is associated with edge 804 and used to compute the probability of the path through 804.

Genotyping error is another reason to extend graph 700 for out-of-sample phasing. Genotyping errors can occur because the genotyping technology is imperfect and can make false readings. The rate of genotyping error for a given technology (e.g., a particular genotyping chip) can be obtained from the manufacturer. In some embodiments, when the search for possible paths for a new individual cannot be done according to the existing reference graph, the existing reference haplotype graph is extended to account for the possibility of genotyping errors. For example, suppose the new individual's unphased genotype data is "AG, CT, GG, CT, GG, CG," (SEQ ID NO: 2) which cannot be split into two haplotypes by threading along existing paths in graph 700. Referring to FIG. 8B, the reference haplotype graph is extended to permit genotyping errors and a new edge 852 is added to the graph, permitting a reading of "G" instead of "T" at this locus. The probability associated with this edge is determined based on the rate of genotyping error for the genotyping technology used. The unphased genotype data can therefore be split into haplotypes "ACGCGC" and "GTGTGG", the latter being a new path based on the extended reference haplotype graph. In some embodiments, to account for genotyping error, the out-of-sample phaser explicitly allows genotyping error with a constant probability of y (which depends on the error rate of the given technology, and is set to 0.01 in some cases) for each emitted edge label.

The example graphs shown include a small number of nodes and edges, and thus represent short sequences of genotype data. In practice, the begin state node corresponds to the first locus on the chromosome and the accepting state node the last locus on the chromosome, and the number of edges in a path corresponds to the number of SNPs in a chromosome (L), which can be on the order of 50,000 in some embodiments. The thickest portion of the graph (i.e., a locus with the greatest number of possible paths), which depends at least in part on the DNA sequences of individuals used to construct the graph (K), can be on the order of 5,000 in some embodiments. A large number of computations would be needed ($O(LK^4)$ in the worst case) for a naïve implementation of a dynamic programming solution based on the Viterbi algorithm.

In some embodiments, the paths are pruned at each state of the graph to further improve performance. In other words, only likely paths are kept in the modified graph and unlikely paths are discarded. In some embodiments, after i markers (e.g., 3 markers), paths with probabilities below a certain threshold E (e.g., less than 0.0001%) are discarded. For example, a haplotype along a new path that accounts for both recombination and switching error would have very low probability of being formed, and thus can be discarded. As another example, in the case of unphased genotype data of "AG, CT, GG, CT, GG, CG," (SEQ ID NO: 2) a new haplotype accounting for recombination can be forged by switching paths several times along the graph (additional edges would need to be added but are not shown in the diagram). Given the low probability associated with each switch, however, the formation of such a haplotype is very unlikely and would be pruned from the resulting graph, while the path that includes the genotyping error 825 has sufficiently high probability, and is kept in the graph and used to thread the unphased genotype data into phased genotype data. By pruning unlikely paths from the modified graph, the dynamic programming-based phasing process is prevented from exploring very unlikely paths in the graph when threading a new haplotype along it. The choice of E determines the trade-off between the efficiency of the algorithm (in both time and space) and the risk of prematurely excluding the best Viterbi path. Computation savings provided by pruning can be significant. In some cases, phasing using a naïve implementation can require 15 days per person while phasing with pruning only requires several minutes per person.

In some embodiments, the nodes and edges of the haplography can be represented as follows:

```
struct Node {
    int32_t id;
    int32_t level;
    Edge *outgoing[2];
};
struct Edge {
    int16_t id;
    int8_t allele;
    float weight;
    Node *to;
}
```

Even with a pruned haplotype graph, the number of nodes and edges can be large and using the above data structures to represent the graph would require a vast amount of memory (on the order of several gigabytes in some cases). In some embodiments, the graph is represented in a compressed form, using segments. The term "segment" used herein refers to the data structure used to represent the graph in a compressed form and is different from the DNA segments used elsewhere in the specification. Each segment corresponds to a contiguous set of edges in the graph, with the following constraints: the end of the segment has up to 1 branch (0 branches are permitted), and no segment points to the middle of another segment. In some embodiments, the data structure of a segment is represented as follows:

```
struct Segment {
    int32_t timestamp;
    int32_t index;
    int32_t begin;
    int32_t end;
    int32_t count[2];
    Segment *edges[2];
}
```

Figure 9:
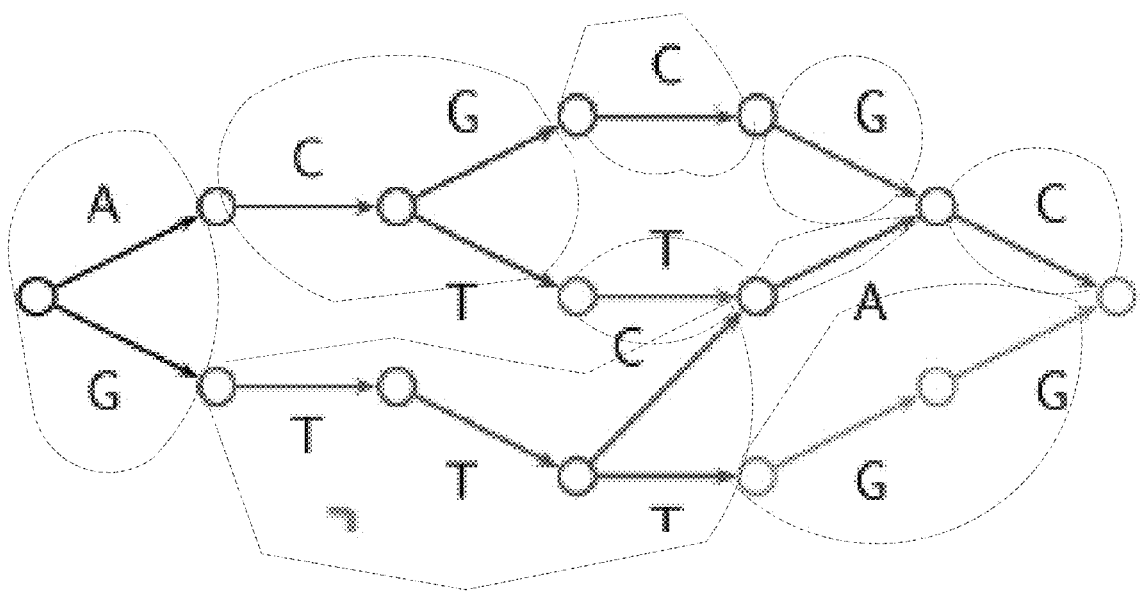
FIG. 9 is a diagram illustrating an embodiment of a compressed haplotype graph with segments.

FIG. 9 is a diagram illustrating an embodiment of a compressed haplotype graph with segments. In this example, dashed shapes are used to illustrate the individual segments enclosed within. In some cases, a compressed graph associated with a chromosome can be represented using several megabytes of memory, achieving memory reduction by a factor of 1000 compared to the naïve implementation of nodes and edges.

Trio-Based Phasing

On a system such as the personal genomics services platform provided by 23andMe®, DNA sequence information of one or both parents of the individual is sometimes available and can be used to further refine phasing. With the exception of sites where all three individuals are heterozygous, the parental origin of each allele can be determined unambiguously. For ambiguous sites, knowledge of patterns of local linkage disequilibrium can be used to statistically estimate the most likely phase. In some embodiments, a refinement process that accounts for parental DNA sequence information, referred to as trio-based phasing, is optionally performed following the population-based phasing process to correct any errors in the output of the population-based phasing process and improve phasing accuracy. In some embodiments, the trio-based phasing technique is a post-processing step to be applied to sequences for which a previous population-based linkage-disequilibrium phasing approach has already been applied. The trio-based phasing technique can be used in combination with any existing phasing process to improve phasing quality, provided that an estimate of the switch error rate (also referred to as the phasing error rate) is available.

In some embodiments, trio-based phasing receives as inputs a set of preliminary phased haplotype data (e.g., output of an out-of-sample population-based phasing technique described above), and employs a probabilistic graphic model (also referred to as a dynamic Bayesian network) that models the observed alleles, hidden states, and relationships of the parental and child haplotypes. The input includes the set of preliminary phased haplotype data as well as the phased haplotype data of at least one parent. The genotype data at a particular site (e.g., the i-th SNP on a chromosome) for each individual in the trio (i.e., mom, dad, or child (i.e. the individual whose genetic data is being phased)) are represented by the following variables:

$G_0^{*,i}, G_1^{*,i} \in \{0,1\}$: the observed alleles for haplotypes 0 and 1, provided as input data. For the child, the input data can be obtained from the output of the population-based phasing process (e.g., the preliminary haplotype data). For the parent, the input data can be the output of the population-based phasing process or the final output of a refined process.

$H_m^{*,i}, H_p^{*,i} \in \{0, 1\}$: the hidden true alleles of the individual's maternal (m) and paternal (p) haplotypes.

$P^{*,i} \in \{m, p\}$: a hidden binary phase indicator variable that is set to m whenever $G_0^{*,i}$ corresponds to $H_m^{*,i}$ and set to p whenever $G_0^{*,i}$ corresponds to $H_p^{*,i}$.

The relationship between parental and child haplotypes are encoded by two additional variables, $T^{mom,i}, T^{dad,i} \in \{a, b\}$, where a indicates transmission of the parent's maternal haplotype to the child and b indicates transmission of the parent's paternal haplotype to the child. In some embodiments, a=0 and b=1.

The following assumptions are made about the model:

1. The hidden true alleles for each parent at each position (i.e., $H_+^{(mom,dad),i}$), the initial phase for each individual (i.e., $P^{*,1}$), and the initial transmission for each parent (i.e., $T^{*,1}$) are independently drawn from uniform Bernoulli priors.

2. The phase indicator variables for each individual and the transmission indicator variables for each parent are each sampled according to independent first order Markov processes. Specifically, $$P(P^{*,i} | P^{*,i-1}) = \begin{cases} 1-s & \text{if } P^{*,i} = P^{*,i-1} \\ s & \text{otherwise} \end{cases}$$

$$P(T^{*,i} | T^{*,i-1}) = \begin{cases} 1-r & \text{if } T^{*,i} = T^{*,i-1} \\ r & \text{otherwise} \end{cases}$$

where s is the estimated switch error probability between consecutive sites in the input haplotypes and r is the estimated recombination probability between sites in a single meiosis. In some embodiments, s is set to a default value of 0.02 and r is set to a default value of $$\frac{1}{2}\left(1 - e^{-2\left(\frac{37.5}{500000}\right)}\right) \approx 0.000075.$$

3. The hidden true alleles for the child at each position (i.e., $H_+^{kid,i}$) are deterministically set on the parents' true hidden haplotypes (i.e., neglecting the possibility of private mutations) and their respective transmission variables.

4. The observed alleles are sampled conditionally on the true alleles and the phase variables with genotyping error, according to the following model:

$$P(G_0^{*,i} | H_m^{*,i}, H_p^{*,i}, P^{*,i}) = \begin{cases} 1-g & \text{if } G_0^{*,i} = H_{p^{*,i}}^{*,i} \\ g & \text{otherwise} \end{cases}$$

according to the estimated genotyping error rate.

The following expression is used to characterize the trio-based phasing process:

$$\text{maximize } \Pr(H_m^{kid}, H_p^{kid}, H_m^{mom}, H_p^{mom}, H_m^{dad}, H_p^{dad})$$

$$\text{given } H_m^i + H_p^i = G_0^i + G_1^i \forall i \in \{kid, mom, dad\}$$

Figure 10:
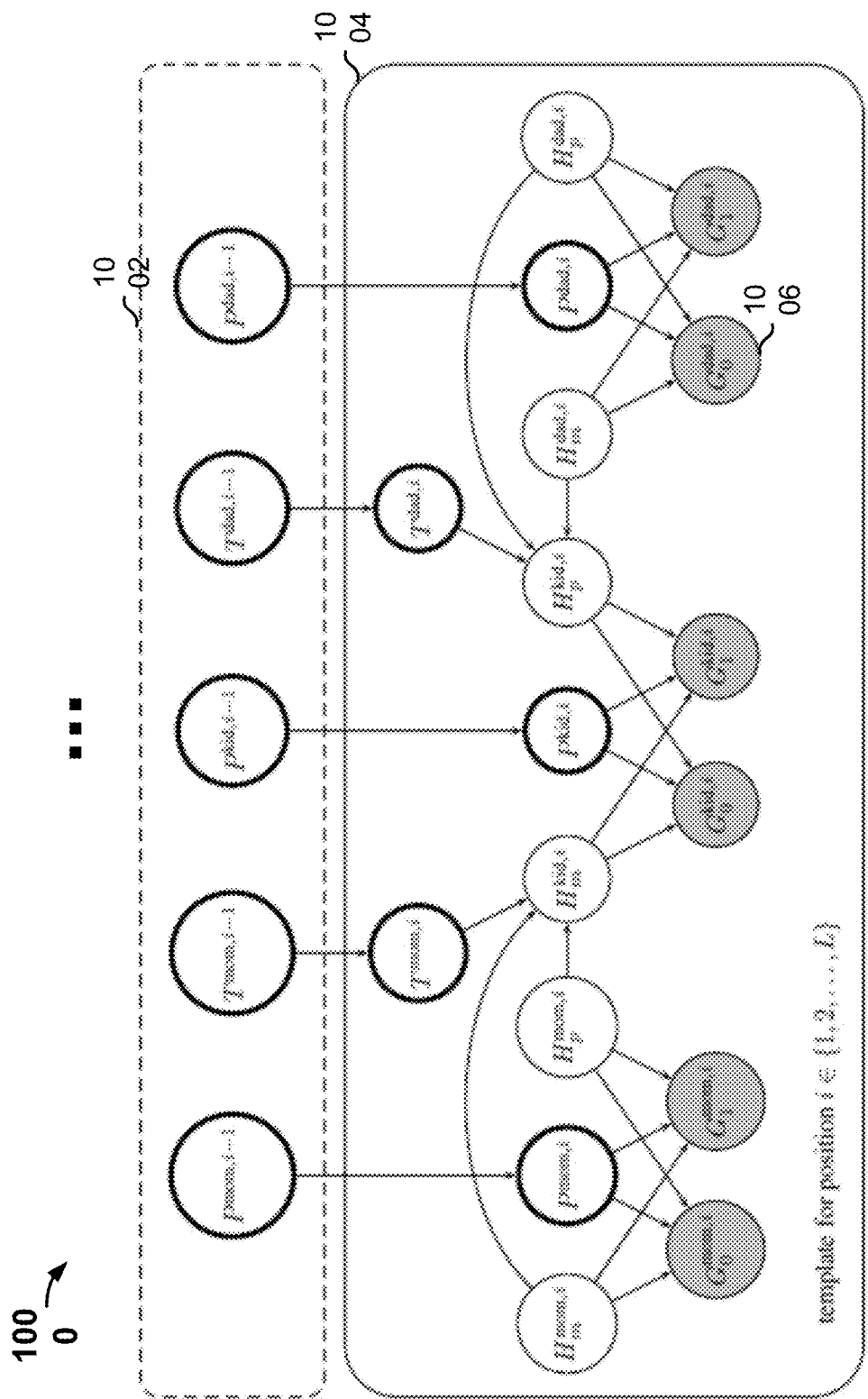
FIG. 10 is a diagram illustrating an embodiment of a dynamic Bayesian network used to implement trio-based phasing.

FIG. 10 is a diagram illustrating an embodiment of a dynamic Bayesian network used to implement trio-based phasing. The diagram depicts the structure of the dynamic Bayesian network using plate notation. Rounded rectangles (also referred to as plates) such as 1002 and 1004 are used to denote repeated structures in the graph model. Each plate corresponds to a position (e.g., the i-th marker) on the individual's chromosome. In plate 1002 which corresponds to position i−1, variables which are not connected to any variables from other plates (e.g., $H_m^{kid,i-1}$) are omitted from the diagram. Plate 1004 shows a detailed template for position i∈{1, 2, . . . , L}. As shown, nodes represent random variables in the model, and edges represent conditional dependencies. Shaded nodes (e.g., node 1006) represent random variables which are observed at testing time, and nodes with thickened edges (e.g., node 1008) represent variables which have dependencies across plates.

Trio-based phasing includes using the probabilistic model to estimate the most probable setting of all unobserved variables, conditioned on the observed alleles. In some embodiments, the most probable H variables are determined using a standard dynamic programming-based technique (e.g., Viterbi). One can visualize the model as plates corresponding to i∈{1, 2, . . . , L} being stacked in sequential order, and the paths are formed by the interconnections of nodes on the same plate, as well as nodes across plates.

Figure 11:
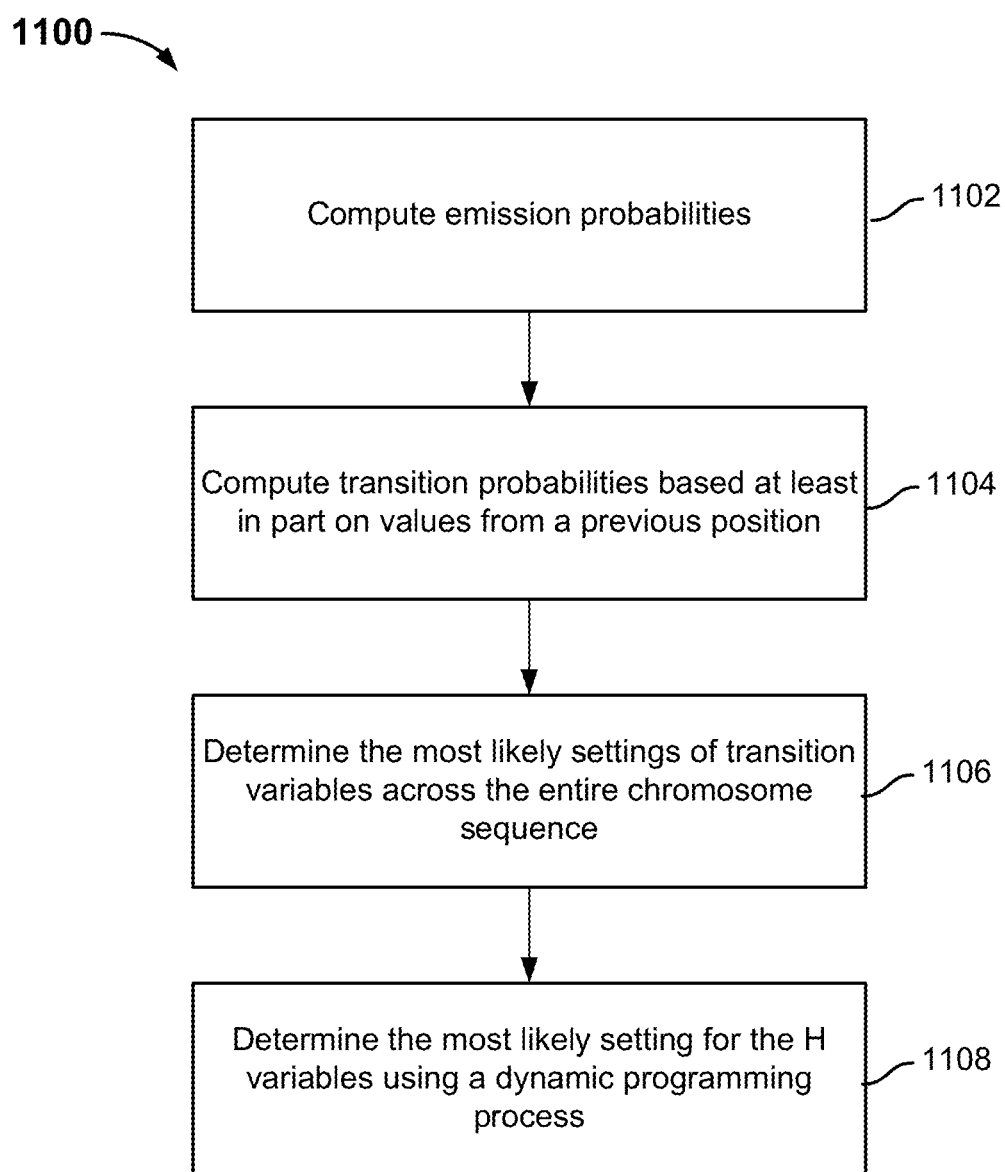
FIG. 11 is a flowchart illustrating an embodiment of a process to perform trio-based phasing.

FIG. 11 is a flowchart illustrating an embodiment of a process to perform trio-based phasing based on the model of FIG. 10. Process 1100 can be performed on a system such as 100 or 206, and can be used to implement phasing module 302 to perform post-processing of population-based phasing. It is assumed that a model such as 1000 is already established.

At 1102, emission probabilities are precomputed for each plate of model 1000. In some embodiments, the emission probabilities, which correspond to the most likely setting for the H variables given the G, P, and T variables, are found using a dynamic programming (e.g., Viterbi) based process. Referring to FIG. 10, for a given position i, there are 2 possible settings (0 or 1) for each for the variables $P^{mom}$, $P^{kid}$, $P^{dad}$, $T^{mom}$, $T^{dad}$; there are two possible settings (0 or 1) for each of the six H variables; and there are 3 possible settings (0, 1 or missing) or each of the six G variables, $2^5 * 2^6 * 3^6 = 1.5$ million possible combinations. In subsequent steps, a dynamic programming process will search these combinations to identify the most likely setting for the H variables.

At 1104, transition probabilities are computed based at least in part on the values of transition probabilities from the previous position. Referring to FIG. 10, at a given position i, the values of transition variables T and P are dependent on the values of the T and P variables from the previous position. There are 2 possible settings (0 or 1) for each of the 5 P and T variables in the upper box 1002, and 2 possible settings (0 or 1) for each of the 5 P and T variables in the lower box. The possible combinations of the T and P values are therefore $2^5 * 2^5 = 1024$.

At 1106, based on the computed probabilities, the settings of transition variables T and P across the entire chromosome sequence (i.e., for i=1, . . . , L) are searched to determine the settings that would most likely result in the observed values. In some embodiments, the determination is made using a dynamic programming technique such as Viterbi, and $2^5 * 2^5 * L$ states are searched.

At 1108, the setting of H variables is looked up across the entire sequence to determine the settings that would most likely result in the given G, P, and T variables. This requires L table lookups.

The trio-based phasing solves the most likely settings for the H variables (the hidden true alleles for the individual's maternal and paternal haplotypes at a given location). The solution is useful for phasing the child's DNA sequence information as well as for phasing a parent's DNA sequence information (if the parent's DNA sequence information is unphased initially). In the event that only one parent's DNA sequence information is available, the other parent's DNA sequence information can be partially determined based on the DNA sequence information of the known parent and the child (e.g., if the child's alleles at a particular location is "AC" and the mother's alleles at the same location are "CC", then one of the father's alleles would be "A" and the other one is unknown). The partial information can be marked (e.g., represented using a special notation) and input to the model. The quality of trio-based phasing based on only one parent's information is still higher than population-based phasing without using the trio-based method.

In addition to improved haplotypes data, the result of trio-based phasing also indicates whether a specific allele is deemed to be inherited from the mother or the father. This information is stored and can be presented to the user in some embodiments.

Local Classification

Local classification refers to the classification of DNA segments as originating from an ancestry associated with a specific geographical region (e.g., Eastern Asia, Scandinavia, etc.) or ethnicity (e.g., Ashkenazi Jew).

Local classification is based on the premise that, T generations ago, all the ancestors of an individual were unadmixed (i.e., originating from the same geographical region). Starting at T generation, ancestors from different geographical regions produced admixed offspring. Genetic recombination breaks chromosomes and recombines them at each generation. After T generations, 2T meiosis occurred. As a result, the expected length of a recombination-free segment is expressed as:

$$L = \frac{F}{2T} cM$$

where F corresponds to a fixed length segment. In some embodiments, the expected length L is determined to be 100 SNPs. It is used as the segment size (also referred to as the window size) used in local classification.

Figure 12:
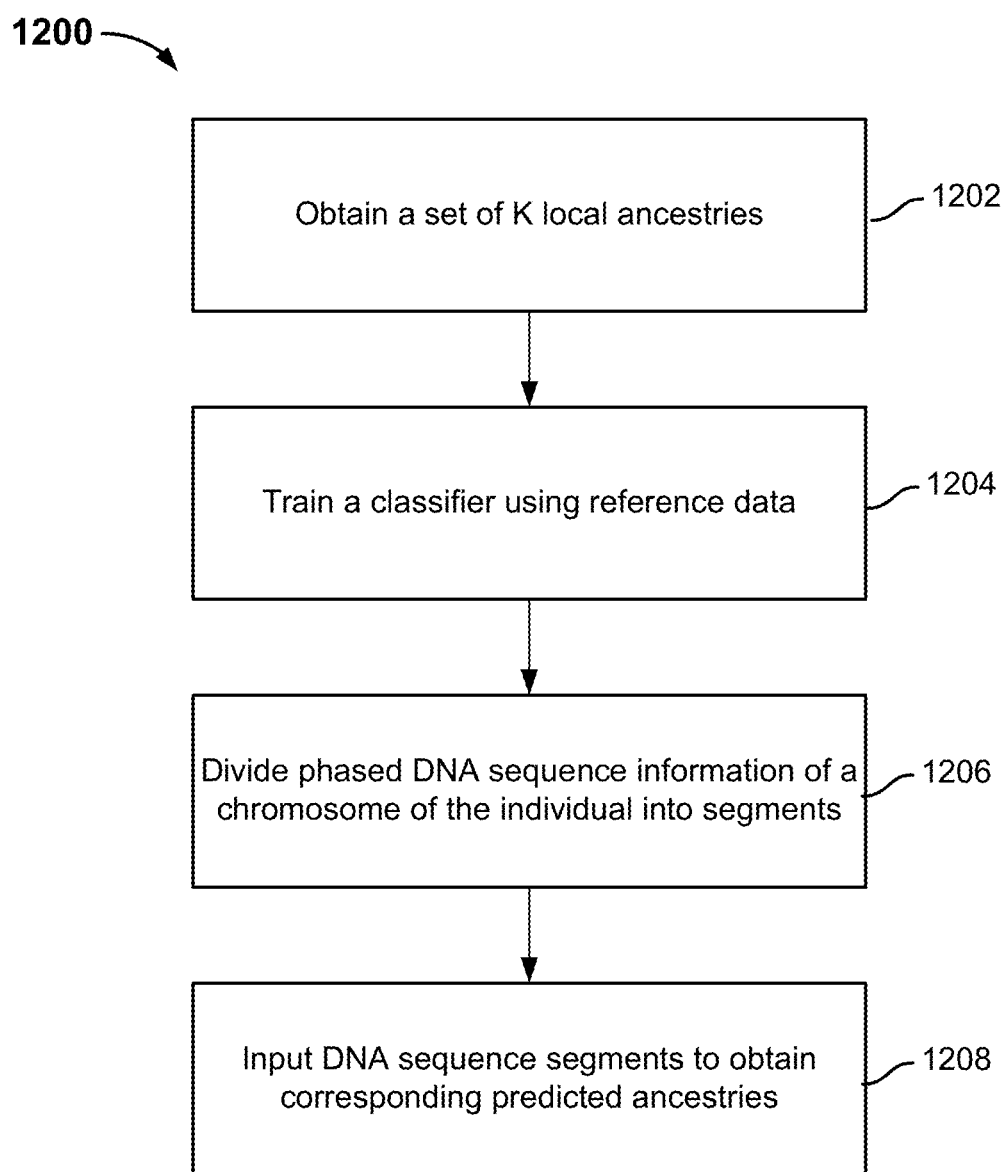
FIG. 12 is a flowchart illustrating an embodiment of a local classification process.

FIG. 12 is a flowchart illustrating an embodiment of a local classification process. Process 1200 can be performed on a platform such as 200 or a system such as 300.

Initially, at 1202, a set of K local ancestries is obtained. In some embodiments, the specification of the local ancestries depends on the ancestries of unadmixed individuals whose DNA sequence information is used as reference data. For example, the set of local ancestries can be pre-specified to include the following: African, Native American, Ashkenazi, Eastern Asian, Southern Asian, Balkan, Eastern European, Western European, Middle Eastern, British Isles, Scandinavian, Finnish, Oceanian, Iberian, Greek, Sardinian, Italian, and Arabic. Many other specifications are possible; for example, in some embodiments the set of local ancestries correspond to individual countries such as the UK, Ireland, France, Germany, Finland, China, India, etc.

At 1204, a classifier is trained using reference data. In this example, the reference data includes DNA sequence information of unadmixed individuals, such as individuals who are self-identified or identified by the system as having four grandparents of the same ancestry (i.e., from the same region), DNA sequence information obtained from public databases such as 1KG, HGDP-CEPH, HapMap, etc. The DNA sequence information and their corresponding ancestry origins are input into the classifier, which learns the corresponding relationships between the DNA sequence information (e.g., DNA sequence segments) and the corresponding ancestry origins. In some embodiments, the classifier is implemented using a known machine learning technique such as a support vector machine (SVM), a neural network, etc. A SVM-based implementation is discussed below for purposes of illustration.

At 1206, phased DNA sequence information of a chromosome of the individual is divided into segments. In some embodiments, phased data is obtained using the improved phasing technique described above. Phased data can also be obtained using other phasing techniques such as BEAGLE. The length of the segments can be a predetermined fixed value, such as 100 SNPs. It is assumed that each segment corresponds to a single ancestry.

At 1208, the DNA sequence segments are input into the trained classifier to obtain corresponding predicted ancestries. In some embodiments, the classifier determines probabilities associated with the set of local ancestries (i.e., how likely a segment is from a particular local ancestry), and the ancestry associated with the highest probability is selected as the predicted ancestry for a particular segment.

In some embodiments, one or more SVMs are used to implement the classifier. An SVM is a known type of non-probabilistic binary classifier. It constructs a hyper plane that maximizes the distance to the closest training data point of each class (in this case, a class corresponds to a specific ancestry). A SVM can be expressed using the following general expression:

$$\begin{cases} \min_{w,\xi,b} \frac{1}{2}\|w\|^2 + C\sum_i \xi_i \\ y_i(w*x_i - b) \geq 1 - \xi_i \ \forall \ i \\ \xi_i \geq 0 \ \forall \ i \end{cases}$$

where w is the normal vector to the hyper plane, C is a penalty term (fixed), the $\xi$ are slack variables, $x_i$ represents the features of the data point i to be classified, and $y_i$ is the class of data point i.

Figure 13:
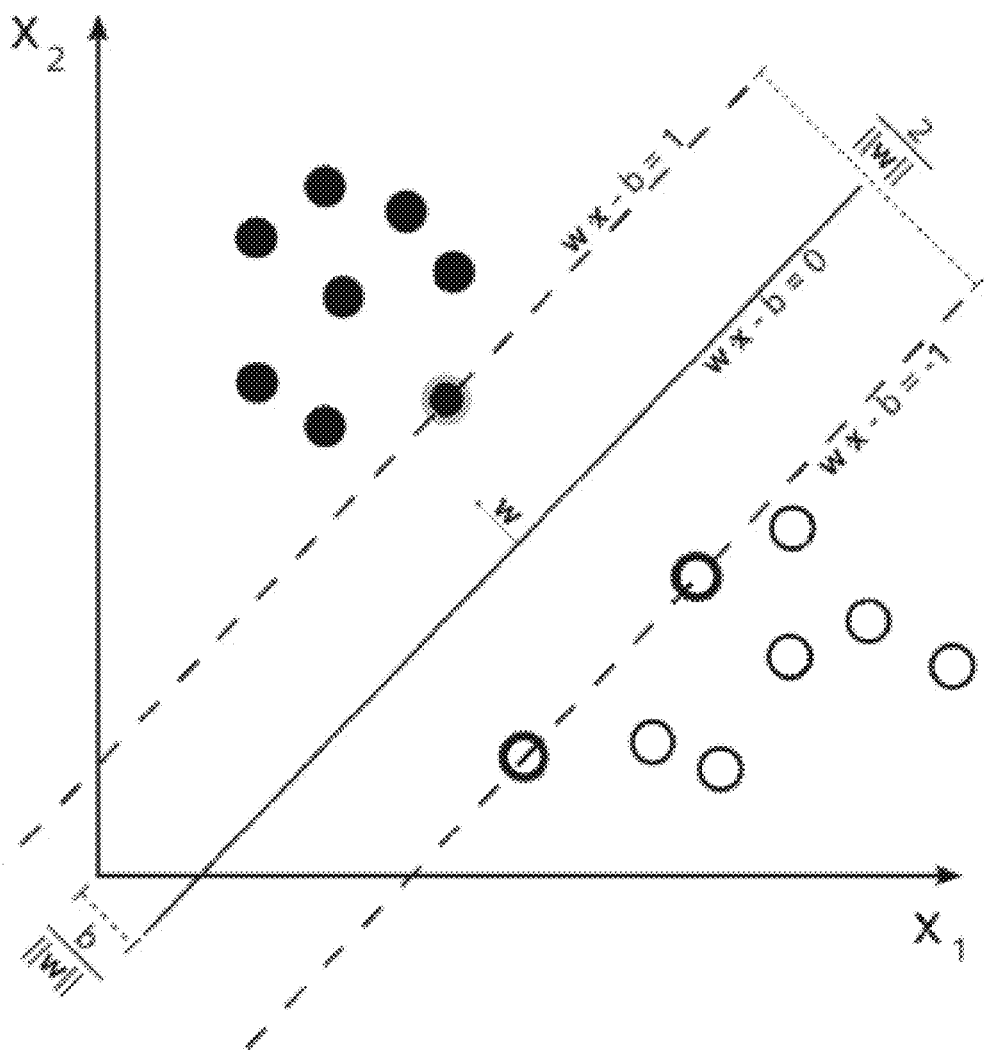
FIG. 13 is a diagram illustrating how a set of reference data points is classified into two classes by a binary SVM.

FIG. 13 is a diagram illustrating how a set of reference data points is classified into two classes by a binary SVM.

Since a SVM is a binary classifier and there are K (e.g., 18) classes of local ancestries to be classified, the classification can be decomposed into a set of binary problems (e.g., should the sequences be classified as African or Native American, African or Ashkenazi, Native American or Ashkenazi, etc.). One approach is the "one vs. one" technique where a total of $\binom{K}{2}$ classifiers are trained and combined to form a single local ancestry classifier. Specifically, there is one classifier configured to determine the likelihood that a sequence is African or Native American, another to determine African or Ashkenazi, another to determine Native American or Ashkenazi, etc. During the training process, reference data of DNA sequences and their corresponding ancestries is fed to the SVM for machine learning. When an ancestry prediction for a DNA sequence segment is to be made, each trained SVM makes a determination about which one of the ancestry pair the DNA sequence segment more likely corresponds to, and the results are combined to determine which ancestry is most likely. Specifically, the ancestry that wins the highest number of determinations is chosen as the predicted ancestry. Another approach is the "one vs. all" technique where K classifiers are trained.

Several refinements can be made to improve the SVM. For example, the number of unadmixed reference individuals can vary greatly per ancestral origin. If 700 samples are from Western Europe but only 200 samples are from South Asia, the imbalance in the number of samples can cause the Western European-South Asian SVM to "favor" the larger class. Thus, the larger class is penalized to compensate for the imbalance according to the following:

$$\begin{cases} \min_{w,\xi,b} \frac{1}{2}\|w\|^2 + \sum_G C_G \sum_i \xi_i \\ y_i(w*x_i - b) \geq 1 - \xi_i \ \forall \ i \\ \xi_i \geq 0 \ \forall \ i \end{cases}$$

$$C_G \propto \frac{1}{|G|}$$

where w is the normal vector to the hyper plane, $C_G$ is a penalty term for class G, the $\xi$ are slack variables, $x_i$ represents the features of the data point i to be classified, and $y_i$ is the class of data point i.

Another refinement is to encode strings of SNPs according to the presence or absence of features. One approach is to encode one feature at each SNP according to the presence or absence of the minor allele. Another approach is to take substrings of length 2 which have 4 features per position and which can be encoded based on their presence or absence as 00, 01, 10, and 11. A more general approach is to use a window of length L, and encode $(L-k+1)\cdot 2^k$ features of length k according to the presence or absence of the features.

The general approach is not always feasible for practical implementation, given that there are $$\sum_{k=1}^{100} (L-k+1) \times 2^k$$

features in a window of length L. With L=100, this number is approximately $10^{30}$, too large for most memory systems. Thus, in some embodiments, a modified kernel is used. In some embodiments, a specialized string kernel is used that computes the similarity between any two given windows as the total number of substrings they share. This approach takes into account that even very similar windows contain sites that have mutated, resulting in common subsequences along with deleted, inserted, or replaced symbols. Therefore, the specialized string kernel is a more relevant way of comparing the similarity between two 100 SNP windows, and achieves much higher accuracy than the standard linear kernel.

Another refinement is to use supervised learning. Supervised learning refers to the task of training (or learning) a classifier using a pre-labeled data, also referred to as the training set. Specifically, an SVM classifier is trained (or learned) using a training set of customers whose ancestry was known (e.g., self-reported ancestries). Parameters of the SVM classifier are adjusted during the process. The trained classifier is then used to predict a label (ancestry) for any new unlabeled data.

Error Correction

Figure 14:
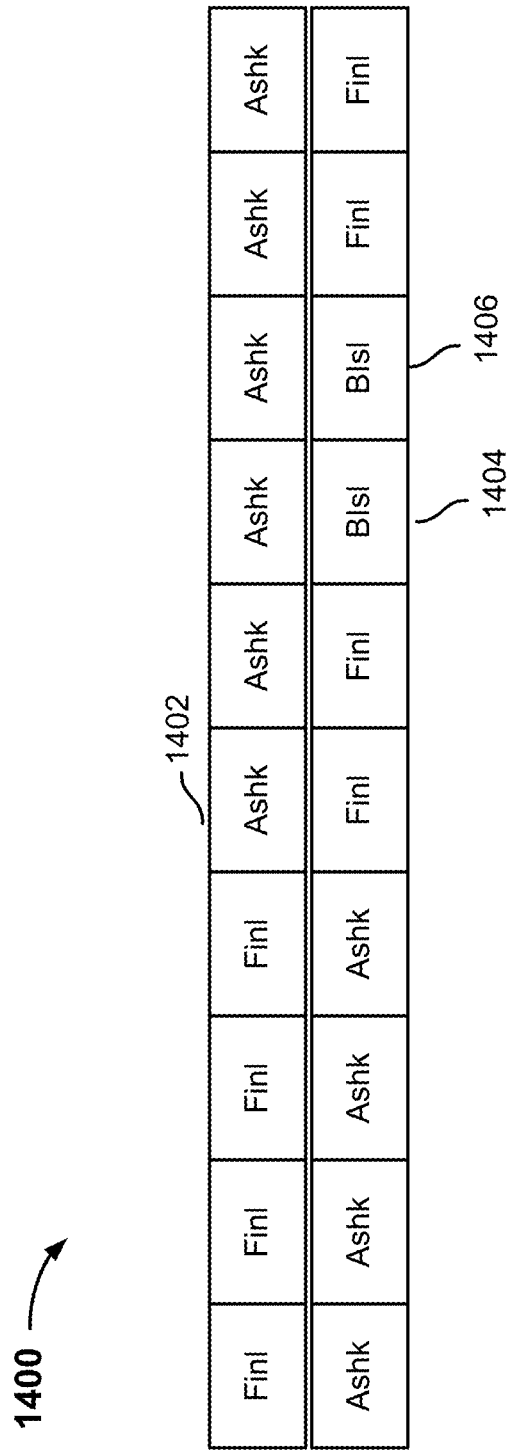
FIG. 14 is a diagram illustrating possible errors in an example classification result.

The results of the local classifier can contain errors. FIG. 14 is a diagram illustrating possible errors in an example classification result. In this example, a portion of an individual's DNA sequence is phased and locally classified. The classification result 1400 is shown, in which the top portion corresponds to the haplotype inherited from one parent and the bottom portion corresponds to the haplotype inherited from the other parent. Each segment of the individual's DNA is labeled according to the local classifier output as Finland, Ashkenazi, or British Isles. Two types of possible errors are illustrated. Starting at location 1402, the label switched from Finland to Ashkenazi for the first half of the chromosome and from Ashkenazi to Finland for the second half. This switch can be caused by a double recombination, or simply be a phasing error. At locations 1404 and 1406, there are two predictions for segments that correspond to British Isles ancestry. These repeated predictions can be evidence of ancestry changes, or be caused by correlated local classifier (e.g., SVM) prediction errors. Thus, error correction is implemented in some embodiments. In addition, because the output of the SVM tends to be noisy, the error correction process also reconciles these local ancestry estimates and produces cleaner classifications (i.e., smooths out the noise). In some embodiments, confidence scores for the ancestry assignments are also computed.

Figure 15:
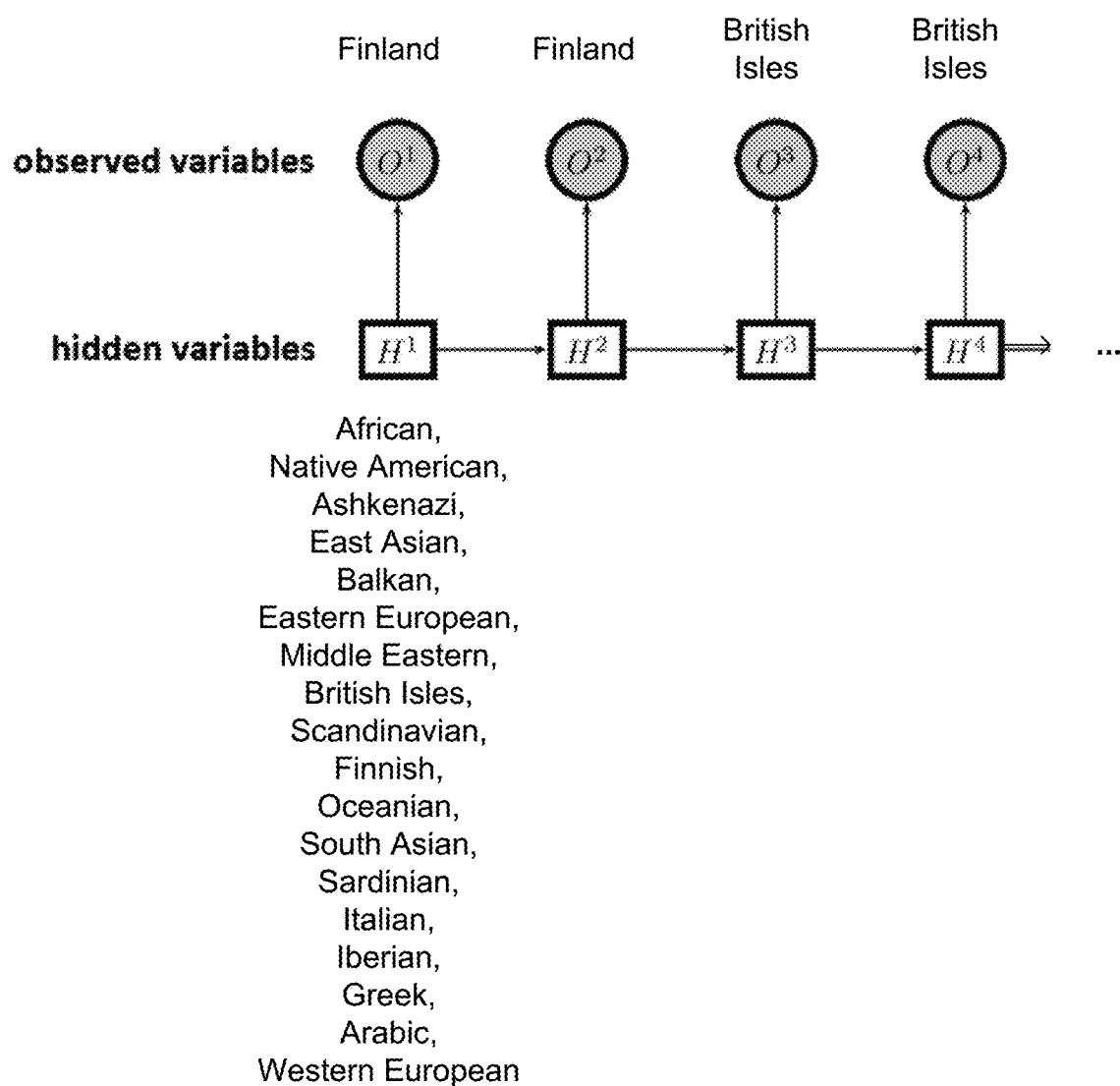
FIG. 15 is a graph illustrating embodiments of Hidden Markov Models used to model phasing errors.

In some embodiments, error correction is implemented using a Hidden Markov Model (HMM), which is a statistical model in which the input data is being modeled as a Markov process with unobserved (hidden) states. In an HMM, the observed signal (the input data) is being generated by a hidden process in a sequential manner. A standard HMM assumes that an observation, given the hidden state that generated it, is independent of all previous observations. The hidden state at any given position only depends on the hidden state at the previous position. In some embodiments, the input (observed data) to the HMM includes the predicted ancestries of DNA sequence segments (e.g., the ancestries as predicted by the local classifier for segments that are 100 SNPs in length). The hidden state corresponds to the true ancestries of the segments. The output of the HMM forms a set of smoothed ancestry origins for the segments. FIG. 15 is a graph illustrating embodiments of Hidden Markov Models used to model phasing errors. In the example shown, the observed variables $O^1$, $O^2$, $O^3$, and $O^4$ correspond to Finland, Finland, British Isles, and British Isles, respectively. The possible values for each hidden state H correspond to the set of local ancestries. Given the observed variables and the probabilities associated with the model, the most likely sequence of hidden states can be solved.

Figure 16:
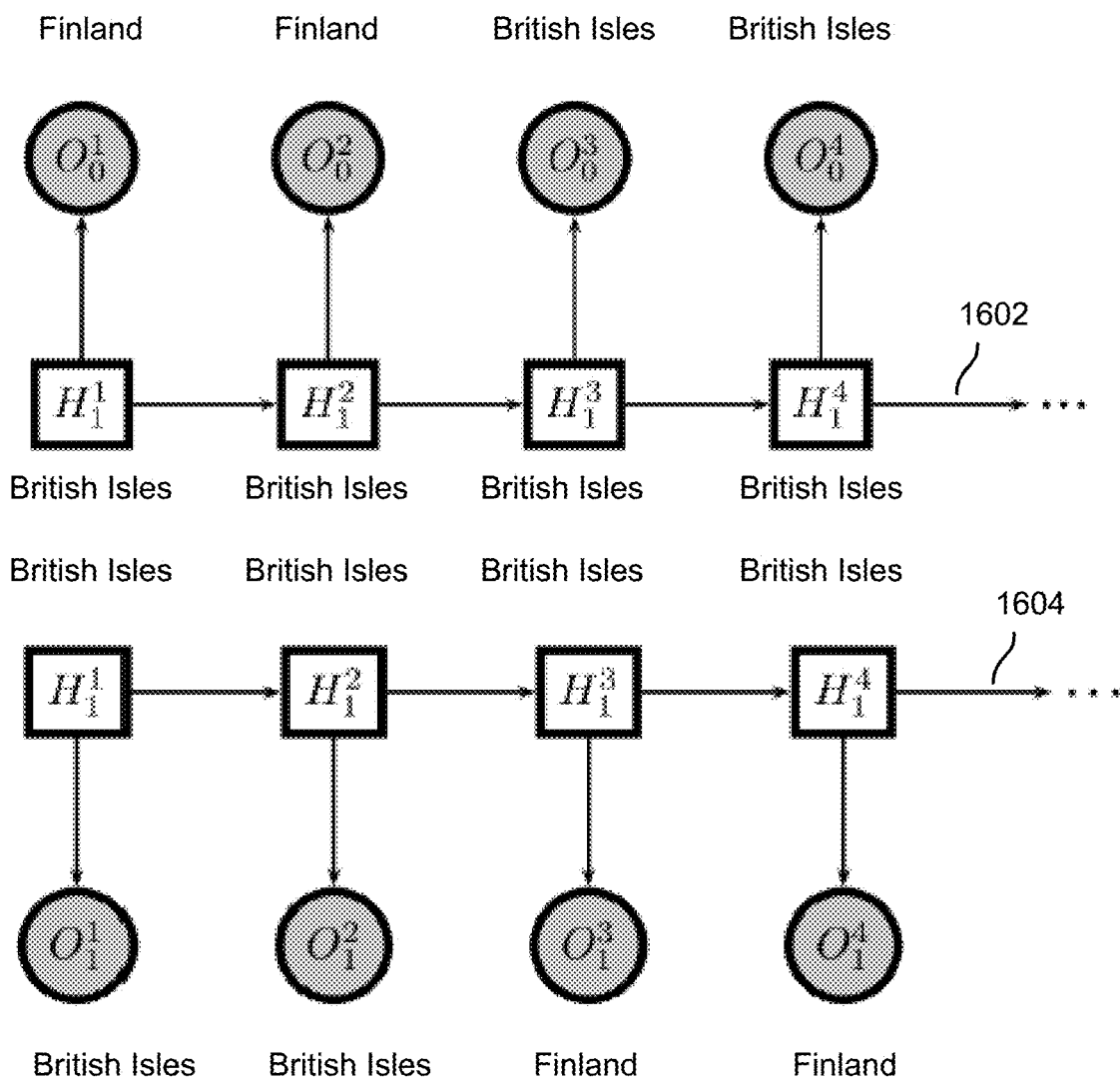
FIG. 16 shows two example graphs corresponding to basic HMMs used to model phasing errors of two example haplotypes of a chromosome.

FIG. 16 shows two example graphs corresponding to basic HMMs used to model phasing errors of two example haplotypes of a chromosome. In this example, graph 1602 illustrates an HMM corresponding to one haplotype and graph 1604 illustrates an HMM corresponding to another haplotype. The most likely sequences of the H variables have been solved and the H variables are labeled.

Figure 17:
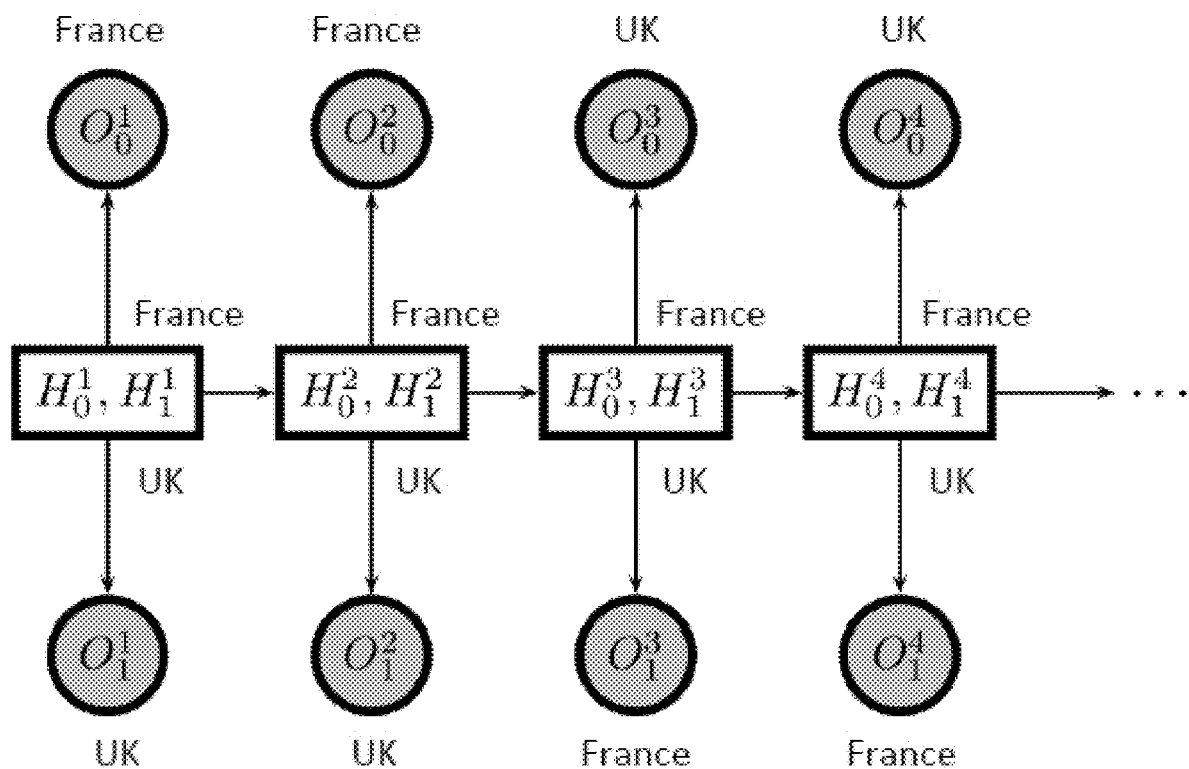
FIG. 17 is an example model of the interdependencies between observed states.

The basic model averages out the output of the learning machine and generates a smoother and less noisy output, but does not correct many of the errors in the output. For example, in FIG. 16, two HMMs model two haplotypes separately and independently. In practice, however, the switching errors in two haplotypes are not independent but instead occur together. Thus, in some embodiments, the basic HMM is improved by treating the true ancestries associated with two haplotypes at a given location as a single hidden state. FIG. 17 shows an example graph in which one HMM jointly models both haplotypes to account for potential phasing errors. This model is referred to as a Pair Hidden Markov Model (PHMM). In this case, the pair of true ancestries of both haplotypes at a given location is treated as the hidden state at the location. The PHMM accounts for the phasing errors (e.g., error at location 1402 of FIG. 14) that are present in the output of the local classifier.

Figure 18:
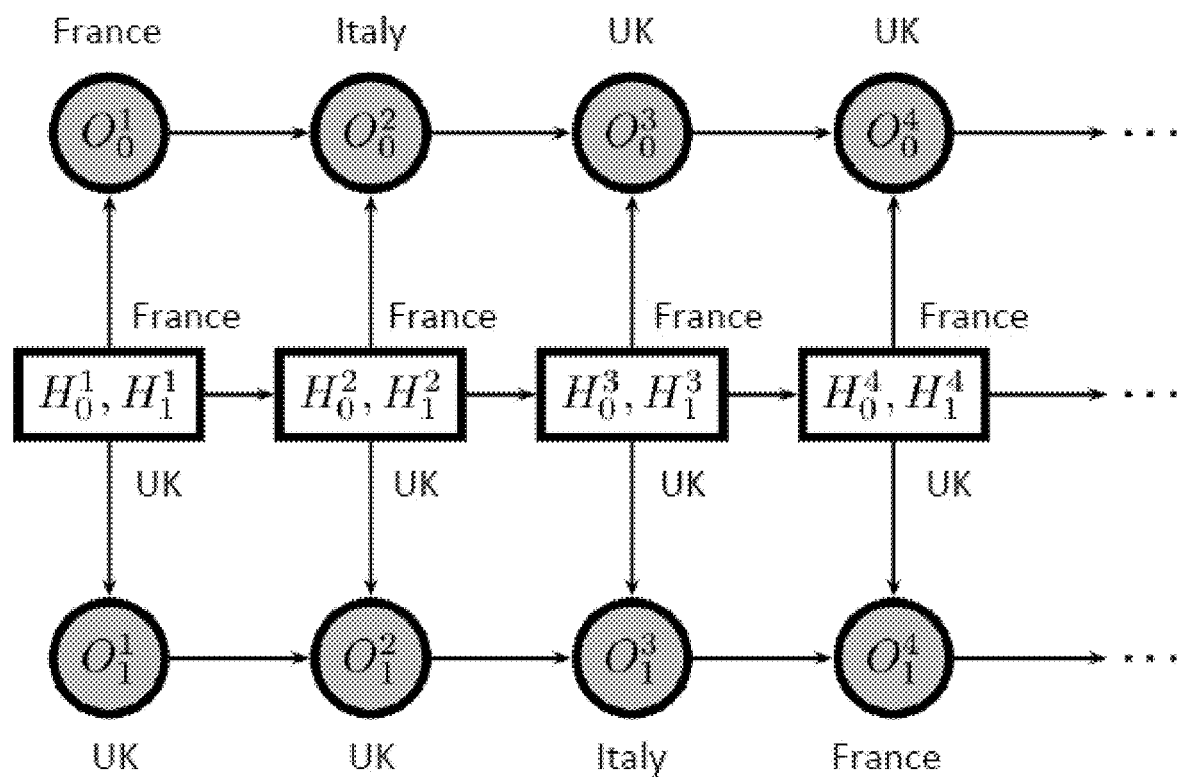
FIG. 18 is an example graph of an Autoregressive Pair Hidden Markov Model (APHMM).

Also, in FIG. 16, the basic HMMs assume that the observed data are computed independently (in other words, the Os are uncorrelated). In practice, the classification errors are correlated. For example, since long stretches of DNA can be inherited from one generation to the next, the true ancestries of adjacent DNA segments can be correlated. Thus, in some embodiments, the model of FIG. 17 is further improved to model the interdependencies between observed states. The improved model is another type of PHMM, referred to as an Autoregressive Pair Hidden Markov Model (APHMM). FIG. 18 shows an example graph of an Autoregressive Pair Hidden Markov Model (APHMM). In this example, a given observed state $O^i$ depends both on its corresponding underlying hidden state $H^i$ and on the previous observed state $O^{i-1}$.

The graph defines a probabilistic model as follows:

$$\Pr(H^1, H^2, H^3, \ldots, O^1, O^2, O^3, \ldots) = \Pr(H^1)\Pr(O^1|H^1)$$
$$\Pr(H^2|H^1)\Pr(O^2|H^2, O^1)\Pr(H^3|H^2)\Pr(O^3|H^3, O^2) \ldots$$

where probabilities $P(O^i|H^i, O^{i-1})$ are referred to as the emission parameters, and probabilities $\Pr(H^i|H^{i-1})$ are referred to as the transition parameters.

The model outputs probabilities associated with ancestry assignments of the most probable sequence. Training is required to estimate the emission parameters and the transition parameters. In some embodiments, an expectation maximization method is used to estimate the parameters.

The emission parameters characterize how well the local classifier predicts the ancestry. Specifically, given the underlying true state of a segment, what is the probability that the local classifier will output the true state. FIG. 19 is an example data table displaying the emission parameters. The data table can be generated based on empirical data of the local classifier's output and reference data of unadmixed individuals. For example, suppose there are 1000 individuals in the reference population who have identified themselves as unadmixed Ashkenazis. The local classifier output, however, labels 1% of these individuals' segments as African, 3% as Native American, 40% as Ashkenazi, etc. Thus, P (O=African|H=Ashkenazi) is 1%, P (O=Native American|H= Ashkenazi) is 3%, P (O=Ashkenazi|H=Ashkenazi) is 40%, etc. These values are used to fill the corresponding entries in the table. The values for emission parameters are found along the diagonal of the table.

The transition parameters correspond to the probability of a particular hidden state of the model given the previous hidden state. They represent the statistical likelihood of observing certain sequences of true ancestries in the population, and therefore need to be determined based on admixed data. However, it is not possible to obtain fully transitioned and accurately labeled genomes from actual admixed individuals. Thus, to determine the transition parameters, an iterative approach is used. Initially, the transition parameters are arbitrarily chosen to establish an initial model. The initial model is used to perform error correction. Based on the error corrected results, the model is updated by applying an expectation maximization method. The process can be repeated until a final convergent model is achieved.

Once the emission parameters and the transition parameters are established, the model is fully specified. Thus, the most likely sequence of hidden variables can be determined based on the observed states using conventional HMM techniques. For example, a probabilistic scoring scheme is used to determine the most likely sequence in some embodiments. All the possibilities associated with the hidden states are listed, and a set of scoring rules are specified to reward or penalize certain events by adding or subtracting a score associated with a sequence. For example, a change in adjacent haplotypes is likely an error; therefore, whenever two adjacent haplotypes are different, the score is reduced according to the rules. A mismatched observed state/hidden state pair also indicates likely error; therefore, whenever there is a mismatch of predicted ancestry and the underlying ancestry, the score is reduced. The most likely sequence of hidden states can be determined by computing scores associated with all possible combinations of observed states and hidden states, and selecting the sequence that leads to the highest score. In some embodiments, more efficient techniques for selecting the most likely sequence such as dynamic programming are employed to break the problem down into subproblems and reduce the amount of computation required. For example, the problem can be reduced to recursively determine the best ancestry assignment for everything to the left or the right of a particular position.

As described above, training is required to obtain parameters for the PHMM (or APHMM). In some embodiments, an ensemble technique is used where reference population is grouped into distinct subsets to serve as different types of training data resulting in different types of models. For example, different types of reference individuals that tend to have similar ancestries are identified and grouped into subsets. Such subsets can be formed from admixed individuals (e.g., Latinos, Eurasians, etc.) as well as unadmixed individuals (e.g., East Asians, Northern Europeans, etc.). Data from a subset is used to determine the parameters of the model for that subset. The resulting model is a model specific to the reference group (e.g., a Latino-specific model, a Eurasian-specific model, an East Asian specific-model, a Northern European-specific model, etc.). In some embodiments, the error correction process applies its input to all available models, and the results are weighted based on confidence measures and then combined according to a Bayesian model averaging technique.

Figure 20A:
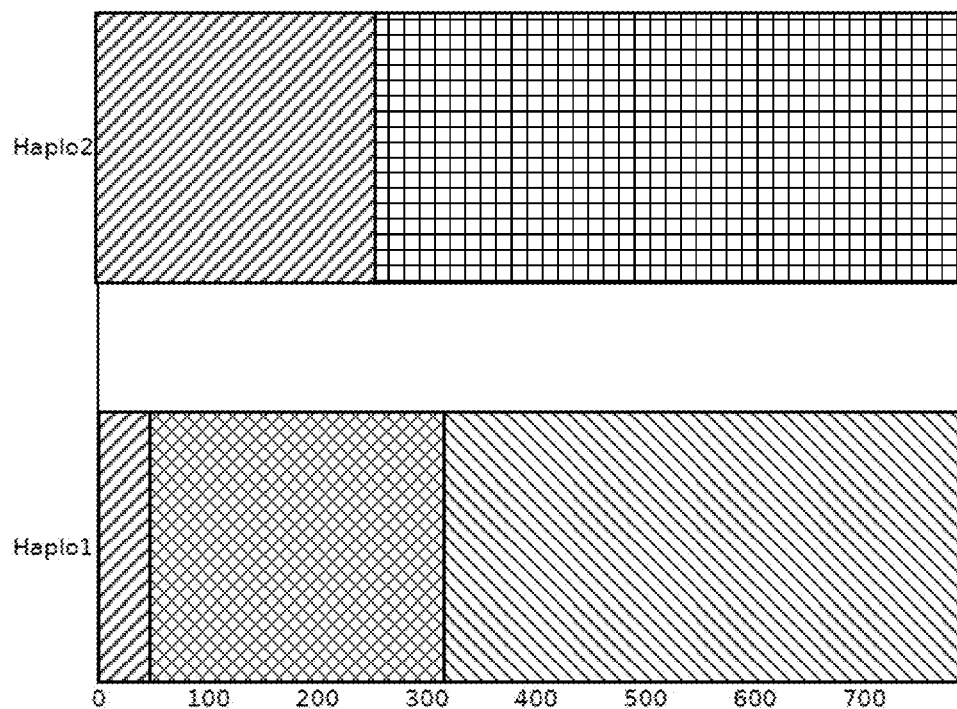
FIGS. 20A-20D are example ancestry assignment plots illustrating different results that are obtained using different techniques.
Figure 20B:
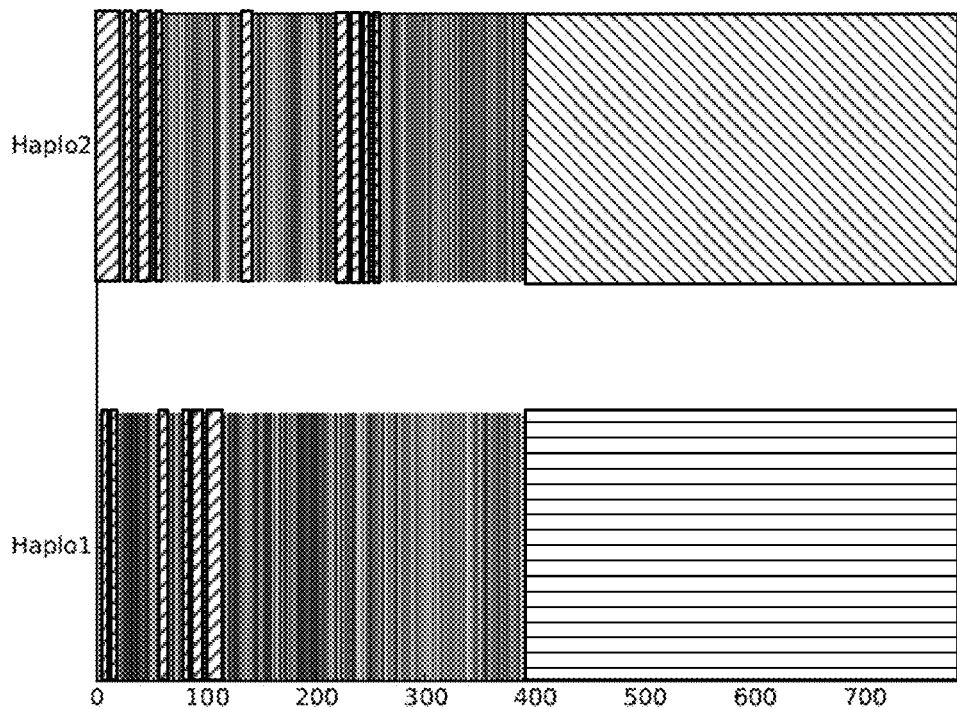
Figure 20C:
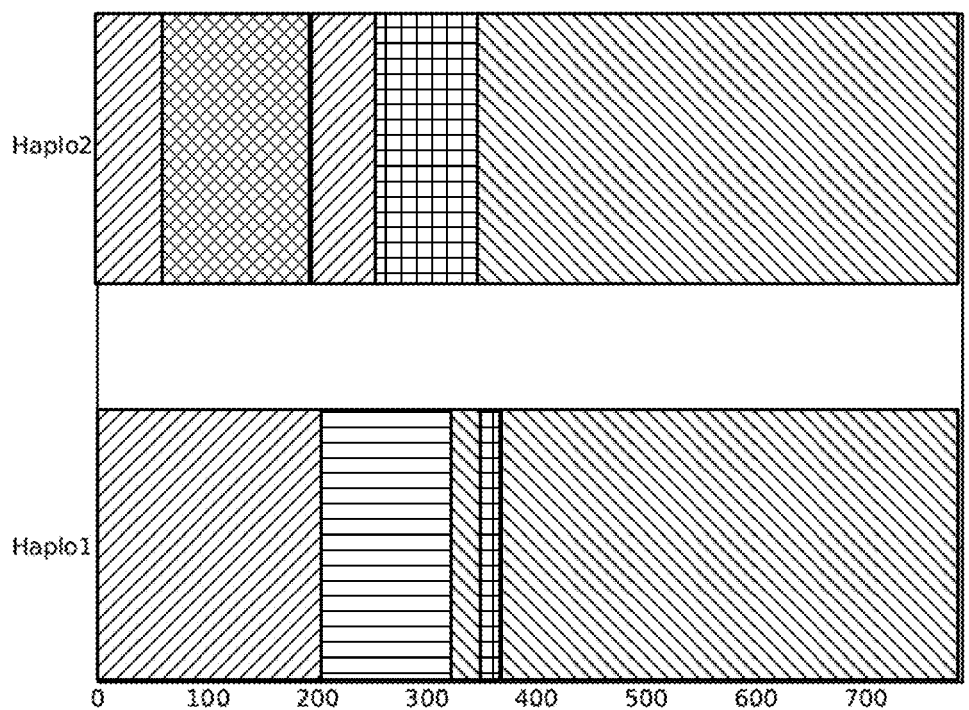
Figure 20D:
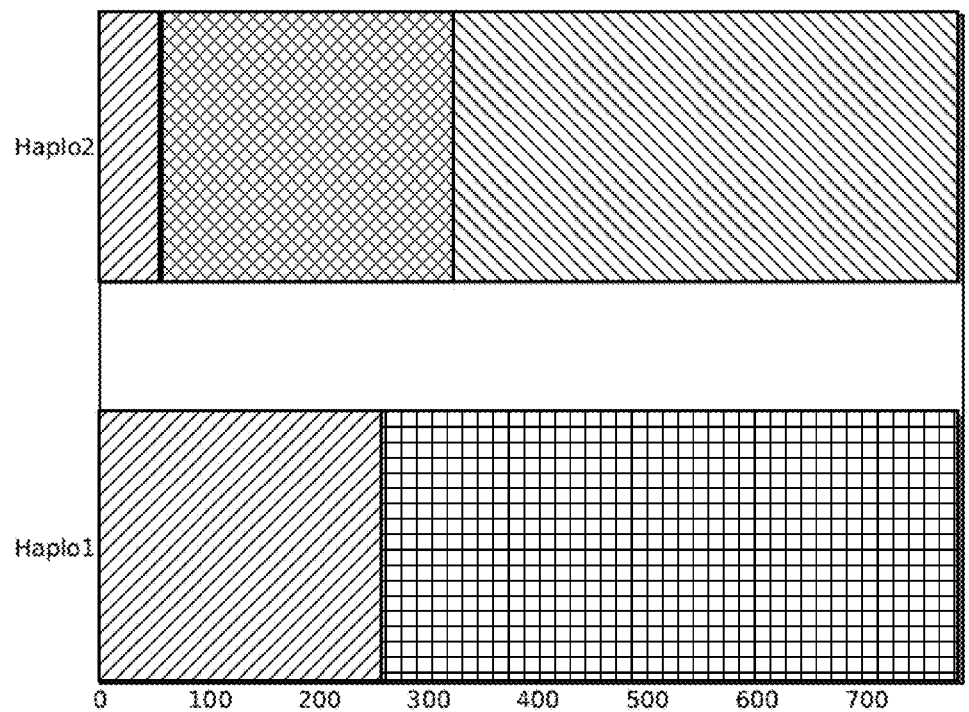

FIGS. 20A-20D are ancestry assignment plots illustrating different results that are obtained using different techniques. FIG. 20A is an example plot of ancestry assignments of two simulated haplotypes of a chromosome of a simulated individual. Each pattern in the haplotype represents a corresponding ancestry origin. This plot is referred to as the true ancestries of the haplotypes. This data is input into different types of ancestry assignment modules and the outputs are compared. First, the data is input into a local classifier without error correction to generate an output that corresponds to FIG. 20B. As can be seen, the output is very noisy, where an underlying region that actually only corresponds to a single ancestry is given many ancestry assignments by the local classifier. The local classifier output is input into a basic HMM (e.g., the HMM of FIG. 16) that performs an averaging and corrects for the noise in the local classifier output, one haplotype at a time, to generate an output that corresponds to FIG. 20C. The HMM corrects some of the noise in the local classifier output, but does not correct phasing errors or correlated classifier errors, and therefore the result does not perfectly resemble the true ancestry assignments of the two haplotypes. The local classifier output is also input into an HMM that corrects for noise, phasing errors and correlated classifier errors (e.g., the PHMM of FIG. 18 or the APHMM of FIG. 19) to generate an output that corresponds to FIG. 20D. The output perfectly matches the true ancestries of the underlying haplotypes (even though the order of the haplotypes is reversed in the output).

FIG. 21 is a table comparing the predictive accuracies of ancestry assignments with and without error correction. The "before" columns show the recall and the precision associated with unadmixed or admixed individuals using a basic HMM. The "after" columns show the recall and the precision associated with unadmixed or admixed individuals using APHMM. As used herein, recall refers to what proportion of a particular ancestry is correctly predicted, and precision refers to what proportion of a particular ancestry prediction is correct. For example, if 20% of the underlying reference data corresponds to African ancestry, and the assignment technique predicts that a given haplotype segment corresponds to African ancestry 10% of the time, then recall refers to the portion of the 20% of the African ancestry that is correctly predicted, and precision refers to the portion of the 10% of the African ancestry predictions that in fact corresponds to true African ancestry. As can be seen, recall and prediction of both unadmixed individuals and admixed individuals are improved post-error correction.

Recalibration

Figure 22A:
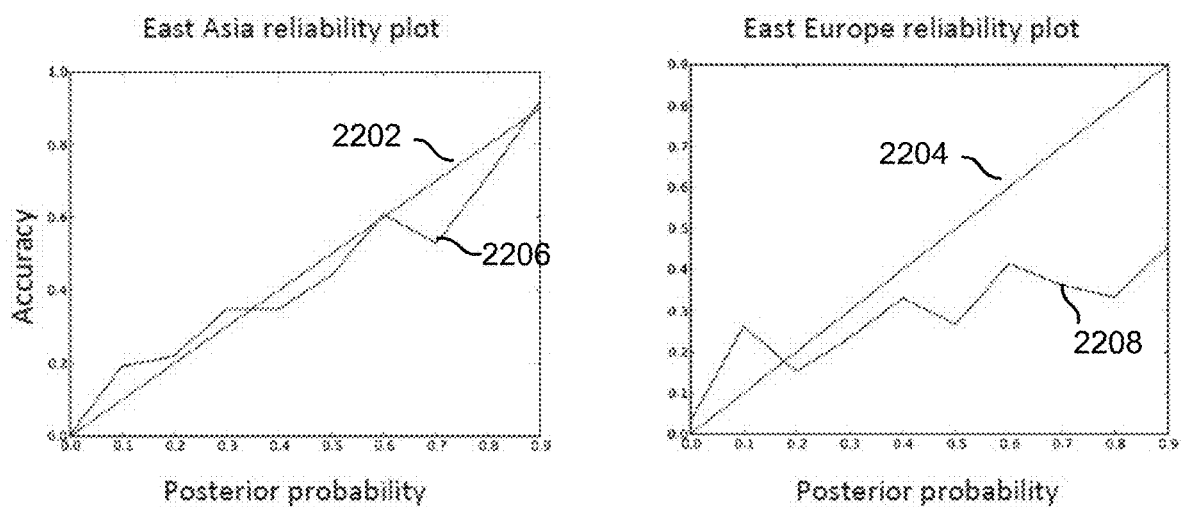
FIG. 22A illustrates example reliability plots for East Asian population and East European population before recalibration.

The error correction module outputs the most probable sequence of ancestry assignments for a pair of haplotypes, and posterior probabilities associated with the corresponding assignments. The posterior probabilities are recalibrated to establish confidence measures associated with the ancestry assignments. A well calibrated prediction with a probability of P should be correct P of the times. How well the posterior probability of the output is calibrated can be determined based on reference data of actual unadmixed individuals and/or simulated admixed individuals. For example, if it is known that in the reference data, 10% of the haplotype segments correspond to East European ancestry, but the output predicts with 80% posterior probability that 20% of all the haplotype segments correspond to East European ancestry, then the posterior probability is overly confident. By tallying the percentage of the reference data that corresponds to a specific ancestry, and applying the reference data to the predictive engine to obtain the posterior probability, a reliability plot of accuracy vs. posterior probability can be determined for each reference population corresponding to a specific ancestry. FIG. 22A illustrates example reliability plots for East Asian population and East European population before recalibration. In the example plots shown, lines 2202 and 2204 indicate the ideal accuracy-posterior probabilities correspondence, and lines 2206 and 2208 indicate the actual accuracy-posterior probabilities correspondence. Other reliability plots can be similarly determined.

In some embodiments, Platt's recalibration technique is used to recalibrate the posterior probabilities. Logistics regression is applied to posterior probabilities. A feature matrix X (e.g., $2^{nd}$ degree polynomials) is defined, and a fit is determined based on the following:

$$Pr(y=1 \mid X) = \frac{1}{1+\exp(X\theta)}$$

K-class recalibration is then performed (K being the number of local ancestries). In some embodiments, K logistic curves are fit and renormalized. In some embodiments, K logistic curves are fit and multinomial logistic regression (i.e., softmax) is performed according to the following:

$$Pr(y=i \mid X) = \frac{\exp(X\theta_i)}{1+\sum_{k=1}^{K-1} \exp(X\theta_i)} \forall\, i \le K$$

Figure 22B:
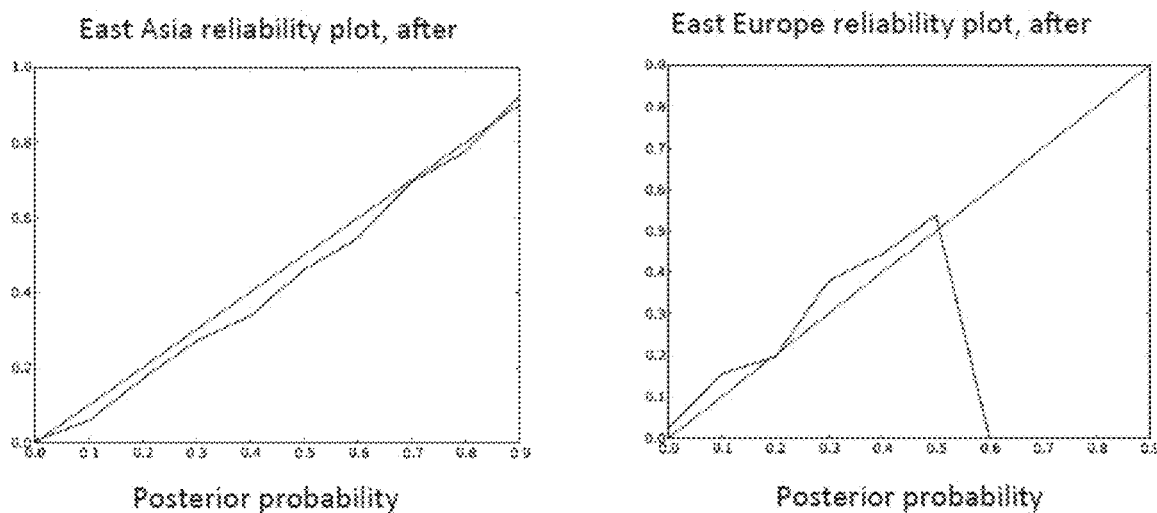
FIG. 22B illustrates example reliability plots for East Asian population and East European population after recalibration.

FIG. 22B illustrates example reliability plots for East Asian population and East European population after recalibration. It is worth noting in the original East European plot of FIG. 22A, when the posterior probability exceeds 60%, the accuracy is very poor. Thus, in the calibrated result for East European population shown in FIG. 22B, accuracy is clipped at 60%.

In some embodiments, an isotonic regression technique (e.g., the Zadrozny and Elkan method) is used to recalibrate the posterior probabilities, where recalibrated probabilities are estimated as percentages of well classified training examples falling in each bin.

Given the input of $(y_i, p_i)_i = 1, n$, the input is sorted in increasing order of $p_i$. $\phi_i$ that monotonically increases with $p_i$ but close to $y_i$ are found. In some embodiments, a pool-adjacent-violators (PAV) algorithm is used to solve:

$$\min_{\phi_1,\ldots,\phi_n} \sum_{i=1}^{n} (y_i - \phi_i)^2$$

$$\phi_1 \leq \phi_2 \leq \ldots \leq \phi_n$$

where $y_i$ is the label predicted for individual i, $p_i$ is the uncalibrated probability associated with the prediction and $\phi_i$ is the recalibrated probability.

In some embodiments, modified isotonic regression techniques are used. For example, $p_i$ can be bracketed into bins, and weights proportional to the bin sizes are introduced to reduce computational cost. As another example, regularization terms can be introduced to ensure smoothness of the output curves as follows:

$$\min_{\phi_1,\ldots,\phi_n} \sum_{i=1}^{n} \omega_i(y_i - \phi_i)^2 + C\sum_{i=1}^{n-1} (\phi_i - \phi_{i+1})^2$$

$$\phi_1 \leq \phi_2 \leq \ldots \leq \phi_n$$

In some embodiments, separate calibration regimes are used for individuals with different amounts of effective switch error. Specifically, separate calibration curves are fitted for unadmixed individuals (who have a low rate of effective switching error) or admixed individuals (who have a high rate of effective switching error).

Label Clustering

Figure 23A:
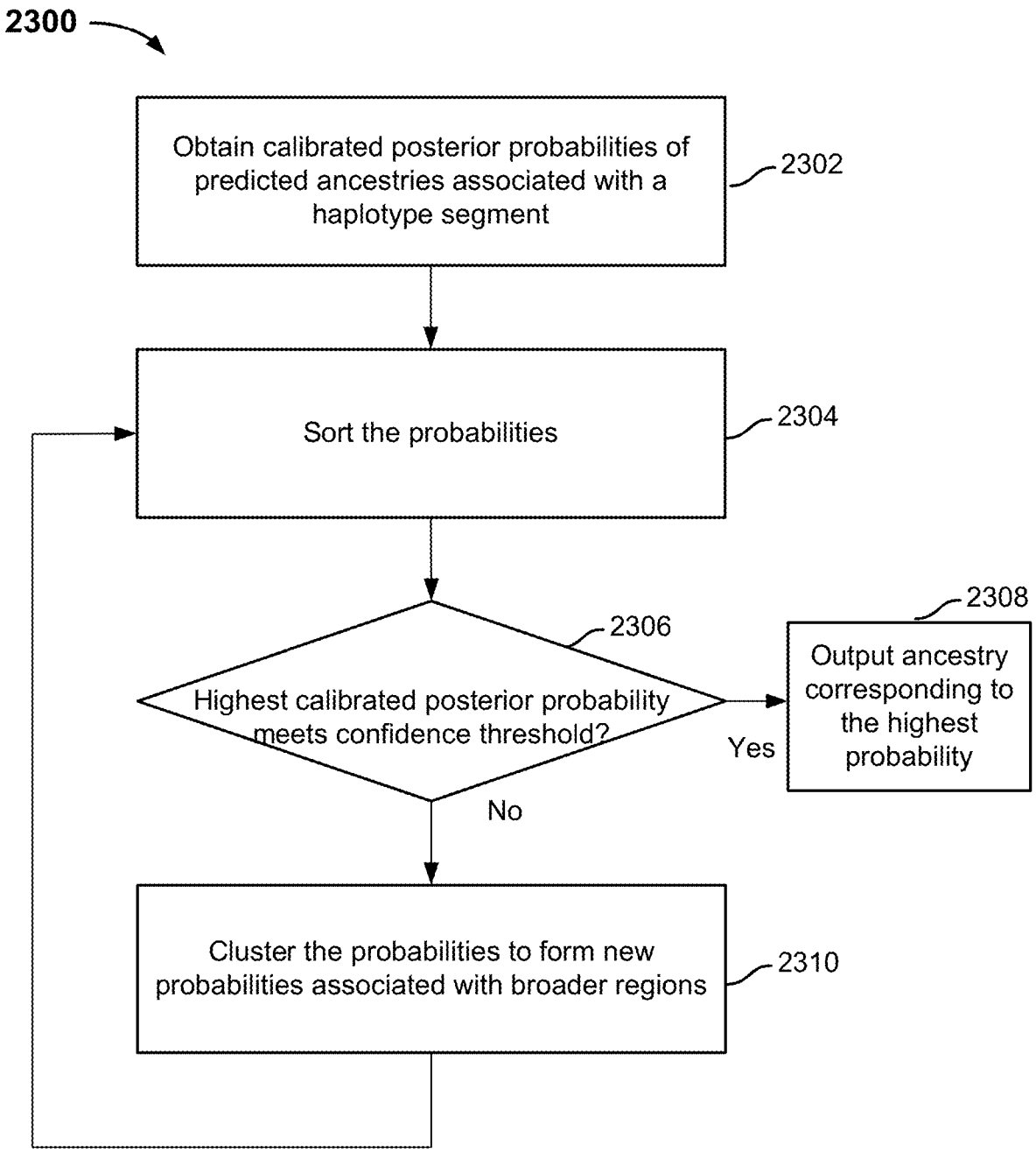
FIG. 23A is a flowchart illustrating an embodiment of a label clustering process.

In some embodiments, the recalibrated results are required to meet a threshold level of confidence before they are presented to the user. If the threshold level is unmet, the assignments are clustered and repeated as necessary until a total confidence level meets the threshold level. FIG. 23A is a flowchart illustrating an embodiment of a label clustering process. Process 2300 can be performed on a platform such as 200 or a system such as 300. At 2302, calibrated posterior probabilities of predicted ancestries associated with a haplotype segment are obtained (for example, as output of the calibration module). At 2304, the calibrated posterior probabilities are sorted according to their values. At 2306, it is determined whether the calibrated posterior probability with the highest value meets the threshold. If so, the ancestry associated with the highest calibrated posterior probability is deemed to be the ancestry of the haplotype segment and is output (e.g., presented to the user) at 2308. If, however, the threshold is not met, then, at 2310, the probabilities are clustered (e.g., summed) to form one or more new probabilities associated with broader geographical regions, and the new probabilities are clustered again at 2304. 2304-2310 are repeated until the threshold is met and a predicted ancestry of sufficiently high confidence is presented to the user.

Figure 23B:
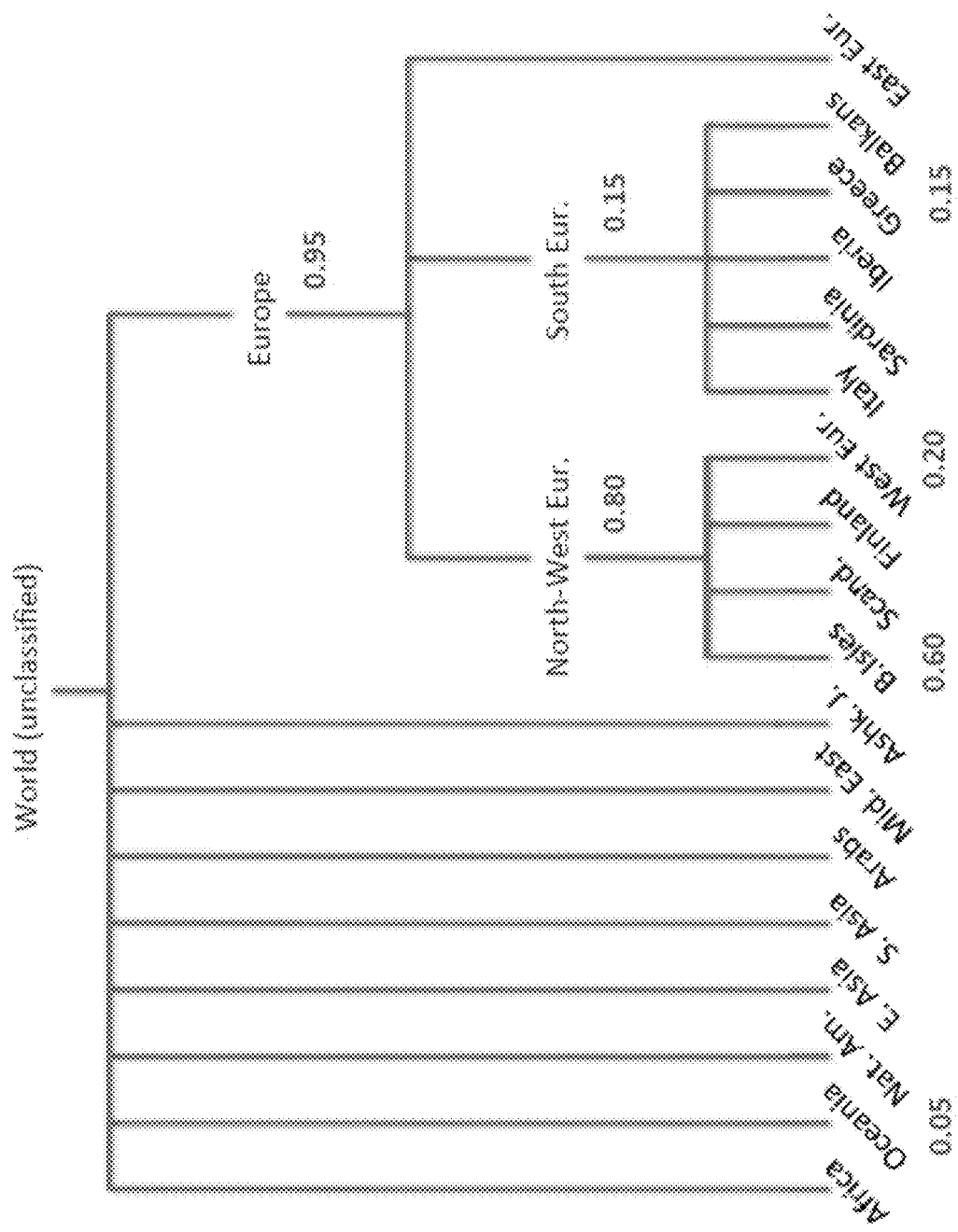
FIG. 23B is an example illustrating process 2300 of FIG. 23A.

FIG. 23B is an example diagram illustrating process 2300 of FIG. 23A. In this example, geographical locations associated with different ancestries are organized into a hierarchical tree. The root node of the tree is the world (a segment that is labeled the world means that the segment is unclassified). The next level corresponds to the continents. The next level under the continents corresponds to subcontinents. The next level corresponds to individual countries or specific geographical regions within each subcontinent. Other representations are possible. The calibrated posterior probabilities of predicted ancestries associated with the haplotype segment are as follows: 5% probability of being Oceania, 60% probability of being British Isles, 20% probability of being West Europe, 15% probability of being Greece. Depending on the value set for the threshold, different predicted ancestries can be presented. For example, if the probability is set at 60%, the ancestry of British Isles is deemed to be associated with the segment and is presented to the user. If the threshold is set at 70%, then none of the current ancestry labels meets the threshold level. Thus, the probabilities associated with specific countries or regions are clustered into subcontinents and the probabilities are summed. As shown, the probabilities associated with the British Isles and West Europe are clustered to form a probability indicating that the segment is 80% likely to be North-West European in its origin. The segment would therefore be labeled as North-West European. If, however, the threshold is set at 90%, then even at this level, no probability associated with a single node of the hierarchical tree meets the threshold. Thus, the probabilities are clustered again, combining the probabilities of North-West Europe and South Europe to form a probability that the segment is 95% likely to be from Europe. Europe is then presented as the predicted ancestry associated with the segment. As shown, if a segment cannot meet the threshold at the continental level, it is deemed to be world/generic.

The output of the label cluster outputs the predicted ancestry for each haplotype segment. In some embodiments, the information is stored in a database and/or sent to an application to be displayed.

Display of Ancestry Composition Information

In some embodiments, once the ancestries associated with the individual's chromosomes are determined, the results can be presented via various user interfaces upon user requests. The user interfaces can also present ancestry information obtained using other techniques so long as the data being presented includes requisite information such as the specific ancestries and proportions of the individual's genotype data that corresponds to the specific ancestries.

Figure 24:
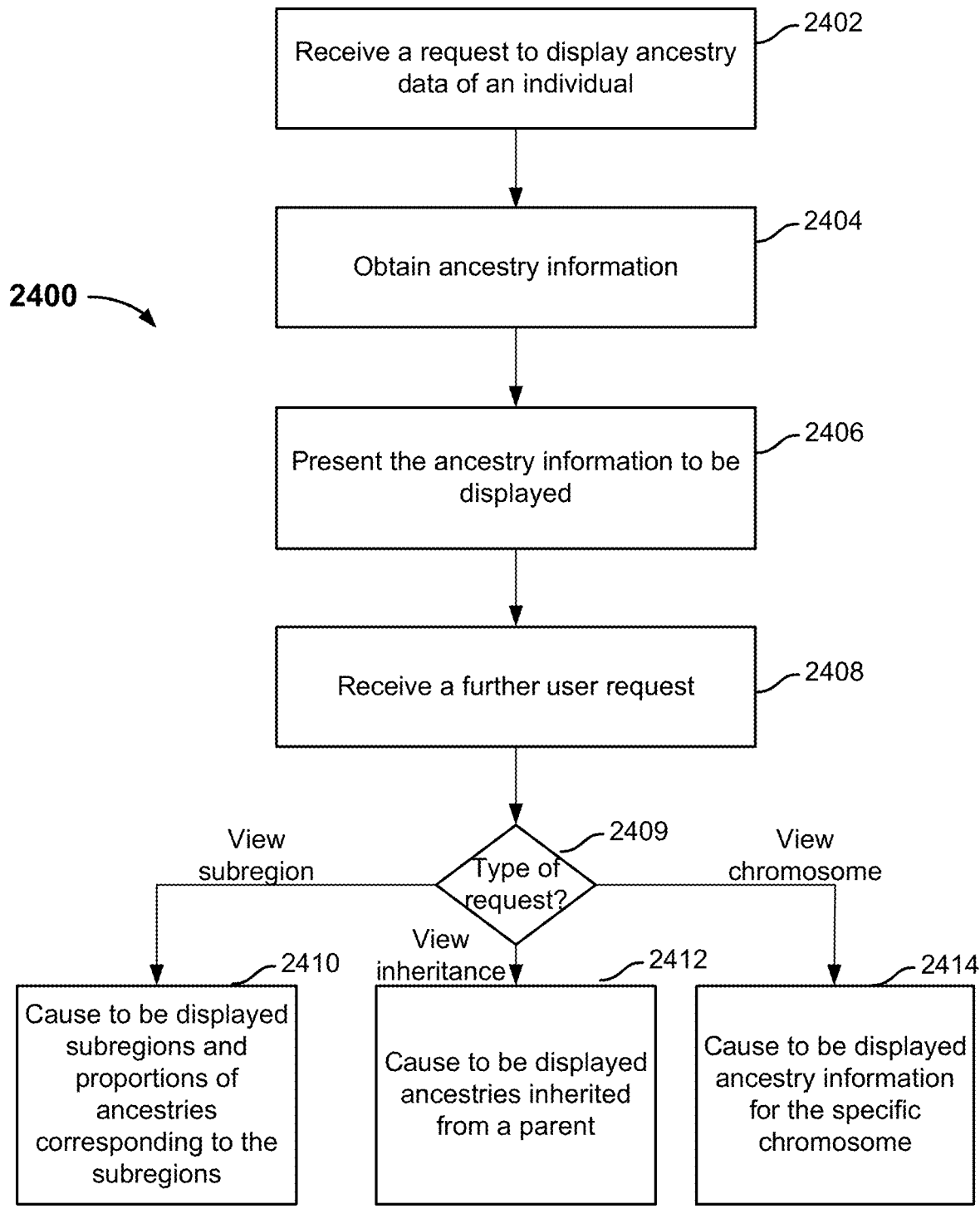
FIG. 24 is a flowchart illustrating an embodiment of a process for displaying ancestry information.

FIG. 24 is a flowchart illustrating an embodiment of a process for displaying ancestry information. Process 2400 can be performed on a platform such as 200 or a device such as 100.

At 2402, a request to display ancestry composition of an individual is received. In some embodiments, the request is received from an application that allows users to interact with their genetic information and/or ancestry data. Referring to FIG. 2 as an example, a user can make a request to display ancestry information via an application (e.g., a standalone application or a browser-based application) installed on client device 202. The application provides user interfaces (e.g., buttons, selection boxes, or other appropriate user interface widgets) as well as associated logic to interact with ancestry prediction system 206 and/or process data. The user can be the individual or another person with permission to view the individual's ancestry information.

Returning to FIG. 24, at 2404, upon receiving the request and in response, ancestry composition information of the individual is obtained. The ancestry composition information includes information pertaining to proportions of the individual's genotype data deemed to correspond to specific ancestries. In some embodiments, the ancestry composition information includes hierarchical information of different geographical regions (e.g., 40% of the individual's genome corresponds to European ancestry, of which 80% corresponds to North-Western European ancestry and 20% corresponds to Southern European ancestry; of the North-Western European ancestry, 30% corresponds to Finish ancestry and 70% corresponds to Scandinavian ancestry; of the Southern European ancestry, 50% corresponds to Italian ancestry and 50% corresponds to Greek ancestry, etc.). In some embodiments, the ancestry composition information is obtained directly from a source such as a database or the output of a pipelined ancestry prediction process. In some embodiments, raw data obtained from a source is further processed to obtain ancestry composition information. For example, if the raw data only includes predicted ancestry composition information per haplotype segment, then the segments and their ancestries are tallied to determine the proportions of the individual's genes that are deemed to correspond to the specific ancestries (e.g., 1000 out of 5000 segments are deemed to correspond to Italian ancestry and therefore 20% of the individual's genes are deemed to correspond to Italian ancestry).

At 2406, the ancestry composition information is presented to be displayed via a user interface.

In some embodiments, the ancestry composition information is initially displayed according to geographical regions and proportions of ancestries deemed to correspond to those geographical regions. Subsequently, the user can request different data to be displayed via user interfaces provided by the application. A further user request is optionally received at 2408. At 2409, the type of request is determined. In response to the further user request and depending on the type of request, different information is displayed. As shown, if the user request is a request to display subregions of a specific ancestry, subregions and proportions of the individual's ancestries corresponding to the subregions are displayed (or caused to be displayed on a display device by processors) at 2410 in response. If the user request is a request to display ancestries inherited from one or more parents, such information is displayed (or caused to be displayed) at 2412 if available. If the user request is a request to display ancestry composition information for a specific chromosome, the proportions of ancestries associated with the specific chromosome is displayed (or caused to be displayed) at 2414. Other types of requests/displays are possible.

Figure 25:
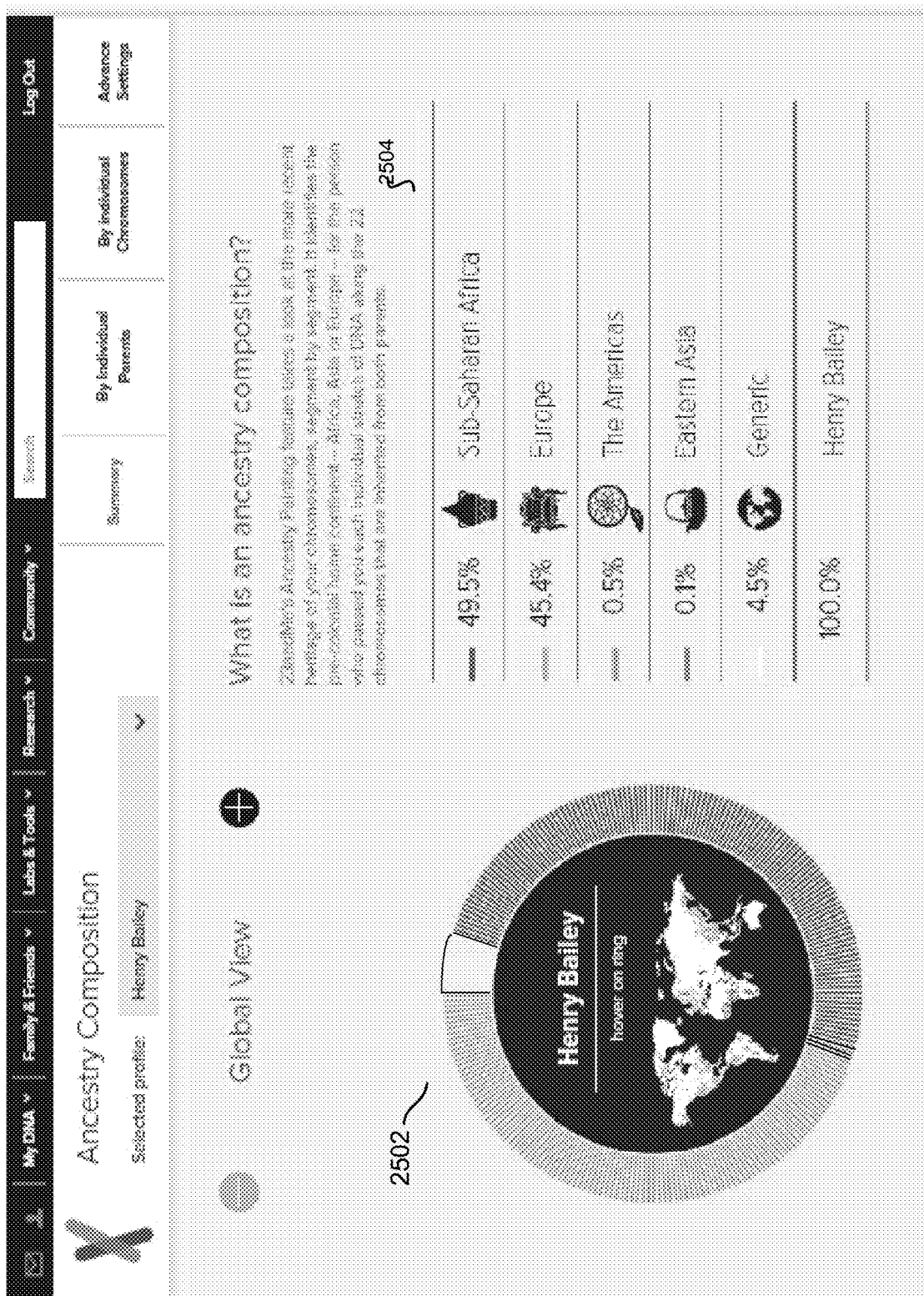
FIG. 25 is a diagram illustrating an embodiment of a regional view of ancestry composition information for an individual.

FIG. 25 is a diagram illustrating an embodiment of a regional view of ancestry composition information for an individual. In this example, proportions of the individual's autosomal chromosome segments that correspond to specific continents are displayed. The information is presented to the user using two different views: a circle view 2502 displaying the proportions as sections on a circle, where different visual formats (e.g., colors and/or patterns) represent different ancestral continents; and a list view 2504 displaying the proportions and corresponding continent names. Other views are possible (e.g., a map view displaying the regions associated with the ancestries).

Figure 26:
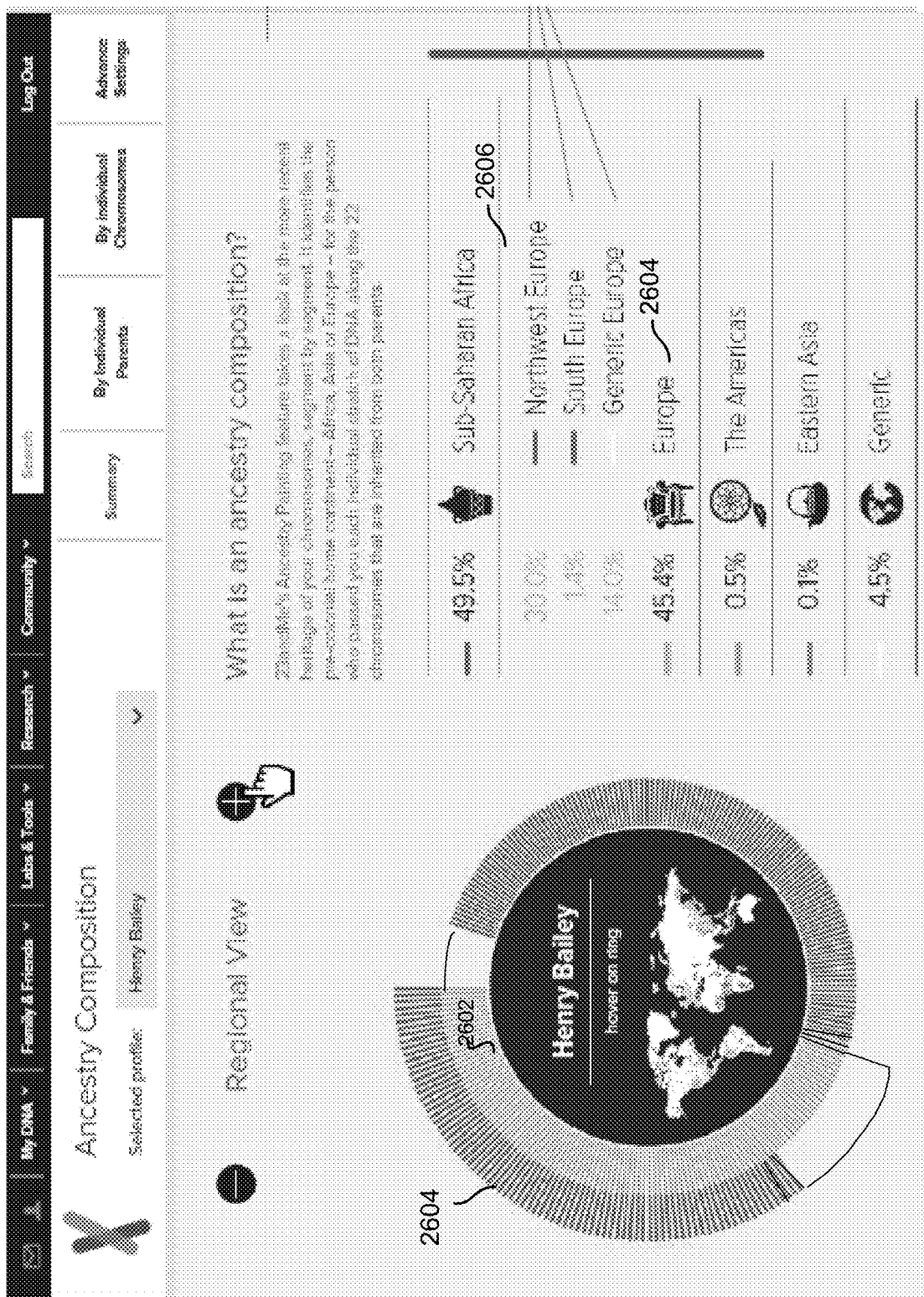
FIG. 26 is a diagram illustrating an embodiment of an expanded view of ancestry composition information for an individual.

The user is provided with the ability to expand the regions and view more detailed information pertaining to subregions. FIG. 26 is a diagram illustrating an embodiment of an expanded view of ancestry composition information for an individual. In this example, the user can request to expand the circle view by moving a cursor or other pointing mechanism over a section of the circle view (e.g., European section 2602), or by clicking on an entry in the list view (e.g., European entry 2604). In response, the application expands the section and/or the entry in the list to show subregions of ancestries for the individual. In some embodiments, the subregions are determined according to the hierarchical information of the ancestry composition information. In the example shown, a new section 2604 is created to include three subregions of Europe (Northwest Europe, South Europe, and Generic Europe) from which the individual's ancestries can be traced as well as proportions of the individual's DNA attributed to these subregions, and additional entries 2606 are created to list the subregions and the proportions.

Figure 27:
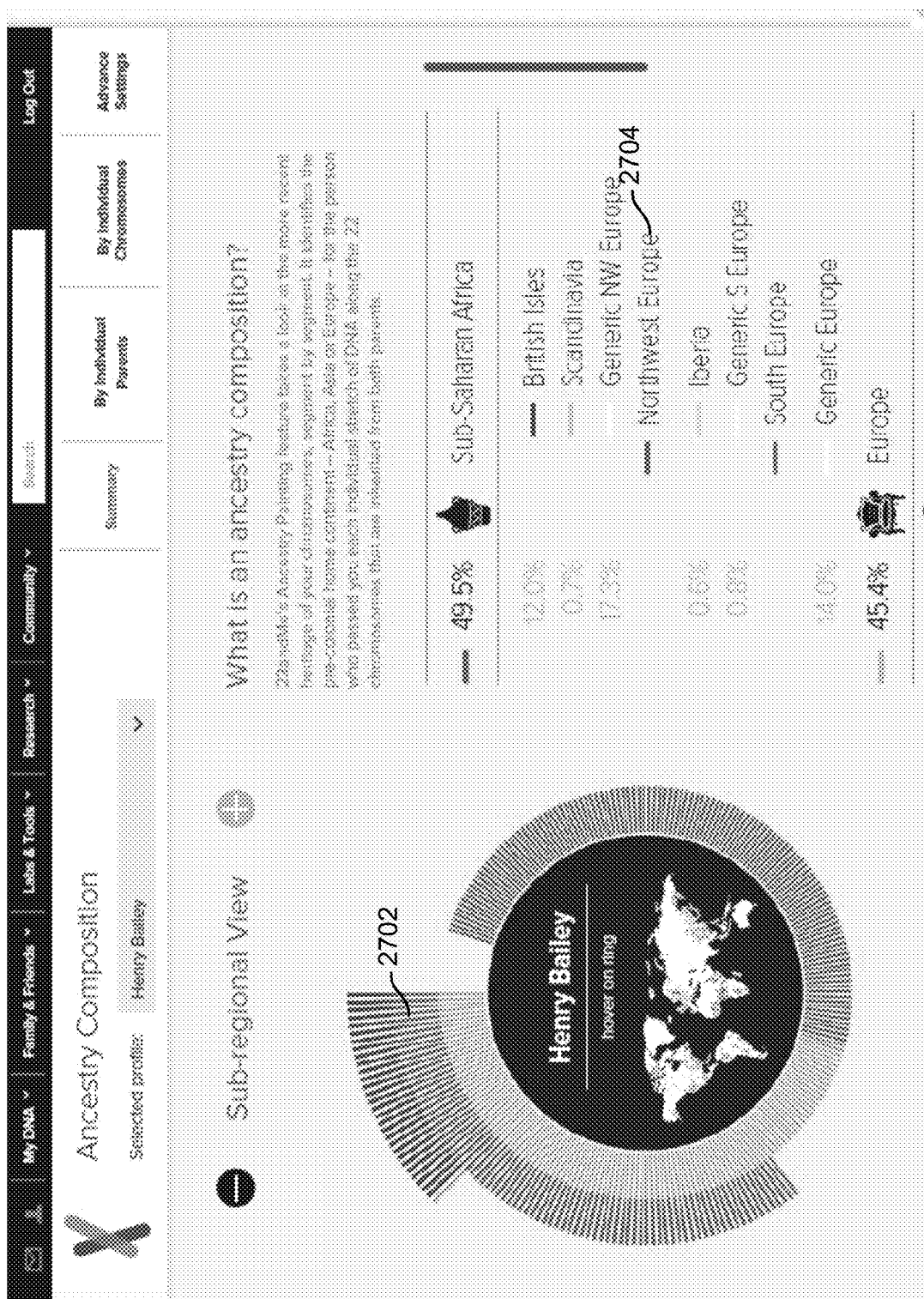
FIG. 27 is a diagram illustrating an embodiment of a further expanded view of ancestry composition information for an individual.

The subregions can be further expanded. FIG. 27 is a diagram illustrating an embodiment of a further expanded view of ancestry composition information for an individual. In this example, the user can request to expand the circle view by moving the cursor or other pointing mechanism over a subregion section (e.g., Northwest Europe section 2702), or by clicking on an entry in the list view (e.g., Northwest Europe entry 2704). In response, the application expands the subregion section and/or the entry to show more detailed composition. In this example, the Northwest European ancestry is shown to include ancestries from British Isles, Scandinavia, and generic Northwest Europe. The process can be repeated as long as more granular data is available.

Figure 28:
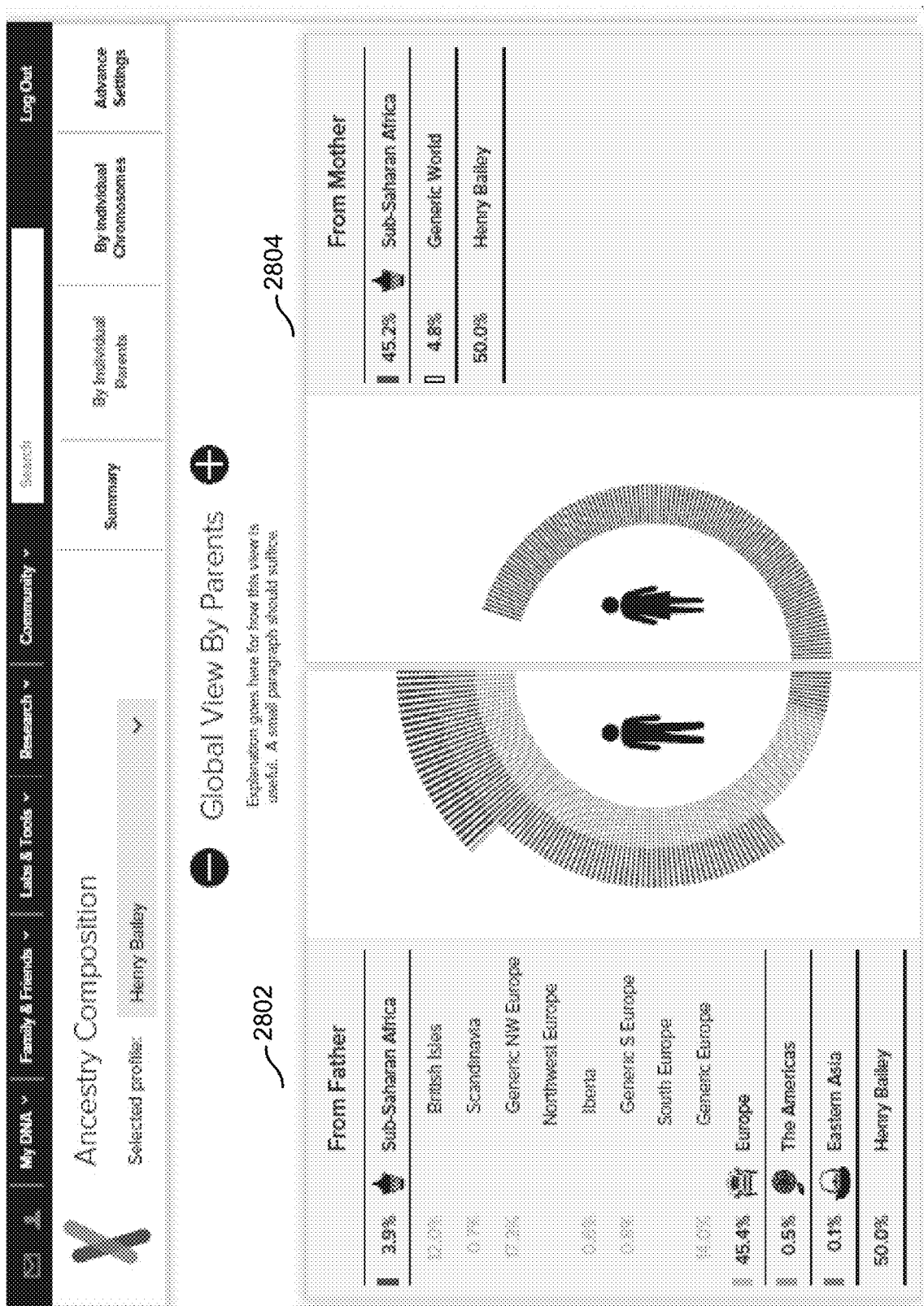
FIG. 28 is a diagram illustrating an embodiment of an inheritance view.

In some embodiments, the ancestry composition information that is obtained includes inheritance information, including proportions of the individual's ancestries that are deemed to be inherited from either the father or the mother. In other words, the inheritance information pertains to how much of the individual's DNA corresponding to a specific ancestry is inherited from each parent. For example, the trio-based phasing result can indicate that for chromosome 1, haplotype 0, segments 1-20 correspond to Scandinavian ancestry and are inherited from the mother, segments 21-45 correspond to Italian ancestry and are inherited from the mother also, segments 46-73 correspond to Greek ancestry and are inherited from the father, and so on. The segments from either the mother or the father and the corresponding ancestries of the segments are tallied, and proportions of the ancestries attributed to each parent are computed. The inheritance information computation can be done following trio-based phasing, at the time the request to display inheritance from parents is made, or at some other appropriate time. Ancestry composition information of how much of the individual's DNA corresponding to a specific ancestry is inherited from each parent is displayed. FIG. 28 is a diagram illustrating an embodiment of an inheritance view. In this example, the view is divided into two areas shown side-by-side. Area 2802 shows ancestries inherited from the father and area 2804 shows ancestries inherited from the mother. A continent-level view of ancestry composition attributed to each parent is shown initially. For example, 49.1% of the individual's DNA is deemed to correspond to sub-Saharan African ancestry, of which 3.9% is inherited from the father and 45.2% is inherited from the mother. The user is provided with the options to selectively view subregions in similar manners as described in connection with FIGS. 25-27.

Figure 29:
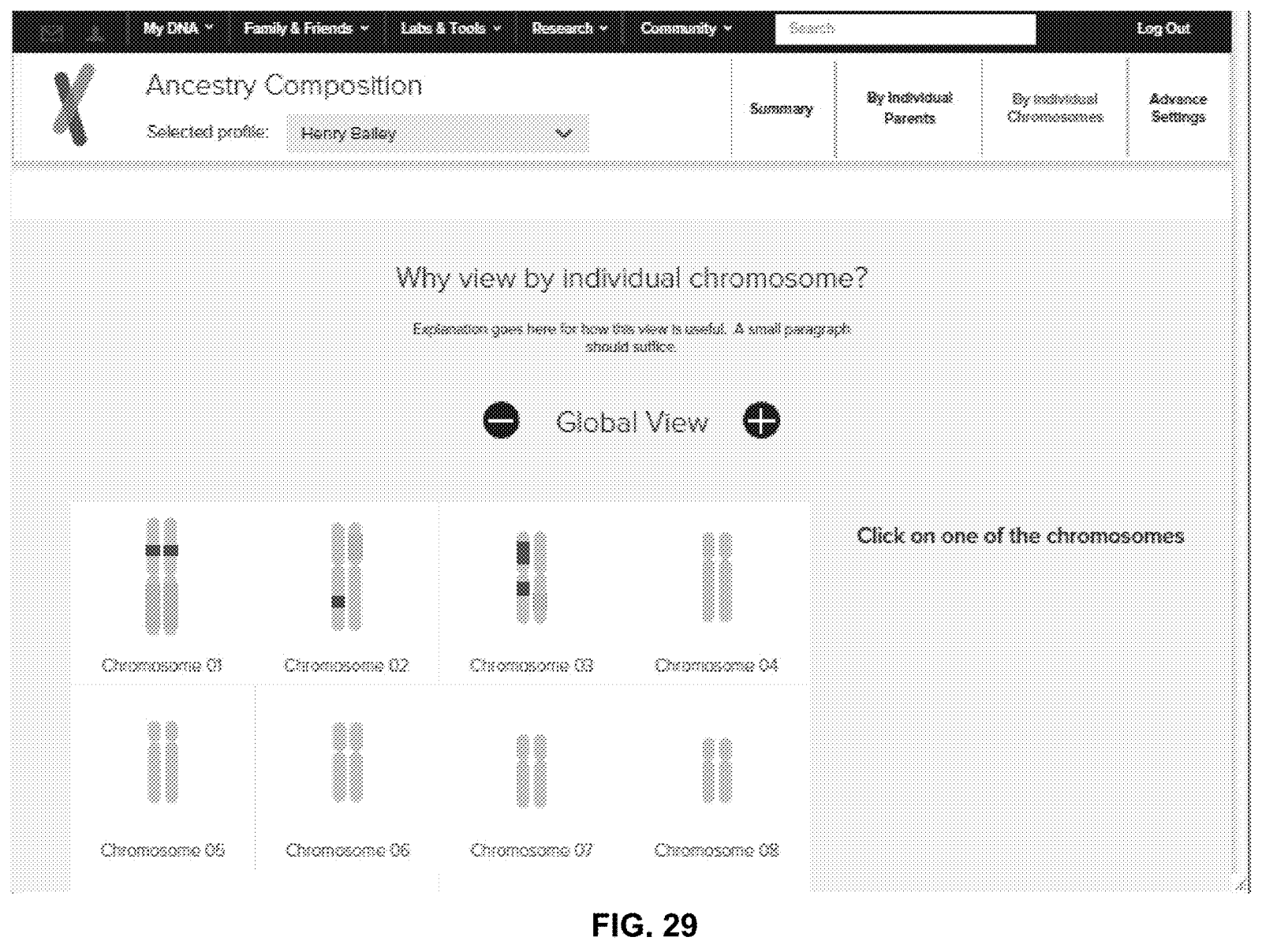
Figure 30:
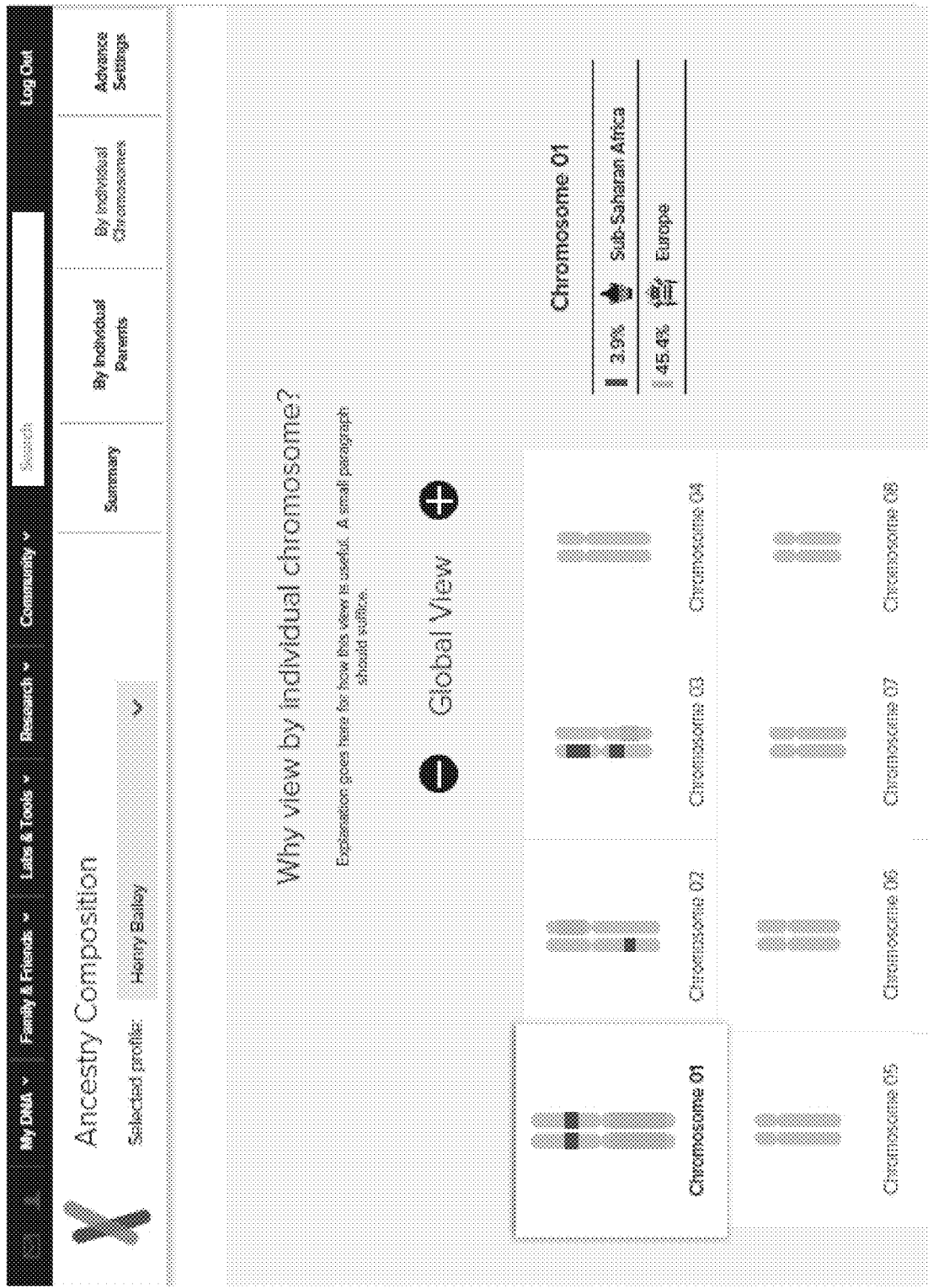

In some embodiments, since the ancestry deconvolution process is applied to individual chromosomes and the results are stored on the basis of individual chromosomes, the user has the option to select a specific autosomal chromosome or an X-chromosome to view its ancestral composition. FIGS. 29-30 are diagrams illustrating embodiments of a chromosome-specific view. In FIG. 29, a list of the autosomal chromosomes (and/or X-chromosome) that has undergone ancestry deconvolution is presented to the user. Only 8 chromosomes are displayed in the figure but more are available. The user has the option to select a specific one to view its ancestral composition. Upon receiving the user selection (e.g., chromosome 1), in FIG. 30, ancestry compositions associated with the selected chromosome are displayed in response. Although a list view is shown, other views such as the circle view shown in the preceding diagrams can also be presented. Subregions and inheritance of ancestries from a particular parent can be shown in similar manners as described in connection with FIGS. 25-28.

A pipelined ancestry deconvolution process and display of results have been described. The accuracy of ancestry predictions is greatly improved over existing techniques, and the results are presented in an informative and user-friendly fashion.

Although the foregoing embodiments have been described in some detail for purposes of clarity of understanding, the invention is not limited to the details provided. There are many alternative ways of implementing the invention. The disclosed embodiments are illustrative and not restrictive.

SEQUENCE LISTING

```
<160> NUMBER OF SEQ ID NOS: 2

<210> SEQ ID NO 1
<211> LENGTH: 12
<212> TYPE: DNA
<213> ORGANISM: Artificial Sequence
<220> FEATURE:
<223> OTHER INFORMATION: Used to demonstrate how data is processed and
      does not correspond to an actual sequence.

<400> SEQUENCE: 1 agcttttgg gg                                                          12

<210> SEQ ID NO 2
<211> LENGTH: 12
<212> TYPE: DNA
<213> ORGANISM: Artificial Sequence
<220> FEATURE:
<223> OTHER INFORMATION: Used to demonstrate how data is processed and
      does not correspond to an actual sequence.

<400> SEQUENCE: 2
agctggctgg cg                                                         12
``` tions, each section sized to represent a portion of the individual's genotype corresponding to a specific ancestry.

2. The method of claim 1, wherein the plurality of sections are presented in different visual formats to represent different specific ancestries.

3. The method of claim 2, wherein the visual formats comprise different colors and/or patterns.

4. The method of claim 2, further comprising displaying a list of the specific ancestries and their proportions of the individual's genotype corresponding to the specific ancestries.

5. The method of claim 2, further comprising displaying a map of the specific ancestries of the individual's genotype.

6. The method of claim 1, wherein the specific ancestries of the individual's genotype data represent geographical regions.

7. The method of claim 6, wherein the geographic regions comprise continents.

8. The method of claim 1, wherein the ancestry composition information includes hierarchical information of different geographical regions.

9. The method of claim 1, further comprising:
receiving, from the user via the user interface, a request to display ancestry composition information for subregions of a first specific ancestry, and

What is claimed is:

1. A computer-implemented method for graphically displaying ancestry composition information using a user interface, the method comprising:
receiving, from a user via the user interface, a request to display ancestry composition information for an individual;
obtaining ancestry composition information comprising proportions of the individual's genotype data deemed to correspond to specific ancestries; and
displaying, via the user interface, ancestry composition information of the individual in a circular representation, wherein the circle comprises a plurality of secdisplaying, via the user interface, the ancestry composition information of the individual by subregions of the first specific ancestry.

10. The method of claim 9, wherein the request to display ancestry composition information for subregions of a first specific ancestry comprises input caused by the user moving a cursor over the subregions displayed via the user interface.

11. The method of claim 9, wherein the request to display ancestry composition information for subregions of a first specific ancestry comprises input caused by the user clicking on the subregions displayed via the user interface.

12. The method of claim 9, wherein the ancestry composition information of subregions is presented in a plurality of subportions, each sized to represent a proportion of the individual's genotype corresponding a specific subregion.

13. The method of claim 9, wherein displaying the ancestry composition information of the individual by subregions of the first specific ancestry comprises expanding a first section of the circular representation for the first specific ancestry.

14. The method of claim 13, wherein expanding the first section of the circular representation shows the subregions of the first specific ancestry.

15. The method of claim 13, further comprising:
receiving, from the user via the user interface, a request to expand a first subregion of the first specific ancestry,
displaying, via the user interface, the ancestry composition information for a more specific geographic location within the first subregion.

16. The method of claim 9, wherein displaying the ancestry composition information of the individual by subregions of the first specific ancestry comprises displaying additional sections indicating geographic regions within a continent corresponding to the first specific ancestry.

17. The method of claim 1, further comprising:
receiving, from the user via the user interface, a request to display ancestry composition inherited from one or both parents; and
displaying, via the user interface, the ancestry composition information of the individual inherited from the one or both parents.

18. The method of claim 1, wherein the ancestry composition information includes inheritance information comprising proportions of the individual's ancestries inherited from each parent of the individual.

19. The method of claim 1, further comprising:
receiving, from the user via the user interface, a request to display the ancestry composition information for a specific chromosome; and
displaying, via the user interface, the ancestry composition information of the individual for the specific chromosome.

20. The method of claim 1, wherein the genotype data for the ancestry composition information is from autosomal chromosomes.

21. The method of claim 1, wherein displaying, via the user interface, the ancestry composition information of the individual comprises displaying specific continents to which the individual's genotype data corresponds.

22. The method of claim 1, wherein obtaining ancestry composition information of the individual comprises receiving the ancestry composition information from a database or a pipelined ancestry prediction process.

23. The method of claim 22, wherein the pipelined ancestry prediction process comprises:
obtaining unphased genotype data of the individual;
phasing the unphased genotype data to generate phased haplotype data; and
using a machine learning trained model to classify portions of the phased haplotype data as corresponding to specific ancestries and generate the ancestry composition information.

24. The method of claim 22, wherein the pipelined ancestry prediction process comprises
recalibrating posterior probabilities that a proportion of the individual's genotype data corresponds to a specific ancestry and generating the ancestry composition information.

25. The method of claim 22, wherein the pipelined ancestry prediction process comprises clustering posterior probabilities that proportions of the individual's genotype data correspond to specific ancestries until the clustered posterior probability meets or exceeds a threshold value.

26. The method of claim 25, wherein the clustering is performed by adding the posterior probability of specific ancestries associated with a geographical hierarchy.

27. The method of claim 1, wherein the ancestry composition information is obtained per haplotype segment.

28. The method of claim 27, further comprising tallying the ancestry composition information from a plurality of haplotype segments.

* * * * *